US011660205B2

(12) United States Patent
Rogers et al.

(10) Patent No.: US 11,660,205 B2
(45) Date of Patent: May 30, 2023

(54) DUAL-AXIS ADJUSTABLE SPINAL SYSTEMS AND INTERBODY FUSION DEVICES WITH FIXATION

(71) Applicant: SpineEX, Inc., Fremont, CA (US)

(72) Inventors: Andrew Rogers, Deephaven, MN (US); Robyn Burrows-Ownbey, Elmdale, KS (US); Eric Blossey, Denver, CO (US)

(73) Assignee: ADCURA, INC., Eden Prairie, MN (US)

(*) Notice: Subject to any disclaimer, the term of this patent is extended or adjusted under 35 U.S.C. 154(b) by 274 days.

(21) Appl. No.: 16/993,265

(22) Filed: Aug. 14, 2020

(65) Prior Publication Data

US 2021/0045892 A1 Feb. 18, 2021

Related U.S. Application Data

(60) Provisional application No. 62/887,198, filed on Aug. 15, 2019.

(51) Int. Cl.
*A61F 2/44* (2006.01)
*A61F 2/30* (2006.01)

(52) U.S. Cl.
CPC ............ *A61F 2/447* (2013.01); *A61F 2/4425* (2013.01); *A61F 2002/30505* (2013.01); *A61F 2002/30604* (2013.01); *A61F 2002/443* (2013.01)

(58) Field of Classification Search
CPC .......... A61F 2/44; A61F 2/442; A61F 2/4425; A61F 2/4455; A61F 2/446; A61F 2/4465; A61F 2/447; A61F 2002/443
See application file for complete search history.

(56) References Cited

U.S. PATENT DOCUMENTS 5,171,278 A 12/1992 Pisharodi
5,653,763 A 8/1997 Eerrico
5,665,122 A 9/1997 Kambin
5,693,100 A 12/1997 Pisharodi
6,129,763 A 10/2000 Chauvin
(Continued)

FOREIGN PATENT DOCUMENTS

CN 201861800 6/2011
CN 102369332 3/2012
(Continued)

OTHER PUBLICATIONS

PCT, International Search Report and Written Opinion of International Searching Authority in PCT/US2020/046259, dated Dec. 8, 2020, 26 pages.
(Continued)

*Primary Examiner* — Eric S Gibson
(74) *Attorney, Agent, or Firm* — Adcura IP

(57) ABSTRACT

An apparatus or a system employs a fixation assembly to stabilize and prevent migration of an interbody fusion device placed between adjacent vertebral bodies, and/or provide supplemental fixation of adjacent vertebral bodies. The fixation assembly may include modular fixation plates insertable and attachable to the interbody fusion device in situ. In certain embodiments, the fixation assembly may include a single fixation plate insertable and/or attachable to the interbody fusion device in situ. In certain embodiments, fixation plates are integrally formed with the interbody fusion device.

41 Claims, 46 Drawing Sheets

10
140
144
142
141
121
100
120
122
124
110

(56) References Cited

U.S. PATENT DOCUMENTS 6,159,244 A 12/2000 Suddaby
6,174,334 B1 1/2001 Suddaby
6,193,757 B1 2/2001 Foley
6,436,140 B1 8/2002 Liu
6,641,614 B1 11/2003 Wagner
6,905,512 B2 6/2005 Paes
7,094,257 B2 8/2006 Mujwid
7,569,074 B2 8/2009 Eisermann
7,674,296 B2 3/2010 Rhoda
7,708,778 B2 5/2010 Gordon
7,753,958 B2 7/2010 Gordon
D626,233 S 10/2010 Cipoletti
8,062,375 B2 11/2011 Glerum
8,192,495 B2 6/2012 Simpson
8,221,501 B2 7/2012 Eisermann
8,303,663 B2 11/2012 Jimenez
8,394,143 B2 3/2013 Grotz
8,398,713 B2 3/2013 Weiman
10,398,563 B2 * 9/2019 Engstrom ............... A61F 2/447
10,507,116 B2 * 12/2019 Shoshtaev ............. A61F 2/4425
10,856,997 B2 * 12/2020 Cowan ................... A61F 2/447
11,285,014 B1 * 3/2022 Josse ..................... A61F 2/4611
11,285,018 B2 * 3/2022 Shoshtaev ............... A61F 2/447
11,344,424 B2 * 5/2022 Luu ........................ A61F 2/447
2002/0151977 A1 10/2002 Paes
2002/0161444 A1 10/2002 Choi
2004/0193269 A1 9/2004 Fraser et al.
2005/0010295 A1 1/2005 Michelson
2005/0283244 A1 12/2005 Gordon
2005/0283245 A1 12/2005 Gordon
2006/0129244 A1 6/2006 Ensign
2006/0149385 A1 7/2006 McKay
2006/0206207 A1 9/2006 Dryer
2007/0100340 A1 5/2007 Lange et al.
2008/0147194 A1 6/2008 Grotz
2008/0300598 A1 12/2008 Barreiro
2009/0210062 A1 8/2009 Thalgott
2009/0222100 A1 9/2009 Cipoletti
2010/0082109 A1 4/2010 Greenhalgh
2010/0185291 A1 7/2010 Jimenez
2011/0035011 A1 2/2011 Cain
2012/0290097 A1 11/2012 Cipoletti
2012/0323327 A1 12/2012 McAfee
2013/0053966 A1 2/2013 Jimenez
2014/0288652 A1 9/2014 Boehm et al.
2015/0351925 A1 12/2015 Emerick et al.
2017/0312096 A1 11/2017 Liu et al.
2018/0042732 A1 * 2/2018 Seifert .................. A61F 2/4611
2018/0193164 A1 * 7/2018 Shoshtaev ............. A61F 2/4425
2018/0303626 A1 * 10/2018 Rogers .................. A61F 2/4455
2018/0318101 A1 * 11/2018 Engstrom ............... A61F 2/447
2018/0360616 A1 * 12/2018 Luu ....................... A61F 2/4455
2019/0117409 A1 * 4/2019 Shoshtaev ............... A61F 2/447
2019/0254836 A1 * 8/2019 Cowan .................. A61F 2/4455
2019/0269521 A1 * 9/2019 Shoshtaev ............. A61F 2/4455
2021/0045892 A1 * 2/2021 Rogers .................. A61F 2/4425
2021/0068974 A1 * 3/2021 Cowan .................. A61F 2/4425
2021/0196470 A1 * 7/2021 Shoshtaev ............. A61F 2/4455
2022/0133493 A1 * 5/2022 Josse ................... A61F 2/30771
623/17.11
2022/0133499 A1 * 5/2022 Josse ..................... A61F 2/4425
623/17.16
2022/0183854 A1 * 6/2022 Altarac ................. A61F 2/4611
2022/0211514 A1 * 7/2022 Spitler .................. A61F 2/4425

FOREIGN PATENT DOCUMENTS

EP 1925272 1/2010
EP 1706075 1/2011
EP 1903994 6/2011
WO 2005058209 6/2005
WO 2009124269 10/2009
WO 2012112596 8/2012

OTHER PUBLICATIONS

PCT, International Search Report and Written Opinion of International Searching Authority in PCT/US2014/53551, dated Dec. 18, 2014, 12 pages.
EPO, Office Action and Written Opinion in EP 14841270.3, dated Apr. 20, 2017, 5 pages.
PCT, International Search Report and Written Opinion of International Searching Authority in PCT/US2020/046258, dated Dec. 10, 2020, 7 pages.
Japanese Patent Office, Office Action in Japanese Application No. 2016-537917, dated Jun. 4, 2018, 9 pages.

* cited by examiner 300
10
220
340
328
326
324
322
310

300
324
322
340
320
328
326
310
10

DUAL-AXIS ADJUSTABLE SPINAL SYSTEMS AND INTERBODY FUSION DEVICES WITH FIXATION

TECHNICAL FIELD

This disclosure in general relates to apparatuses, systems, and methods for treating spinal diseases. In particular, various embodiments of dual-axis adjustable spinal systems and dual-axis interbody fusion devices with modular and integrated fixation are described.

BACKGROUND

Spinal fusion is a surgical procedure to correct problems relating to the human spine such as degenerative disc disease (DDD), spondylolisthesis, recurrent disc herniation, etc. It generally involves removing damaged disc and bone from between adjacent vertebrae and inserting bone graft material that promotes bone growth. As the bone grows, the adjacent vertebrae join, or fuse, together. Fusing the bones together can help make that particular area of the spine more stable and help reduce problems related to nerve irritation at the site of the fusion. Fusions can be done at one or more segments of the spine.

In an interbody fusion procedure, the nucleus pulposus and/or the annulus fibrosus that compose the intervertebral disc at the point of the damage are removed and an implant configured in shape and dimension is placed in the disc space to restore the distance between adjacent vertebrae to a proper condition. Surgical approaches to implement interbody fusion vary, and access to the patient's vertebral column can be made through the abdomen or back. One surgical method for accomplishing lumbar spinal fusion in a less invasive way involves accessing the vertebral column through a small incision on the posterior side where the surgeon removes a portion of bone and joint at the back and side of the vertebrae. These sections of bone and joint are called, respectively, the lamina and the facet joint. This procedure is known as transforaminal or lateral lumbar interbody fusion. This technique allows the surgeon to insert bone graft and spacer into the disc space from a unilateral approach laterally without having to forcefully retract the nerve roots, which can reduce injury and scarring around the nerve roots as compared to a more traditional posterior procedure.

Conventionally, once the intervertebral disc is removed from the body, the surgeon typically forces different trial implants between the vertebral bodies of the specific region to determine the size of the implant for maintaining a proper distance between the adjacent vertebrae. A proper angle between the vertebral bodies also must be maintained to accommodate the natural curvature of the spine e.g. the lordosis. Therefore, during selection of a fusion device for implantation, both intervertebral disc height and lordosis must be considered. Traditional implant devices are often pre-configured to have top and bottom surface angles to accommodate the natural curvature of the spine. It is unlikely or difficult that these values can be determined precisely prior to the operation. Further, in implementing a trial-and-error approach to sizing and fitting the interbody fusion device into the target region for geometric configuration, the patient is subjected to significant invasive activity. If a hyperlordotic sagittal profile configuration (≥20°) is set or supplemental fixation for the lumbosacral levels is desired, the surgeon may place a spinal construct in the form of anterior column fixation such as an additional plate and screw assembly to prevent possible movement or migration of the fusion device in the intervertebral disc space and/or to provide temporary stabilization of the anterior column of the spine during the spinal fusion process until arthrodesis takes place. This can require the surgeon to perform a secondary surgery after placing the fusion device, which in turn would lengthen the overall surgery time leading to more potential blood loss and complications with anesthesia for the patient.

SUMMARY

An embodiment of an apparatus comprises an interbody fusion device and a fixation assembly. The fixation assembly may include one or more modular fixation plates insertable and attachable to the interbody fusion device in situ and one or more fasteners to stabilize and prevent migration of the interbody fusion device between adjacent vertebral bodies.

An embodiment of a system comprises an interbody fusion device and a fixation assembly. The fixation assembly may include a single fixation plate insertable and attachable to the interbody fusion device in situ and two or more fasteners to stabilize and prevent migration of the interbody fusion device between adjacent vertebral bodies. Optionally, the single fixation plate provides supplemental fixation of adjacent vertebrae.

An embodiment of a system comprises an interbody fusion device and a fixation assembly. The fixation assembly may include a single fixation plate insertable and attachable to the interbody fusion device in situ and two or more fasteners to stabilize and prevent migration of the interbody fusion device between adjacent vertebral bodies. The single fixation plate can be rotated or angled relative to the interbody fusion device in situ and can provide supplemental fixation of adjacent vertebrae An embodiment of an apparatus comprises an interbody fusion device and a fixation assembly for stabilizing and preventing migration of the interbody fusion device between adjacent vertebral bodies. The fixation assembly may include one or more fixation plates integrally formed with the interbody fusion device and one or more fasteners.

This Summary is provided to introduce selected embodiments in a simplified form and is not intended to identify key features or essential characteristics of the claimed subject matter, nor is it intended to be used as an aid in determining the scope of the claimed subject matter. The selected embodiments are presented merely to provide the reader with a brief summary of certain forms the invention might take and are not intended to limit the scope of the invention. Other aspects and embodiments of the disclosure are described in the section of Detailed Description.

BRIEF DESCRIPTION OF THE DRAWINGS

These and various other features and advantages of the disclosure will become better understood upon reading of the following detailed description and the appended claims in conjunction with the accompanying drawings, where:

FIG. 1A is an isometric view, FIG. 1B a side view, and FIG. 1C a cross-sectional view.

FIG. 2A is a partially exploded view, FIG. 2B an assembled view.

FIG. 3A is an isometric front view, FIG. 3B an exploded view, FIG. 3C a back view, and FIG. 3D a side view.

FIG. 4A is an isometric front view, FIG. 4B an exploded view, FIG. 4C a back view, and FIG. 4D a side view.

FIG. 5A is an isometric view, FIG. 5B a partial enlarged view showing the attachment in an unlocked state, FIG. 5C a cross-sectional view, and FIG. 5D a partial enlarged cross-sectional view showing the attachment in an unlocked state.

FIG. 6A is an isometric view, FIG. 6B a partial enlarged view showing the attachment in a locked state, FIG. 6C is a cross-sectional view, and FIG. 6D a partial enlarged cross-sectional view showing the attachment in a locked state.

FIG. 7A is an isometric view and FIG. 7B a cross-sectional view showing accommodation of a drive shaft of a dual-axis adjustable interbody fusion device at the lower end of the channel geometry, FIG. 7C is an isometric view and FIG. 7D a cross-sectional view showing accommodation of the drive shaft at the upper end of the channel geometry.

FIGS. 8A-8D show attachment of a modular superior fixation plate to a dual-axis adjustable interbody fusion device. FIG. 8A depicts the attachment in an unlocked state, and FIG. 8B depicts the attachment in a locked state.

FIG. 10A shows attaching of a modular superior fixation plate, and FIG. 10B attaching of a modular inferior fixation plate.

FIG. 11A is an anterolateral view, and FIG. 11B an anterior transparent view.

FIGS. 12A-12B are exploded views, FIGS. 12C-12D assembled views, and FIG. 12E a cross-sectional view.

FIG. 13A is a front view, FIG. 13B an exploded view, FIG. 13C a back view, FIG. 13D a cross-sectional side view, FIG. 13E a side view, and FIG. 13F a back view.

FIG. 14A shows the attachment is unlocked, and FIG. 14B shows the attachment is locked.

FIG. 15A shows an open state of the fastener-lock mechanism, FIG. 15B a locked state of the fastener-lock mechanism.

FIG. 16A is a front view, and FIG. 16B a cross-sectional side view.

FIG. 19A is a lateral view, and FIG. 19B a transparent anterior view.

FIGS. 20A-20B are partially exploded views, and FIG. 20C-20D assembled views.

FIG. 21A is a front view, FIG. 21B an exploded view, FIG. 21C a back view, FIG. 21D a cross-sectional side view, FIG. 21E a side view, and FIG. 21F a back view.

FIG. 22A shows the attachment is unlocked, and FIG. 22B shows the attachment is locked.

FIG. 23A is an isometric end view, FIG. 23B a cross-sectional end view, FIG. 23C an isometric side view, and FIG. 23D another isometric side view.

FIG. 25A is a lateral view, and FIG. 25B a transparent anterior view.

FIG. 26A is a partially exploded view, FIG. 26B an assembled isometric view, FIG. 26C an assembled front view, and FIG. 26D an assembled end view.

FIG. 27A shows an unlocked state of the fastener-lock mechanism, and FIG. 27B a locked state of the fastener-lock mechanism.

FIG. 31A is an anterolateral view and FIG. 31B an anterior transparent view.

DETAILED DESCRIPTION OF EMBODIMENTS

Figure 1A:
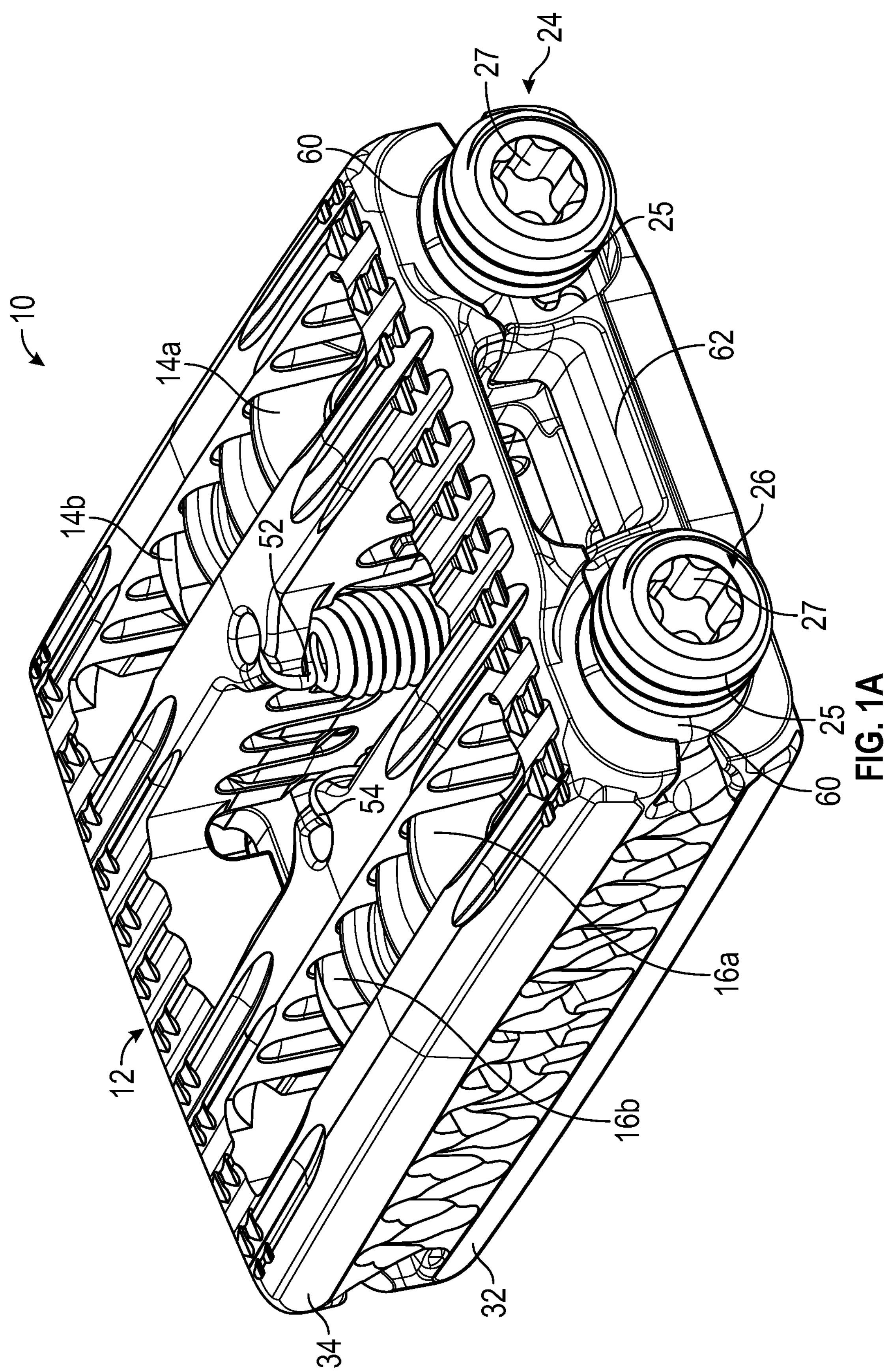
FIGS. 1A-1C depict an example dual-axis adjustable interbody fusion device according to embodiments of the disclosure.

With reference to FIGS. 1A-31B, where like reference numerals denote like parts, various embodiments of spinal systems and interbody fusion devices with fixation will now be described. It should be noted that the figures are only intended to facilitate the description of embodiments and not as an exhaustive description or a limitation on the scope of the disclosure. Further, certain specific details are shown in the figures in order to provide a thorough understanding of various embodiments of the disclosure. One skilled in the art will understand that the claimed invention may be practiced without these details. In other instances, well-known components, structures, or steps associated with the apparatuses, systems, and methods of the disclosure may not be shown or described in detail to avoid unnecessarily obscuring the description of embodiments of the disclosure. It should also be noted that certain aspects or features described in conjunction with a particular embodiment are not necessarily limited to that embodiment and can be practiced in any other embodiments.

In general, various embodiments of apparatuses or systems for treating spinal diseases comprise an interbody fusion device and a fixation assembly. The interbody fusion device can be placed between adjacent vertebrae in a region of a patient's spinal column. The configuration of the interbody fusion device can be adjusted to provide e.g. an expanded, a lordotic, kyphotic, hyperlordotic, or hyperkyphotic configuration suitable for treatment of the patient. The fixation assembly provides stabilization and prevents migration of the interbody fusion device in the expanded and/or lordotically adjusted configuration to promote safe body fusion. Alternatively, or additionally, the fixation assembly provides orthotic support or supplemental fixation to hold the adjacent vertebrae in place, which may be needed for treating certain spinal diseases. For ease of description of the disclosure, the phrase "interbody fusion device with fixation" may be used to refer to an apparatus including an interbody fusion device and a fixation assembly for stabilizing and preventing migration of the interbody fusion device; the phrase "spinal system" may be used to refer to a system including an interbody fusion device and a fixation assembly for stabilizing and preventing migration of the interbody fusion device and/or providing supplemental fixation to hold adjacent vertebrae in place.

Dual-Axis Adjustable Interbody Fusion Device

The interbody fusion device included in the spinal systems and apparatuses of the disclosure may be any suitable fusion device. According to certain embodiments of the disclosure, the interbody fusion device can be a dual-axis adjustable fusion device. A dual-axis adjustable interbody fusion device includes two driving mechanisms that can be operated separately, independently, or simultaneously in situ to adjust the configuration of the interbody fusion device with a height and/or shape suitable for treating the patient. By way of example, the configuration of a dual-axis interbody interbody fusion device placed between adjacent vertebrae can be adjusted by operating the two driving mechanisms along the anterior and/or posterior side of the patient respectively to achieve a desired sagittal balance or correct sagittal imbalance for the patient. Alternatively, the configuration of a dual-axis adjustable interbody fusion device placed between adjacent vertebrae can be adjusted by operating the driving mechanisms along the lateral and/or contralateral side of the patient to achieve a desired coronal balance or correct coronal imbalance for the patient.

An example dual-axis adjustable interbody fusion device may include a housing, a first wedge member, a second wedge member, a first drive shaft, and second drive shaft. The housing may include a first shell member and a second shell member. The first and second shell members may engage the first wedge member along a first lateral area of the housing and engage the second wedge member along a second lateral area of the housing. The first wedge member may be provided with a through-opening configured to allow the first drive shaft to pass. The second wedge member may be provided with a through-opening configured to allow the second drive shaft to pass. The first and second wedge members may be tapered members. Example tapered members include but are not limited to rotatable tapered screws and slidable tapered plates.

The first drive shaft may be operable to drive the first wedge member along the first lateral area of the housing, and the second drive shaft may be operable to drive second wedge member along the second lateral area of the housing, causing the first and second shell members to move relative to each other thereby expanding the interbody fusion device. The first and second drive shafts may be independently operated to drive the first and second wedge members to different positions, causing the expansion of the interbody fusion device along the first lateral area of the housing to a degree different from a degree of the expansion of the interbody fusion device along the second lateral area of the housing.

The first and second wedge members may be tapered members configured to slide along the first and second lateral sides of the housing to expand or contract the interbody fusion device. Alternatively, the first and second wedge members may be screw members having threads configured to rotate and move along the first and second lateral sides of the housing to expand or contract the interbody fusion device. By way of example, the interbody fusion device may comprise a first pair of screw members and a second pair of screw members. The first shell member may comprise a plurality of individual riser members, and the second shell member may comprise a plurality of individual riser members. The plurality of individual riser members of the first shell member and the plurality of individual riser members of the second shell member may define a first tracking run along the first lateral area of the housing and a second tracking run along the second lateral area of the housing. The first drive shaft may be operable to rotate the first pair of screw members allowing the first pair of screw members to travel along the first drive shaft and move on the first tracking run. The second drive shaft may be operable to rotate the second pair of screw members allowing the second pair of screw members to travel along the second drive shaft and move on the second tracking run.

Various embodiments of interbody fusion devices are described in U.S. Pat. Nos. 9,889,019, 10,188,527, and U.S. application Ser. No. 16/569,621 filed Sep. 12, 2019 entitled "Expandable and Adjustable Lordosis Interbody Fusion System." The disclosures of U.S. Pat. Nos. 9,889,019 and 10,188,527, and U.S. Ser. No. 16/569,621 are incorporated herein by reference in their entirety.

Figure 1B:
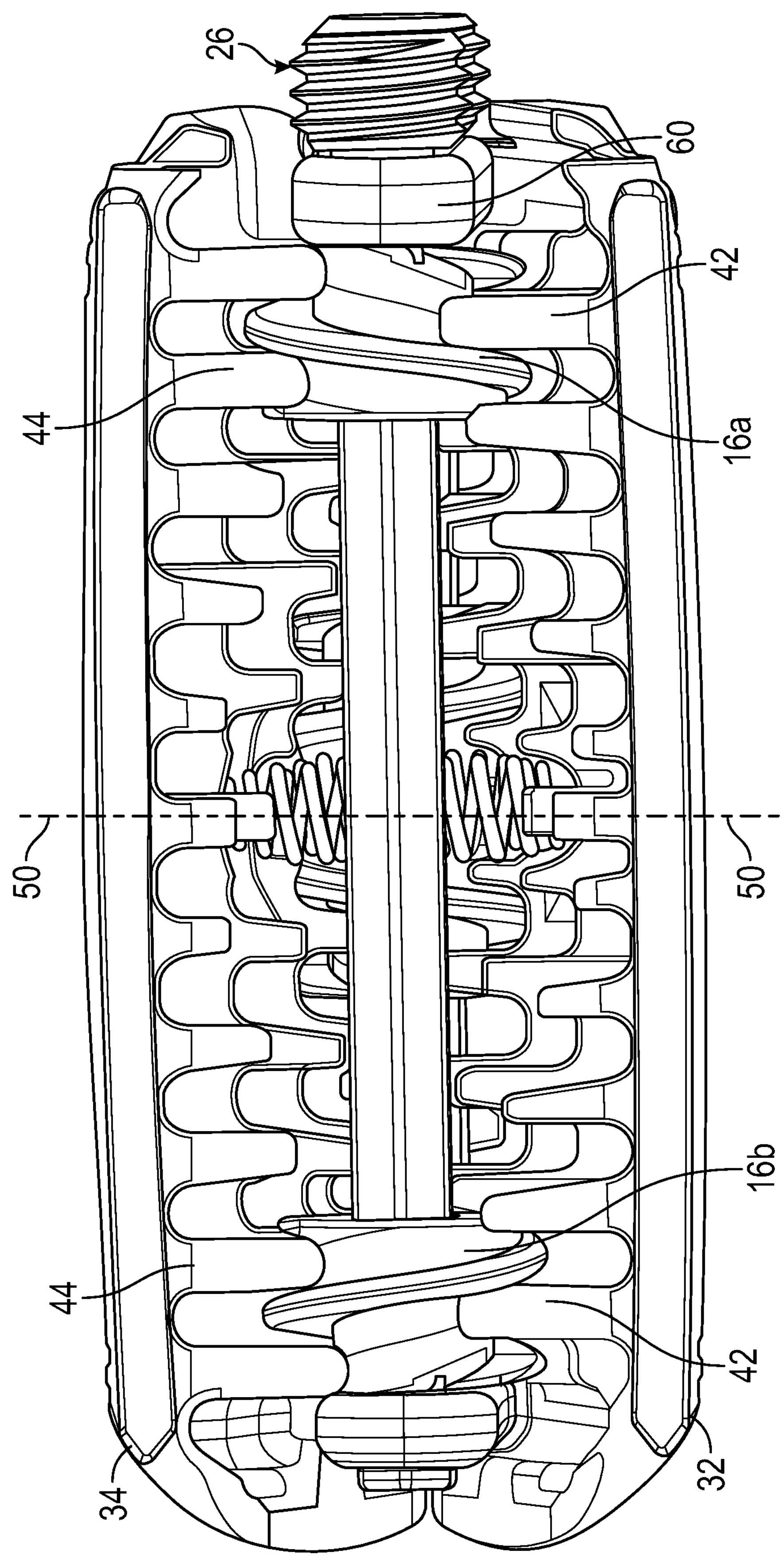
Figure 1C:
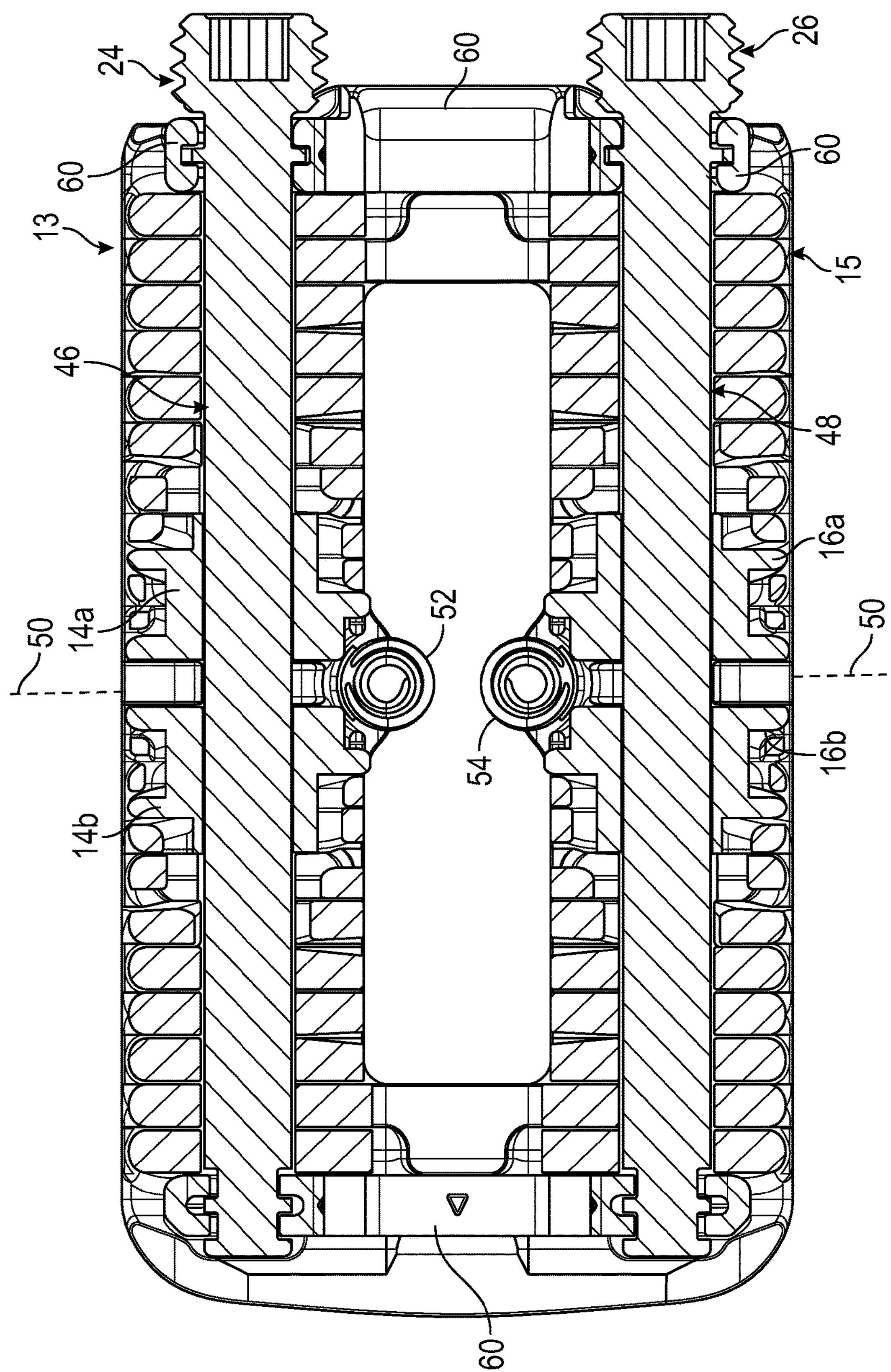

FIGS. 1A-1C show an example dual-axis adjustable interbody fusion device 10 which can be used in the spinal systems or apparatus according to embodiments of the disclosure. As shown, the dual-axis adjustable interbody fusion device 10 includes an expandable housing 12, a first pair of screw members 14*a*, 14*b*, a second pair of screw members 16*a*, 16*b*, a first drive shaft 24, and a second drive shaft 26. The first pair of screw members 14*a*, 14*b* may each be provided with a through-opening configured to allow the first drive shaft 24 to pass and engage with the first pair of screw members 14*a*, 14*b*. The second pair of screw members 16*a*, 16*b* may each be provided with a through-opening configured to allow the second drive shaft 26 to pass and engage with the second pair of screw members 16*a*, 16*b*.

The housing 12 may include a first or inferior shell member 32 and a second or superior shell member 34. The inferior shell member 32 may include a plurality of individual riser members 42 (FIG. 1B). The superior shell member 34 may include a plurality of individual riser members 44 (FIG. 1B). The plurality of individual riser members 42, 44 of the inferior and superior shell members 32, 34 may define a first step tracking run 46 along a first lateral area 13 of the housing 12 and a second step tracking run 48 along a second lateral area 15 of the housing 12 (FIG. 10). The height of the plurality of individual riser members 42, 44 may change along the first and second step tracking runs 46, 48. For example, the height of the plurality of individual riser members 42, 44 of each of the first and second step tracking runs 46, 48 may increase from a central portion 50 of the step tracking extending distally from the central portion. The first and second pairs of screw members 14*a*-14*b* and 16*a*-16*b* may each comprise a helical thread having a thickness configured to fit in the gaps between adjacent individual riser members.

The first drive shaft 24 is operable to rotate the first pair of screw members 14*a*, 14*b*, causing the first pairs of screw members 14*a*, 14*b* to move on the individual riser members 42, 44 along the first step tracking run 46. The second drive shaft 26 is operable to rotate the second pair of screw members 16*a*, 16*b*, causing the second pair of screw members 16*a*, 6*b* to move on the individual riser members 42, 44 along the second step tracking run 48. In response to the rotation of the first and second pairs of screw members 14*a*-14*b* and 16*a*-16*b*, the inferior and superior shell members 32, 34 may move relative to each other, effecting an expansion of the housing 12 or a contraction of the housing 12 from the expansion by reversing the rotation of the first and/or second pairs of screw members. The first and second drive shafts 24, 26 may be operable independently of each other. Therefore, the degree of expansion or contraction of the first lateral area 13 of the housing 12 is independently adjustable relative to the degree of expansion or contraction of the second lateral area 15 of the housing 12 when the first and second sets of screw members 14*a*-14*b* and 16*a*-16*b* are rotated independently to different positions on the first and second step tracking runs 46 and 48.

The positions of the plurality of individual riser members 42 on the inferior shell member 32 may arrange to offset from the positions of the plurality of individual riser members 44 on the superior shell member 34 so that the plurality of individual riser members 42 of the inferior shell member 32 may intermesh the plurality of individual riser members 44 of the superior shell member 34 when the housing 12 is in a contraction configuration.

The first and second pairs of the screw members 14*a*-14*b* and 16*a*-16*b* may each have a tapered configuration and comprise a helical thread. The first pair of screw members 14*a*-14*b* may be arranged or disposed such that the directional orientation of the helical thread of the first screw member 14*a* of the first pair is opposite to the directional orientation of the second screw member 14*b* of the first pair so that the first and second screw members 14*a*-14*b* of the first pair move in an opposite direction in the first step tracking run 46 relative to each other upon rotation of the first drive shaft 24. Similarly, the second pair of screw members 16*a*-16*b* may be arranged or disposed such that the directional orientation of the helical thread of the first screw member 16*a* of the second pair is opposite to the directional orientation of the helical thread of the second screw member 16*b* of the second pair so that the first and second screw members 16*a*-16*b* of the second pair move in an opposite direction in the second step tracking run 438 relative to each other upon rotation of the second drive shaft 26.

By way of example, the first and second pairs of screw members 14*a*-14*b*, 16*a*-16*b* may be arranged such that when the first drive shaft 24 is rotated in a first direction, e.g. clockwise, the first pair of screw members 14*a*-14*b* move distally from the central portion 50 respectively along the first step tracking run 46, and when the second drive shaft 26 is rotated in a second direction opposite to the first direction, e.g. counterclockwise, the second pair of screw members 16*a*-16*b* move distally from the central portion 50 respectively along the second step tracking run 48. Alternatively, the first and second pairs of screw members 14*a*-14*b*, 16*a*-16*b* may be arranged such that when the first drive shaft 414 is rotated in a first direction the first pair of screw members 14*a*, 14*b* move distally from the central portion 50 respectively along the first step tracking run 46, and when the second drive shaft 26 is rotated in a second direction same as the first direction the second pair of screw members 16*a*-16*b* move distally from the central portion 50 respectively along the second step tracking run 48.

The first and second drive shafts 24, 26 may each include features at their end portions for connecting with an operation instrument and for receiving and engaging a driver in the operation instrument. By way of example, the end portion of each of the first and second drive shafts 24, 26 may be provided with an external thread 25 for connecting with an operation instrument, and an internal thread 27 for receiving and engaging with a driver in the operation instrument (FIG. 1A).

The dual-axis adjustable interbody fusion device 10 may include one or more extension springs 52, 54 coupling the inferior and superior shell members 32, 34. The extension springs 52, 54 can assure that the entire device stays together. Extreme coronal or sagittal imbalances may exist in patients, which may apply uneven distribution of forces on the interbody fusion device when implanted in the patients. Uneven distribution of forces on the internal mechanism may cause disassociation of the fusion device. The extension spring 52, 54 may also work to keep an opposing force on the fusion. The mechanisms inside the fusion device may undergo expansion and/or lordotic adjustment once pressure is applied to the superior and inferior shell members of the device. An equal and opposite force may be needed for the mechanism to move efficiently and correctly. The extension springs 52, 54 may create an initial tension against the mechanism, allowing it to expand and/or adjust lordotically when, for example, the patient's vertebral bodies have not made contact with the device.

The interbody fusion device 10 may include one or more thrust bearing 60 configured to limit unwanted axial and/or lateral movement of the drive shafts 24, 26 while allowing the drive shafts 24, 26 to rotate about their longitudinal axes. The thrust bearing 60 may be designed to have a ramp-like geometry 62 (FIG. 1A) allowing an instrument carrying a bone graft material to be guided into the device housing 12. The ramp-like geometry may also allow for insertion of a fixation plate into the interbody fusion device for stabilizing and preventing migration of the interbody fusion device placed in adjacent vertebrae, to be described in greater detail below.

The inferior and superior shell members 32, 34 of the housing 12 may include one or more openings or windows for accepting bone graft material or allowing bone to pass as fusion occurs. Suitable bone graft materials include but are not limited to autograft and/or allogenic bone graft materials comprising e.g. cancellous and/or corticocancellous bone graft. Bone graft materials can be packed into the interbody fusion device 10 before it is placed in between the vertebral bodies and/or added after the interbody fusion device 10 is expanded and/or lordotically adjusted to a proper configuration between the vertebral bodies. The sides or edges of the inferior and superior shell members 32, 34 may include chamfered or rounded portions to facilitate insertion of the interbody fusion device into the patient's anatomy. The surfaces of the inferior and superior shell members 32, 34 may include various features such as serrations, teeth, recesses, dents, etc. to help prevent migration of the device or provide better hold.

The interbody fusion device 10 or a part of the interbody fusion device 10 can be constructed from a material comprising metal such as titanium, tantalum, stainless steel, any other biocompatible metal, or alloy. The interbody fusion device 10 or a part of the interbody fusion device 10 can also be constructed from a polymeric material such as poly-ether-ether-ketone (PEEK), poly-ether-ketone-ketone (PEKK), poly-ether-ketone (PEK), and so on.

The interbody fusion device 10 can be in any size suitable for spinal fusion procedures. By way of example, the distance from the proximal end to the distal end of the device along the direction of the drive shaft 24, 26 ("length") may range from 30 to 60 millimeters (mm). The distance from one lateral side of the device to the opposite lateral side ("width") may range from 10 mm to 30 mm. The device may be manufactured in numerous offerings with different lengths and widths in various increments, for example, 2 mm increments in width and 5 mm increments in length. The distance from the inferior shell member surface to the superior shell member surface of the interbody fusion device in a fully contracted configuration ("base height") may range from 5 mm to 10 mm. The dual-axis driving mechanisms according to embodiments of the disclosure can provide a continuous expansion in height adjustment e.g. ranging from 0 mm to 8 mm when operated simultaneously together, or e.g. ranging from 0-9 mm when operated independently of one another. The dual-axis driving mechanisms according to embodiments of the disclosure can provide a continuous angulation between the inferior and superior shell member surfaces ("lordosis") ranging from 0-30 degrees. It should be noted that the above specific dimensions are provided for thorough understanding of various aspects of the disclosure but are not intended to limit the scope of the claims.

Dual-Axis Adjustable Interbody Fusion Device with Modular Fixation

With reference to FIGS. 2A-11B, embodiments of a dual-axis adjustable interbody fusion device with modular fixation or an apparatus 100 according to the disclosure will now be described. The use of one or more modular fixation plates allows for attachment of a fixation assembly to an interbody fusion device in situ following adjustment of the interbody fusion device to a desired configuration in the adjacent vertebrae, and provides stabilization and prevents migration of the interbody fusion device.

Figure 2A:
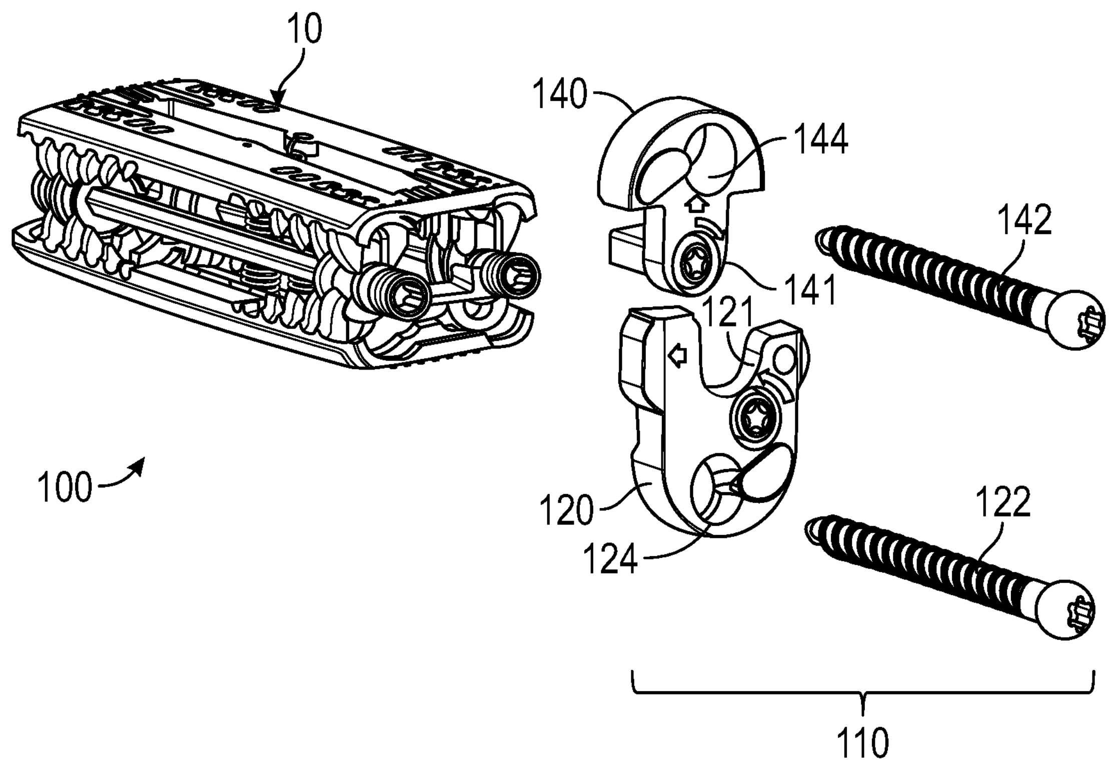
FIGS. 2A-2B depict an example dual-axis adjustable interbody fusion device with modular fixation according to embodiments of the disclosure.
Figure 2B:
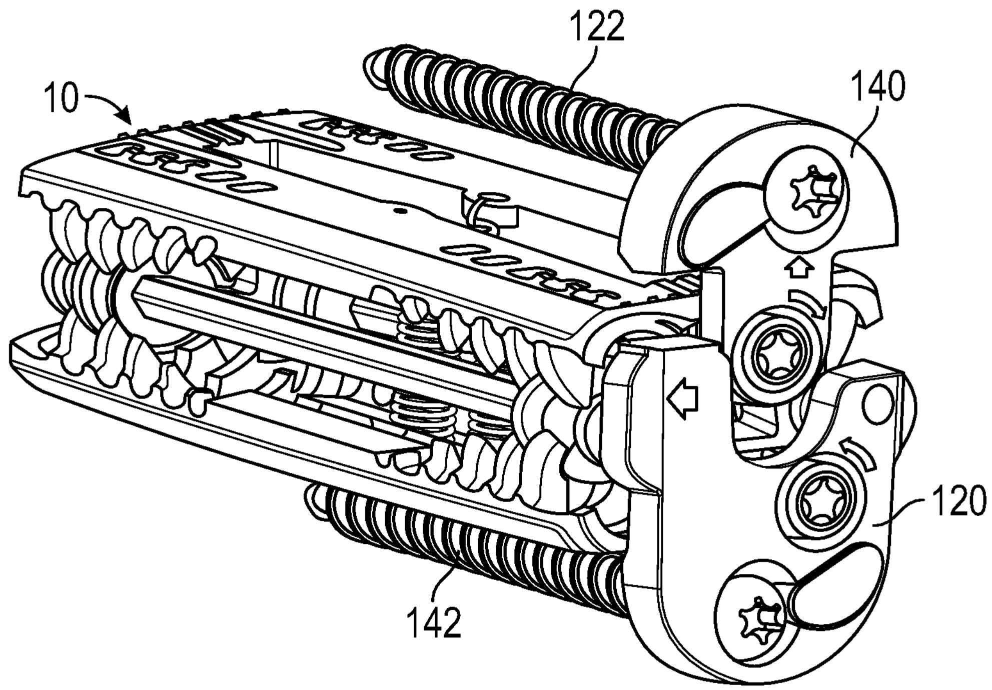
Figure 3A:
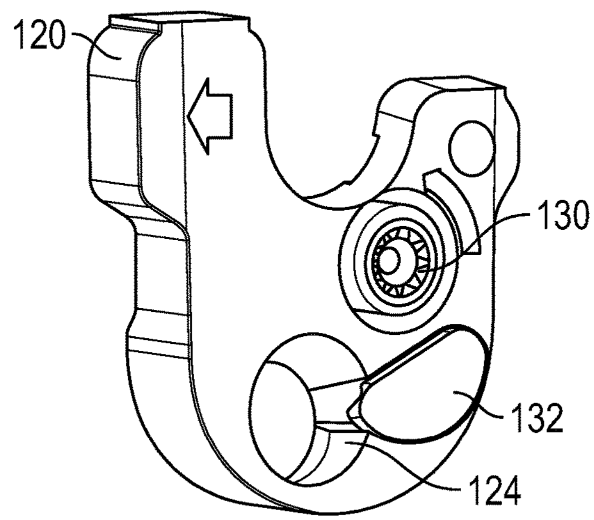
FIGS. 3A-3D depict an example modular inferior fixation plate according to embodiments of the disclosure.
Figure 3B:
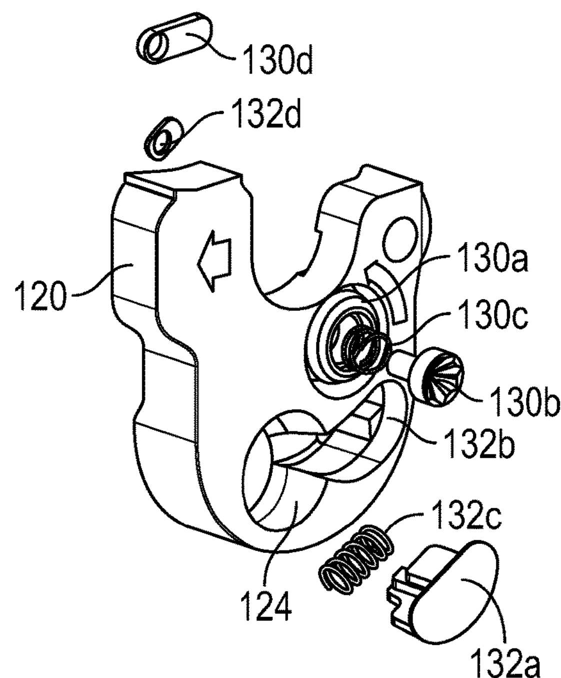
Figure 3C:
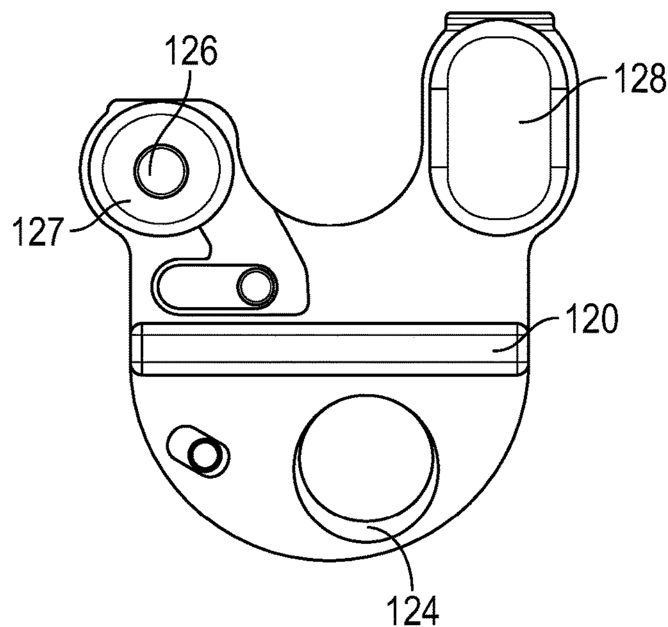
Figure 3D:
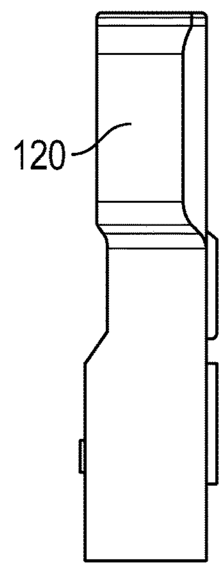
Figure 4B:
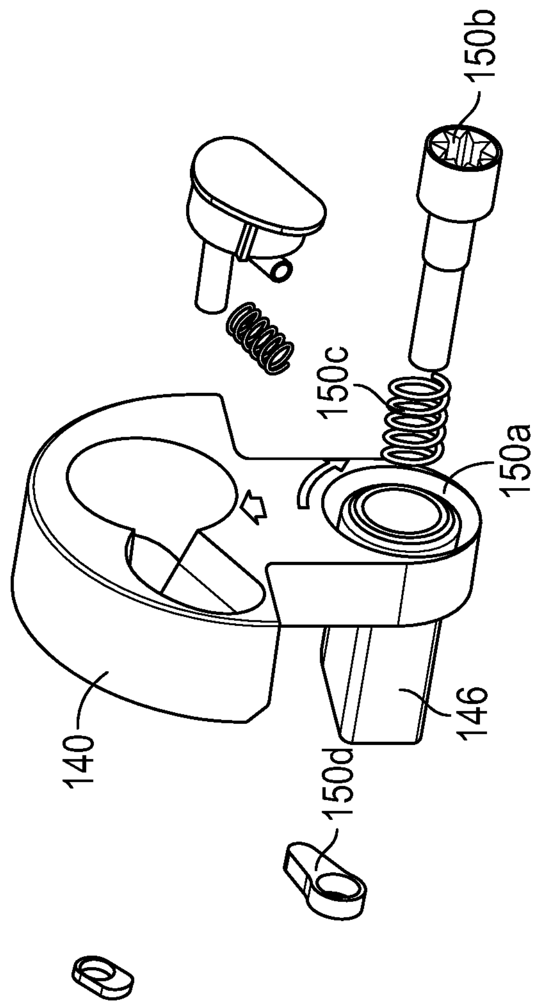
FIGS. 4A-4D depict an example modular superior fixation plate according to embodiments of the disclosure.
Figure 4A:
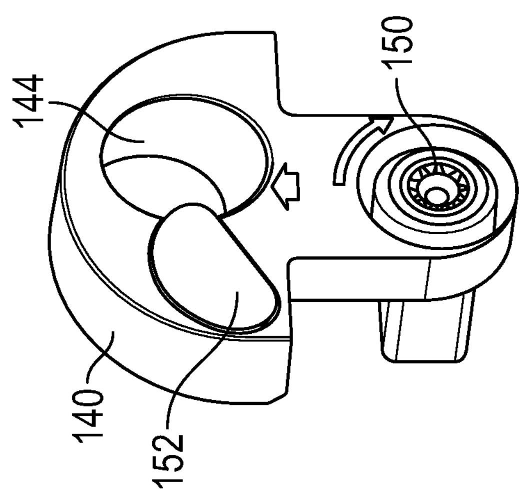
Figure 4D:
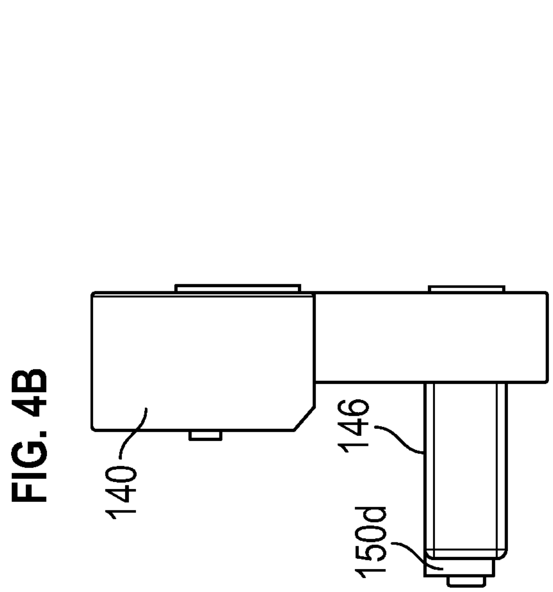
Figure 4C:
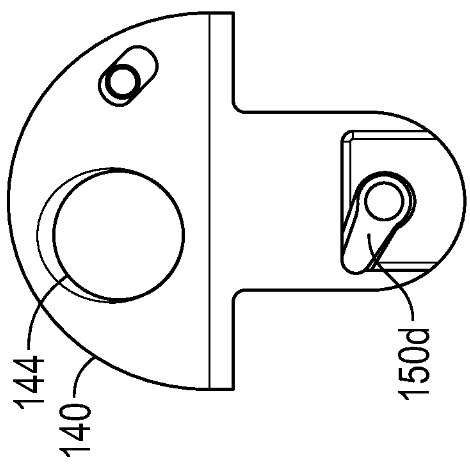
Figure 5A:
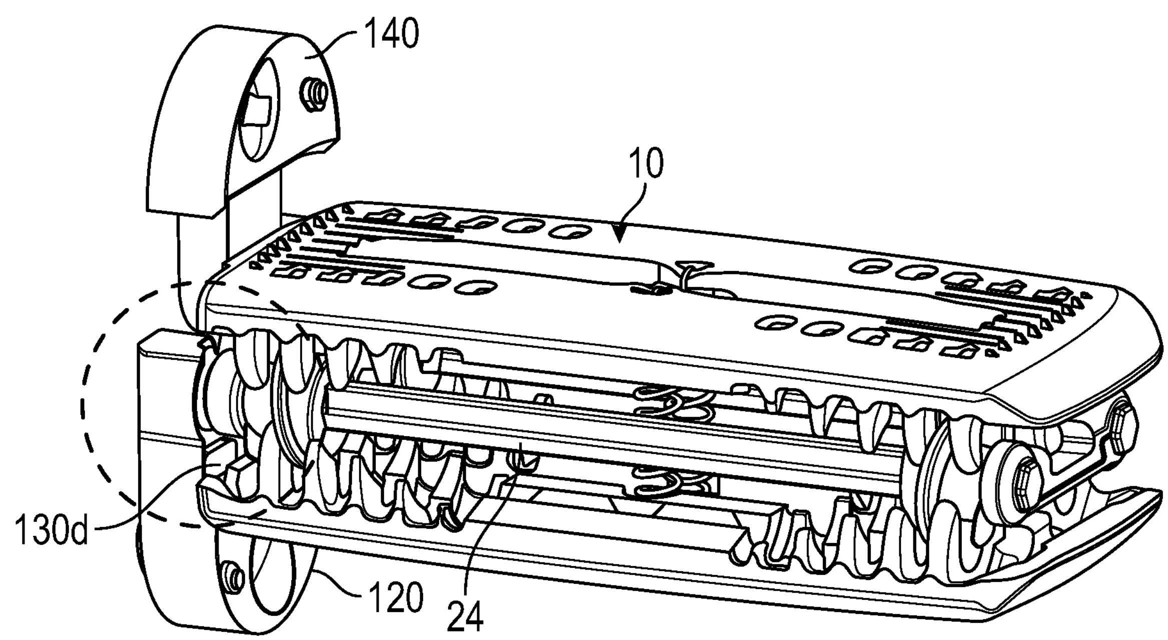
FIGS. 5A-5D show attachment of a modular inferior fixation plate to a dual-axis adjustable interbody fusion device in an unlocked state.
Figure 5B:
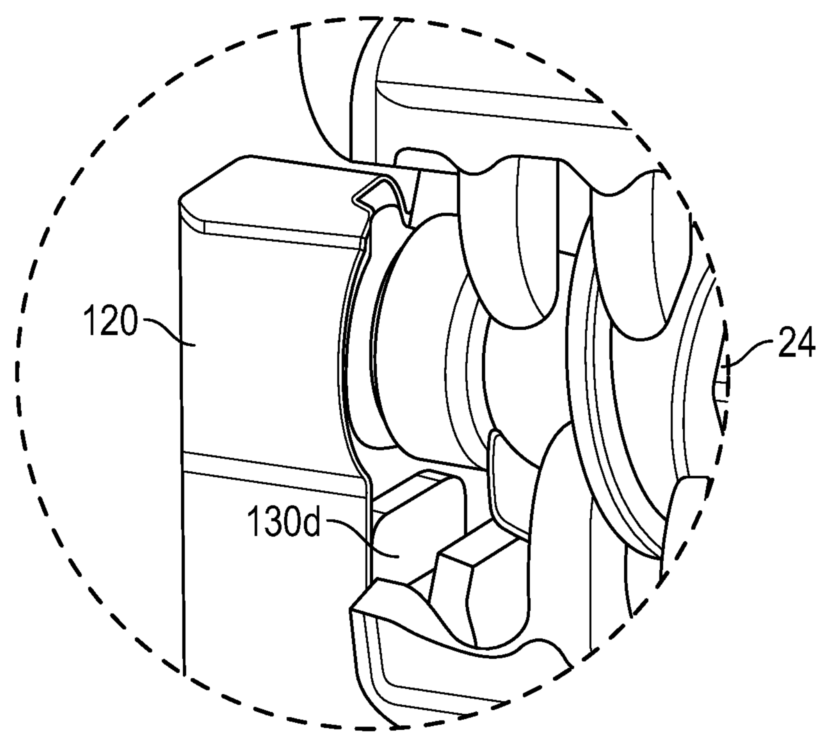
Figure 5C:
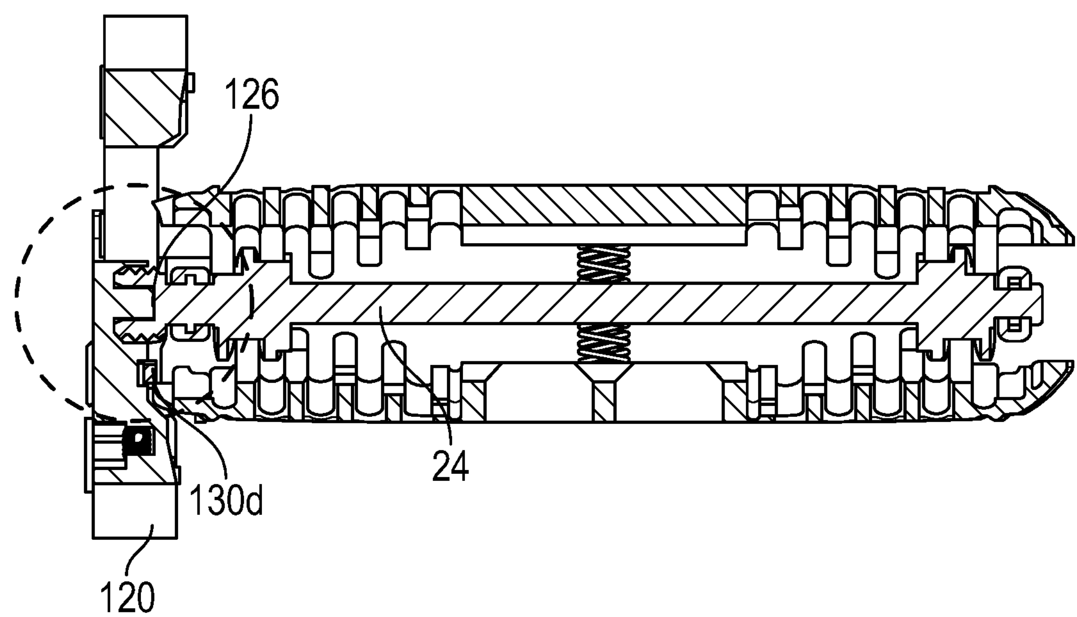
Figure 5D:
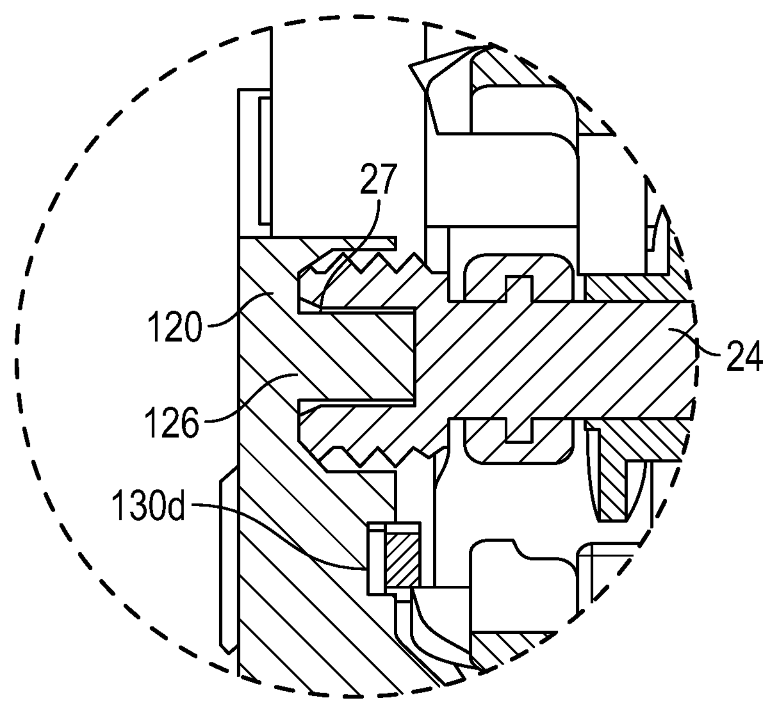

As shown in FIGS. 2A-2B, the apparatus 100 in general comprises an interbody fusion device 10 and a fixation assembly 110 including one or more modular fixation plates 120, 140 and spinal anchor components 122 and 142. The interbody fusion device 10 may be the same as, or similar to, the example dual-axis interbody fusion device 10 described above in conjunction with FIGS. 1A-1C. Alternatively, the interbody fusion device 10 can be any suitable dual-axis adjustable interbody fusion devices available from various manufacturers, which can be further adapted or modified for use with the fixation assembly 110.

Figure 10A:
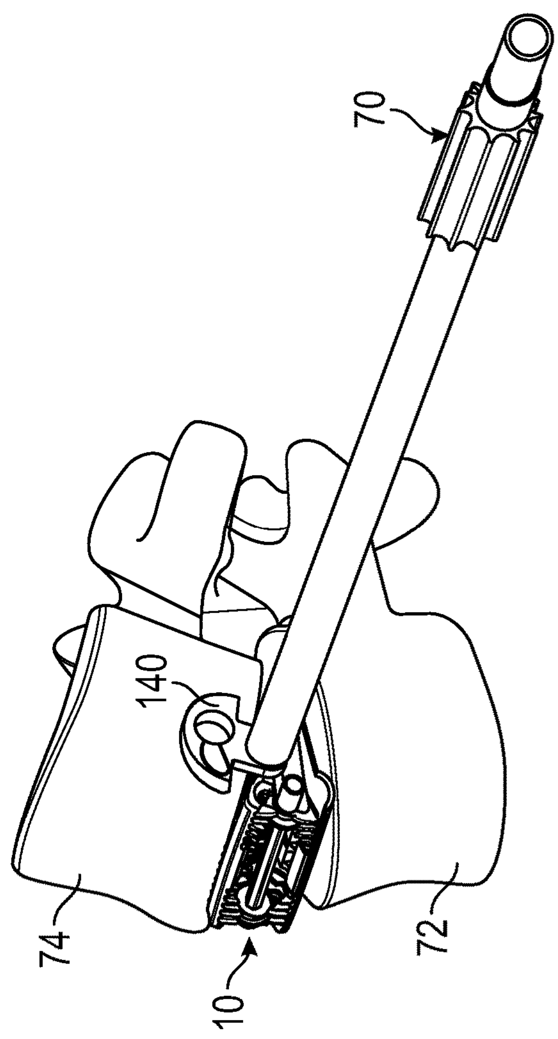
FIGS. 10A-10B depict attaching of modular fixation plates to a dual-axis adjustable interbody fusion device placed between adjacent vertebrae using an operation instrument.
Figure 10B:
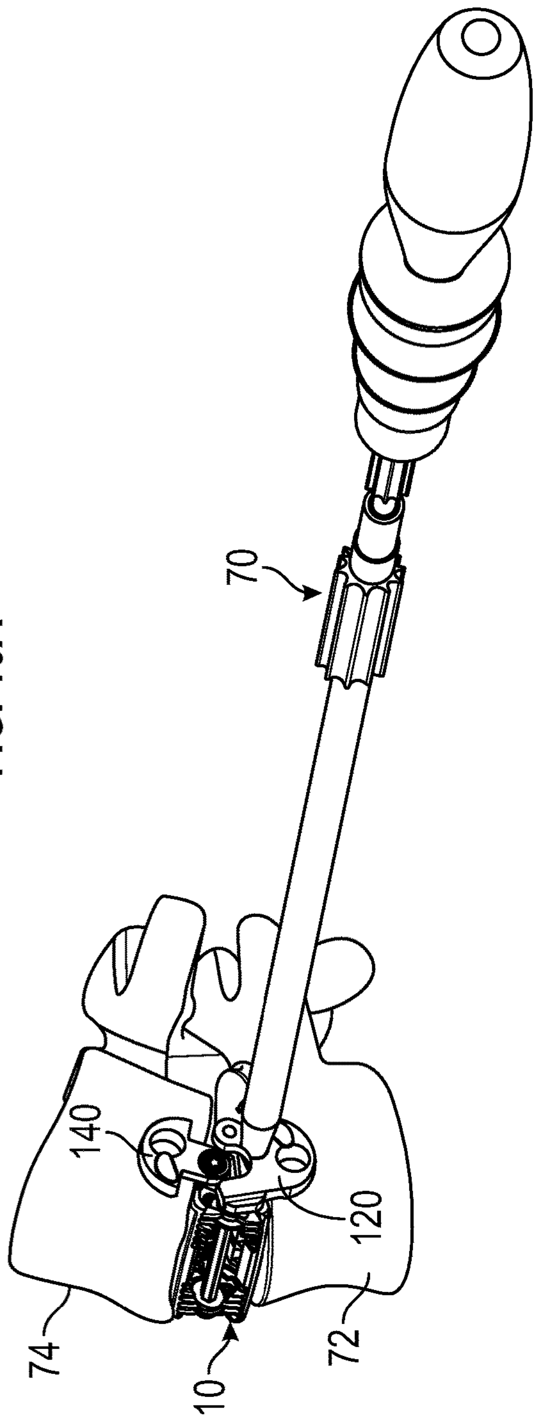

The fixation assembly 110 comprises at least a first or inferior fixation plate 120 and at least a first spinal anchor component or fastener 122. Additionally, or alternatively, the fixation assembly 110 comprises a second or superior fixation plate 140 and a second spinal anchor component or fastener 142. As used herein, the term "fixation plate" includes reference to a plate member or a plate assembly comprising a plate member and other parts or mechanisms assembled to the plate member. According to embodiments of the disclosure, the inferior fixation plate 120 is modular and configured to be attachable to the interbody fusion device 10. As used herein, the term "modular" refers to an embodiment of a fixation plate constructed as a unit and capable of being assembled to an interbody fusion device prior to or following implantation of the interbody fusion device. A modular fixation plate in a fixation assembly may be replaced by another modular fixation plate of a structure same as that of the one being replaced. The inferior fixation plate 120 may be provided with an aperture 124 configured for insertion of the first fastener 122 therethrough to a first or inferior vertebral body. Likewise, according to certain embodiments of the disclosure, the superior fixation plate 140 is modular and configured to be attachable to the interbody fusion device 10. The superior fixation plate 140 can be provided with an aperture 144 configured for insertion of the second fastener 142 therethrough to a second or superior vertebral body. Example fasteners or anchor components suitable for the first and/or second fasteners 122, 142 include but are not limited to spinal expansion head screws, spinal locking screws, spinal self-locking screws, spinal shaft screws, spinal nails, spinal barbs, spinal hooks, or other threaded or non-threaded members which can be anchored to a vertebral body. In an assembled view shown in FIG. 2B, the modular inferior fixation plate 120 and the superior fixation plate 140 are attached to the interbody fusion device 10 with the first and second fasteners 122, 142 being inserted through the apertures in the inferior and superior fixation plates 120, 140. It should be noted that in use, the modular inferior and superior fixation plates 120, 140 can be attached to the interbody fusion device 10 in situ, or after the interbody fusion device 10 is placed between adjacent vertebral bodies and adjusted to a desired configuration. The modular inferior and superior fixation plates 120, 140 may also be attached to the interbody fusion device 10 prior to implantation of the interbody fusion device if desired. FIGS. 10A-10B, which will be described in greater detail below, show that a modular superior fixation plate 140 and a modular inferior fixation plate 120 are attached to an interbody fusion device 10 with an operation instrument 70 after the interbody fusion device 10 has been placed, expanded, and/or lordotically adjusted to a proper configuration between adjacent vertebrae.

With reference to FIGS. 3A-3D, the modular inferior fixation plate 120 can be configured to be attachable to the interbody fusion device 10 serving to stabilize and prevent migration of the interbody fusion device 10 in adjacent vertebrae. According to certain embodiments of the disclosure, the modular inferior fixation plate 120 may be provided with geometry features configured for attachment to the interbody fusion device 10 to prevent unwanted rotation of a drive shaft e.g. the posterior drive shaft 24 of the interbody fusion device 10. For instance, the inferior fixation plate 140 may include a male geometry 126 (FIG. 3C) configured to be inserted into the female geometry 27 in the end portion of the posterior drive shaft 24 of the interbody fusion device 10. By way of example, the male geometry 126 in the inferior fixation plate 120 may have a male hexalobe feature which can be tightly mated into a female hexalobe feature 27 in the end portion of the posterior drive shaft 24 to prevent unwanted rotation of the drive shaft. A circular groove 127 around the male geometry 126 may be provided to accommodate the end portion of the posterior drive shaft 24. FIGS. 5A-5D and 6A-6D, which will be described in greater detail below, show the attachment of the inferior fixation plate 120 to the interbody fusion device 10, where the male geometry 126 in the inferior fixation plate 120 is tightly mated into the female geometry 27 in the end portion of the posterior drive shaft 24.

With reference to FIGS. 3A-3D, the inferior fixation plate 120 may be provided with geometry features allowing for pivoting of the inferior fixation plate 120 relative to the interbody fusion device 10 before the male geometry 126 in the inferior fixation plate 120 is mated into the female geometry 27 in the end portion of the posterior drive shaft 24 of the interbody fusion device 10. For instance, the inferior fixation plate 120 may include a channel geometry 128 configured to accommodate e.g. the end portion of the anterior drive shaft 26 of the interbody fusion device 10. The channel geometry 128 allows the inferior fixation plate 120 to "pivot" about the posterior drive shaft 24 without interfering with the anterior drive shaft 26, by accommodating the end portion of the anterior drive shaft 26 in the channel geometry 128. The ability for the inferior fixation plate 120 to pivot allows the position of the aperture 124 in the inferior fixation plate 120 to be adjusted e.g. according to the expanded and/or lordotically adjusted configuration of the interbody fusion device 10, thereby providing an optimal position of the aperture relative to the vertebral body for the fastener. FIGS. 7A-7D shows the channel geometry 128 in the inferior fixation plate 120 as attached to the interbody fusion device 10. The channel geometry 128 extends from a first end 129*a* to a second end 129*b*, allowing the inferior fixation plate 120 to "pivot" about the posterior drive shaft 24 by accommodating the end portion of the anterior drive shaft 26 in the channel 128 e.g. at the first end 129*a* when the interbody fusion device 10 is in an expanded but a non-lordotically adjusted configuration (FIGS. 7A-7B), or at the second end 129*b* when the interbody fusion device 10 is in a hyperlordotically adjusted configuration (FIGS. 7C-7D), or at any position therebetween when the interbody fusion device 10 is in a configuration between a non-lordotically adjusted configuration and hyperlordotically adjusted configuration.

Figure 6A:
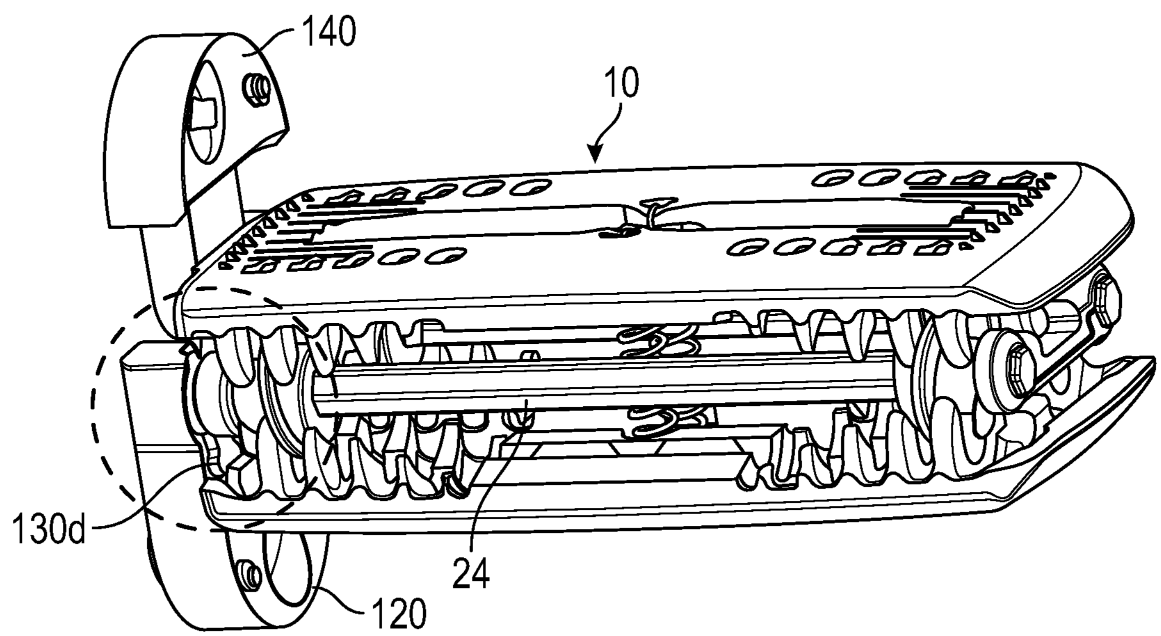
FIGS. 6A-6D show attachment of a modular inferior fixation plate to a dual-axis adjustable interbody fusion device in a locked state.
Figure 6B:
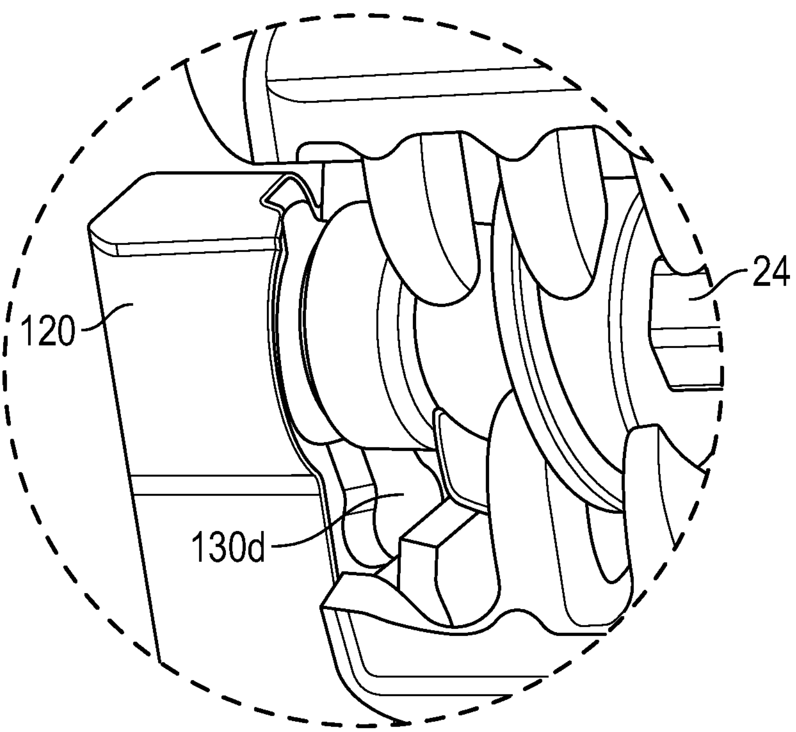
Figure 6C:
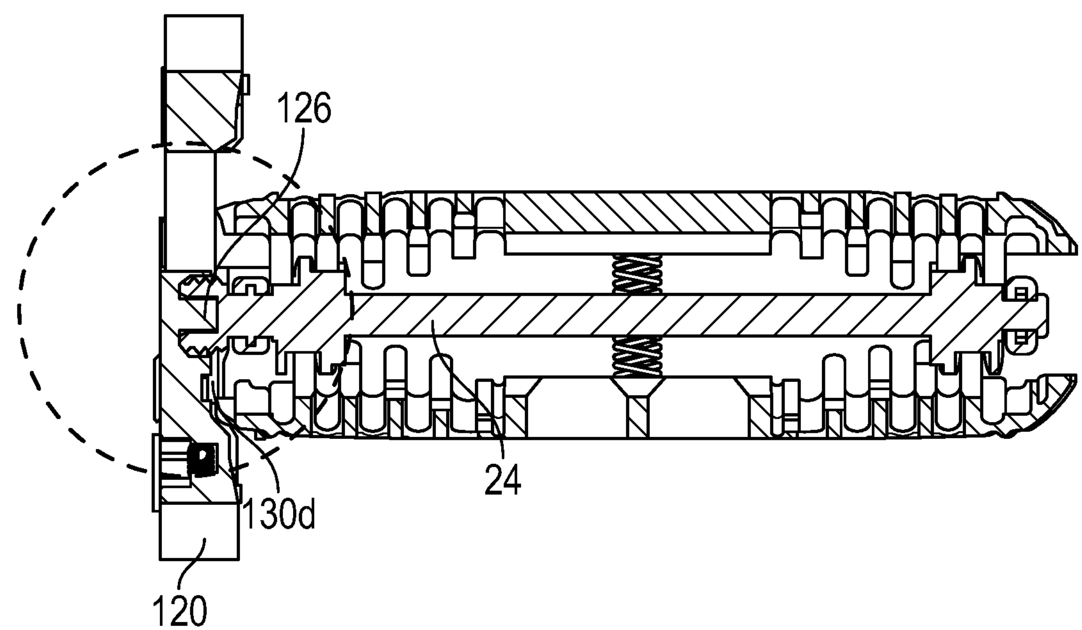
Figure 6D:
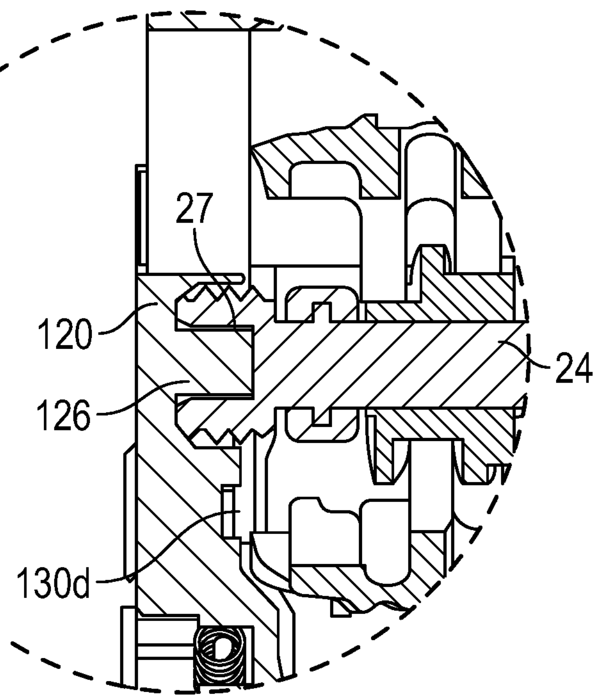
Figure 7B:
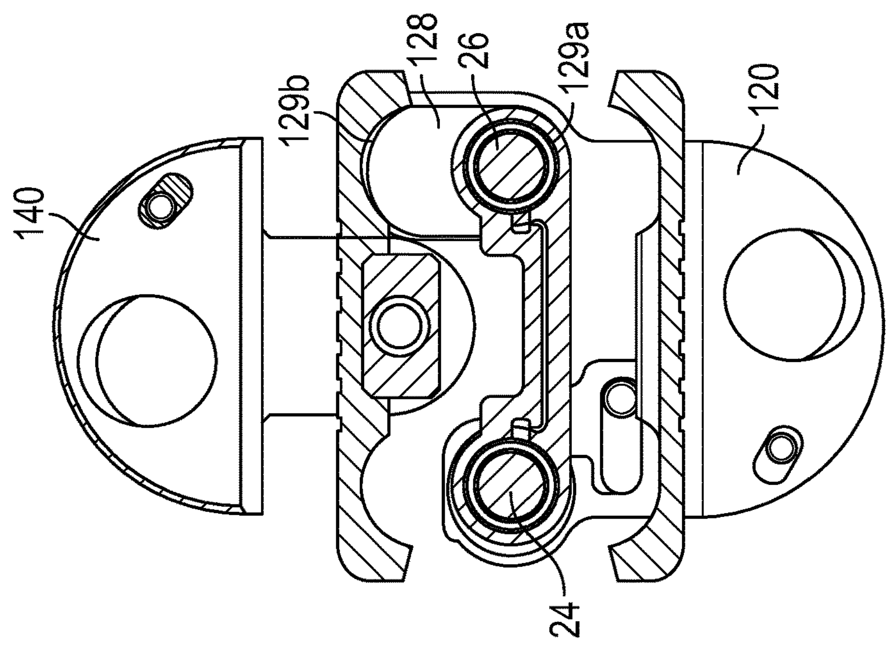
FIGS. 7A-7D depict a channel geometry in a modular inferior fixation plate according to embodiments of the disclosure.
Figure 7A:
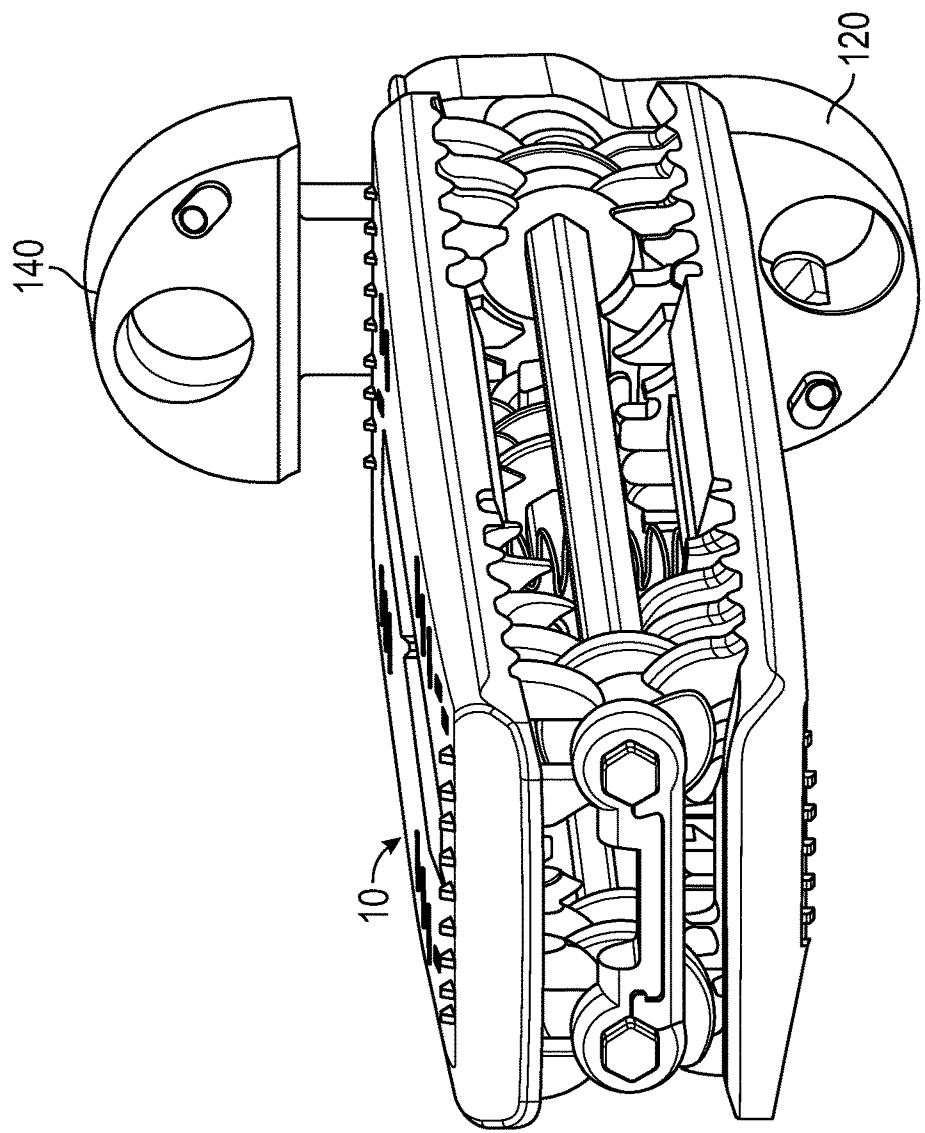
Figure 7D:
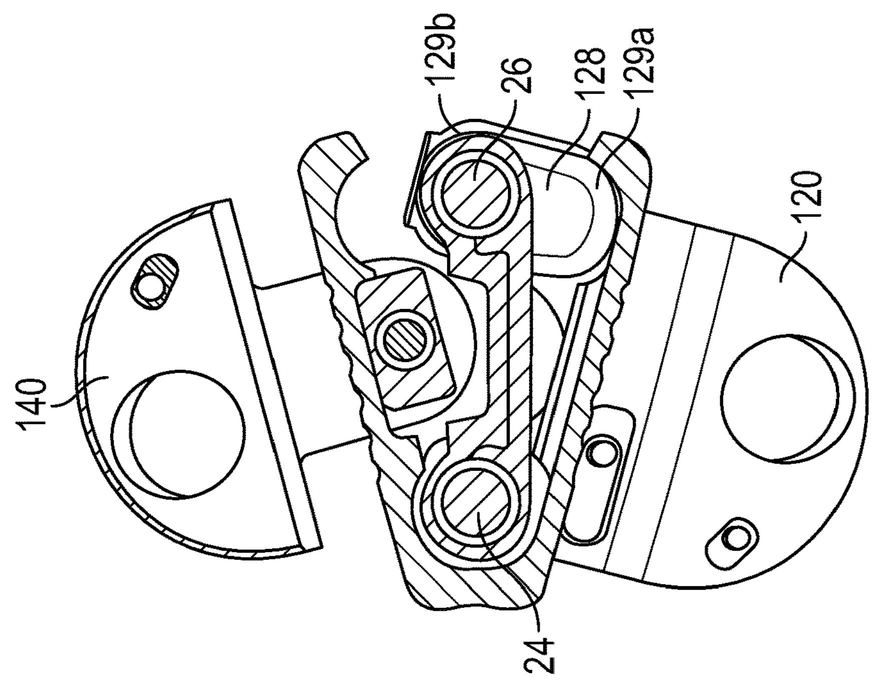
Figure 7C:
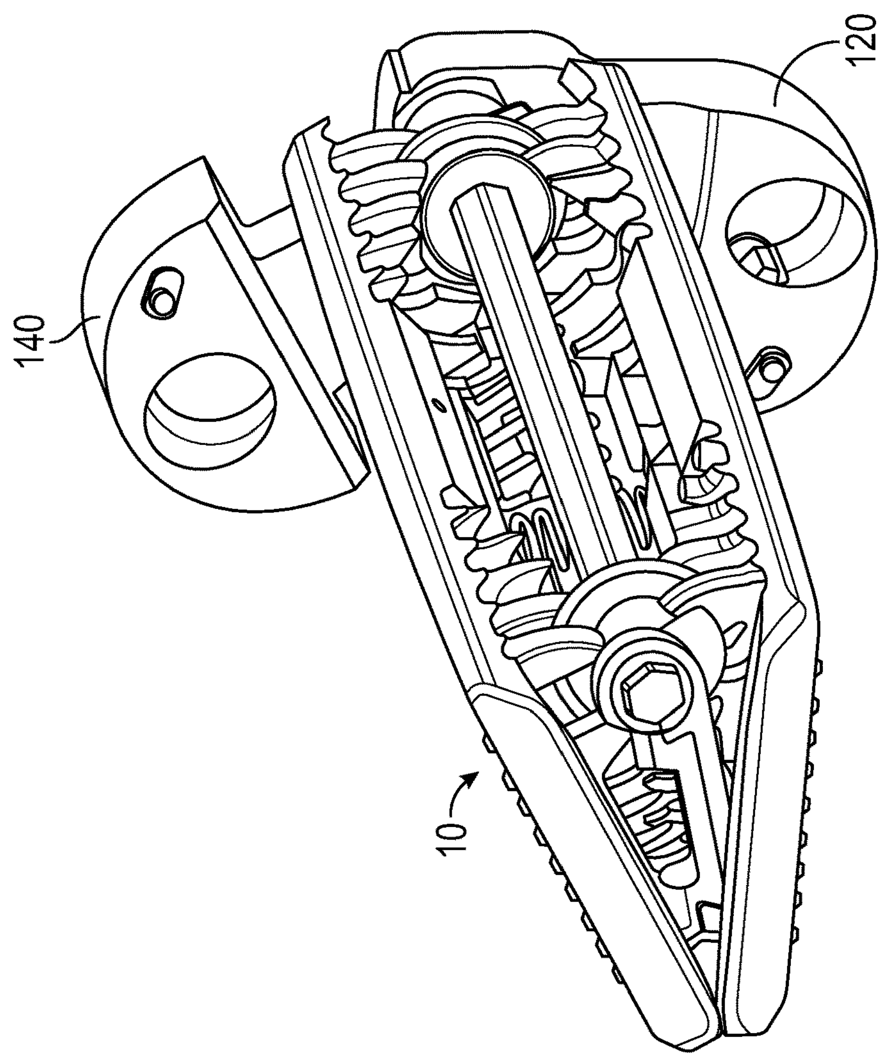

With reference to FIGS. 3A-3D, the inferior fixation plate 120 may include an attachment-lock mechanism 130 engageable to lock the interbody fusion device 10 to secure the attachment of the the inferior fixation plate 120 to the interbody fusion device 10. According to certain embodiment of the disclosure, the attachment-lock mechanism 130 may include a lock housing 130*a*, a rod 130*b*, a compression spring 130*c* loaded on the rod 130*b* and retained in the lock housing 130*a*, and a latch 130*d* coupled to a distal end portion of the rod 130*b*. The proximal end portion of the rod 130*b* may have features for receiving a driving tool to actuate the attachment-lock mechanism 130. For example, the proximal end portion of the rod 130*b* may be provided with a female hexalobe feature for receiving a torx driver. In use, the user may press the rod 130*b* with a driver to displace the latch 130*d* coupled to the distal end portion of the rod 130*b* to allow the latch 130*d* to rotate and hook to a component in the interbody fusion device 10. The compression spring 130*c* loaded on the rod 130*b* apply a force to the latch 130*d*, and upon release of the driver, the latch 130*d* tightens the attachment of the inferior fixation plate 120 to the interbody fusion device 10, or locks the interbody fusion device 10 to the inferior fixation plate 120. The lock housing 130*a* may be provided with features such as a thread configured for connecting with an operation instrument. FIGS. 5A-5D show the latch 130*d* of the attachment-lock mechanism 130 in an unlocked state. FIGS. 6A-6C show the latch 130*d* of the attachment-lock mechanism 130 in a locked state wherein the latch 130*d* interferes or hold in place the external thread in the end portion of the posterior drive shaft 24, preventing the posterior drive shaft 24 from unwanted rotation.

Figure 15B:
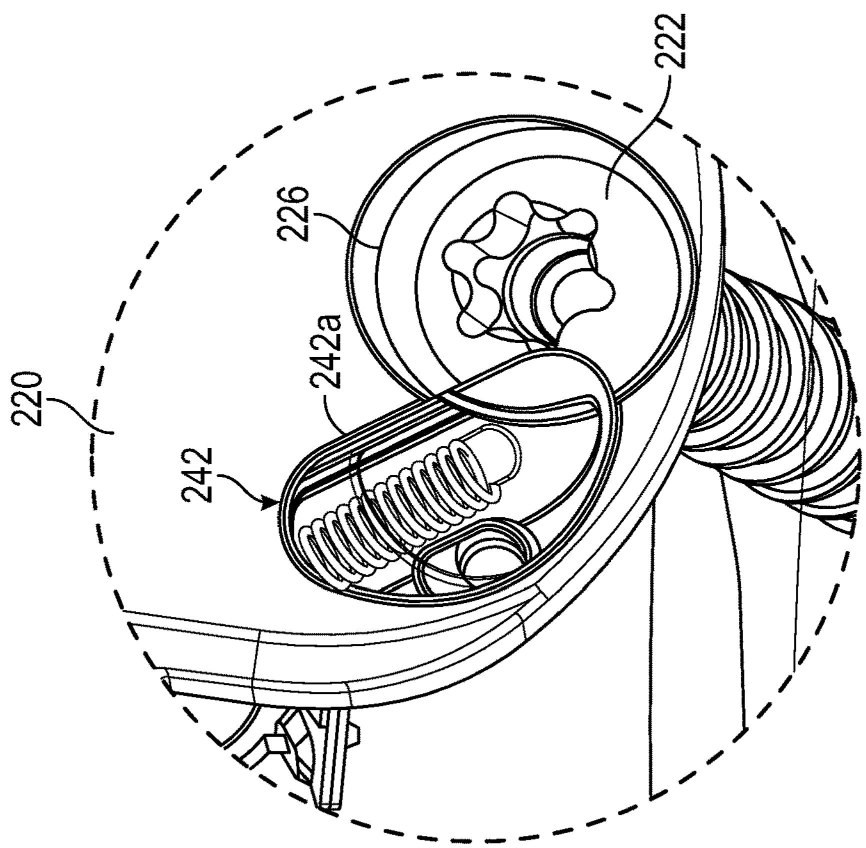
FIGS. 15A-15B show a transparent view of a fastener-lock mechanism as part of a fixation plate according to embodiments of the disclosure.
Figure 15A:
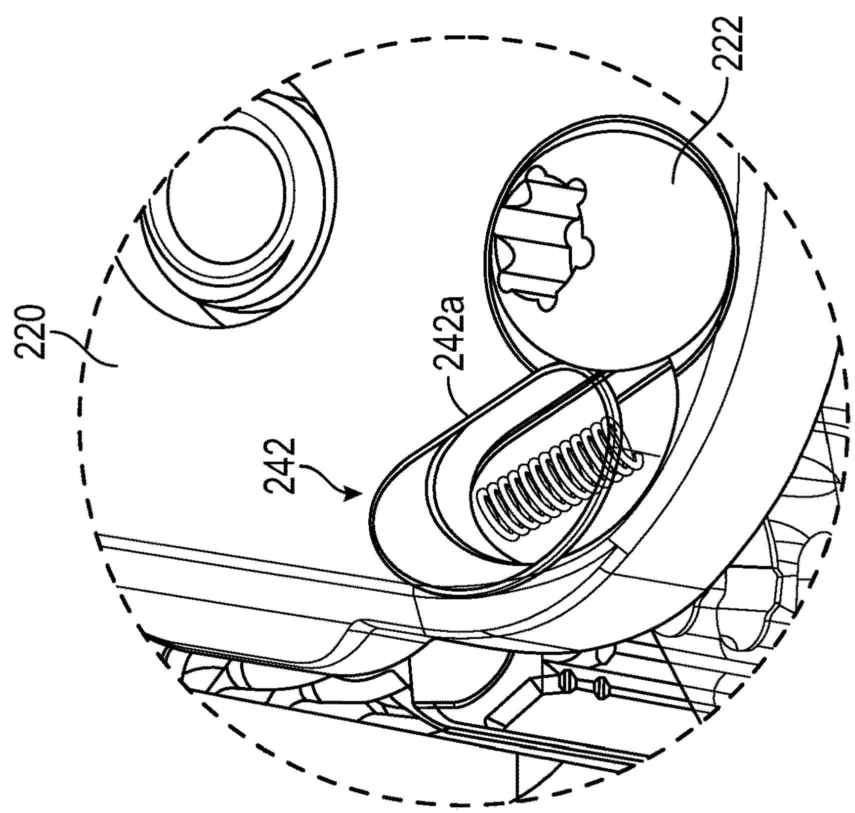

With reference still to FIGS. 3A-3D, the inferior fixation plate 120 may include a fastener-lock mechanism 132 configured to prevent the first fastener 122 from backing out of the aperture 124 after being fastened. According to certain embodiments of the disclosure, the fastener-lock mechanism 132 may comprise a lock component 132*a* received in a recess 132*b* adjacent to the fastener aperture 124 in the inferior fixation plate 120, a compression spring 132*c* loaded on a part of the lock component 132*a*, and a retainer 132*d* connected to a part of the lock component 132*a*. The retainer 132*d* retains the lock component 132*a* in the recess 132*b* via a compression spring loaded on the lock component 132*a* and is slidable with the lock rod 132*a* relative to the inferior fixation plate 120. The fastener-lock mechanism 132 has a locked state when the compression spring 132*c* is in a free or extended state allowing the lock component 132*a* to extend partially over the aperture 124 in the inferior fixation plate 120, and an unlocked state when the compression spring 132*c* is in a compressed state forcing the lock component 132*a* away from the aperture 124 in the inferior fixation plate 120. In use, when a fastener 122 is inserted into the aperture 124, the spring-loaded lock component 132*a* is forced away from the aperture 124, allowing the the fastener 122 to be driven e.g. screwed into a vertebral body. Once the fastener 122 is driven all the way and the head of the fastener 122 is received in the countersink of the aperture 124 and flushed with or below the surface of the fixation plate 120, the spring-loaded lock component 132*a* springs back at least partially over the fastener head, preventing the fastener 122 from backing out. The fastener-lock mechanism 132 allows for "zero step" locking because the surgeon does not need any extra instrument or step to engage the fastener-lock mechanism 132 in order to cover the fastener head to keep them from backing out. With greater clarity, FIGS. 15A-15B show an example fastener-lock mechanism 242 in a fixation plate 220 to be described below. The fastener-lock mechanism 132 in the inferior fixation plate 120 can be the same as or similar to the fastener-lock mechanism 242 in a fixation plate 220 shown in FIGS. 15A-15B. Alternatively, the fastener-lock mechanism 132 in the inferior fixation plate 120 can be the same as or similar to the fastener-lock mechanism 446 to be described in conjunction with FIGS. 27A-27B.

Figure 8B:
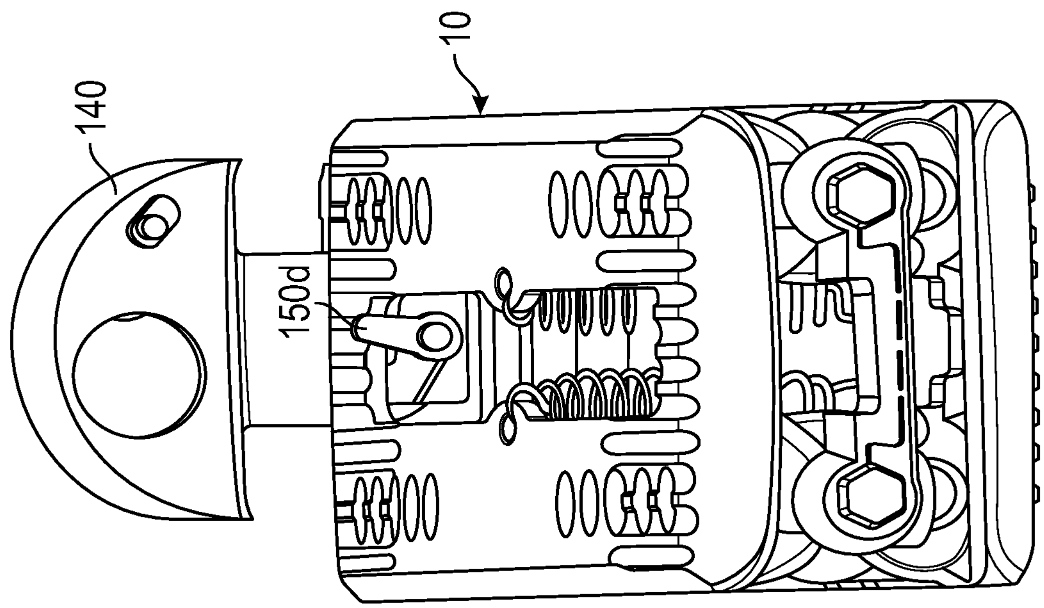
Figure 8A:
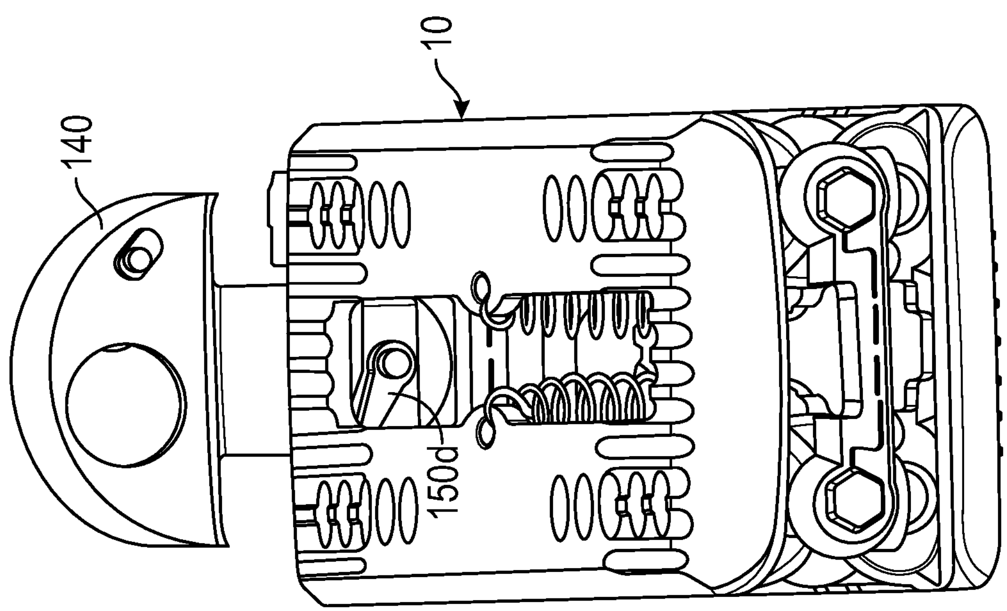

With reference now to FIGS. 4A-4D, the modular superior fixation plate 140 can be configured to be attachable to the interbody fusion device 10 serving to stabilize and prevent migration of the interbody fusion device placed 10 in adjacent vertebrae. According to certain embodiments of the disclosure, the modular superior fixation plate 140 may include a protruding portion 146 configured to be insertable into the interbody fusion device 10. The protruding portion 146 may have a geometry configured to tightly mate with an internal component(s) of the interbody fusion device 10 to restrict unwanted movement of the interbody fusion device 10. By way of example, the protruding portion 146 may have a geometry generally in the shape of a rectangular prism, which can be placed tightly in or between a channel in the inner surface of the superior shell member 34. As such, translational movement of the interbody fusion device 10 relative to the superior fixation plate 140 in lateral, posterior, and/or anterior direction can be prohibited or minimized. The protruding portion 146 may also in any other suitable shapes or forms. FIGS. 8A-8B show the superior fixation plate 140 inserted in the interbody fusion device 10.

With reference to FIGS. 4A-4D, the superior fixation plate 140 may include an attachment-lock mechanism 150 engageable to secure the attachment of the superior fixation plate 140 to the interbody fusion device 10 or lock the interbody fusion device 10. The attachment-lock mechanism 150 of the superior fixation plate 140 is the same as or similar to the attachment-lock mechanism 130 of the inferior fixation plate 120 in many aspects. For completeness of description, the attachment-lock mechanism 150 of the superior fixation plate 140 may include a lock housing 150*a*, a rod 150*b*, a compression spring 150*c* loaded on the rod 150*b* and retained in the lock housing 150*a*, and a latch 150*d* coupled to a distal end portion of the rod 150*b*. FIG. 8A shows the attachment-lock mechanism 150 in an unlocked state, with the superior fixation plate 140 being inserted in the interbody fusion device 10. FIG. 8B shows the attachment-lock mechanism 150 in a locked state, with the superior fixation plate 140 being inserted in the interbody fusion device 10 and locked.

With reference still to FIGS. 4A-4D, the superior fixation plate 140 may further include a fastener-lock mechanism 152 configured to prohibit the second fastener 142 from backing out of the aperture 144 in the superior fixation plate 140. The faster-lock mechanism 152 of the superior fixation plate 140 is the same as or similar to the fastener-lock mechanism 132 of the inferior fixation plate 120 in many aspects and its detail description is omitted herein.

Figure 9A:
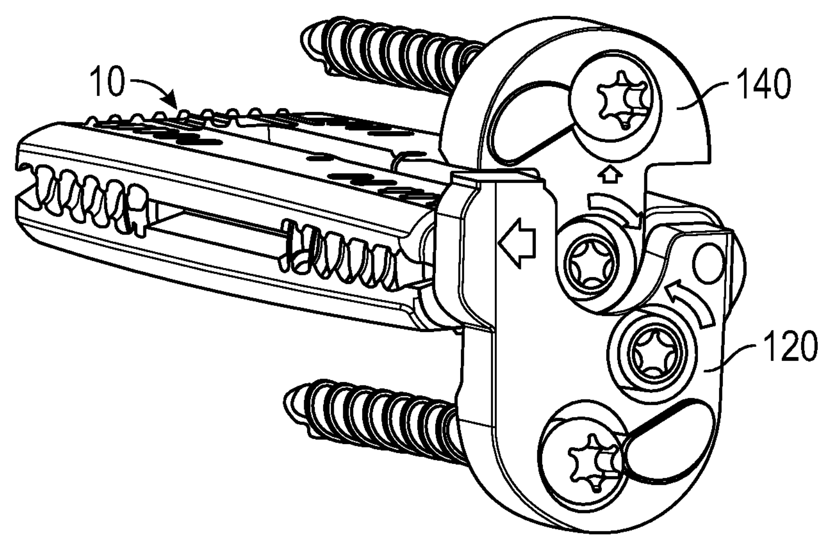
FIGS. 9A-9C show attachment of a modular inferior fixation plate and a modular superior fixation plate to a dual-axis adjustable interbody fusion device in a contracted, an expanded, and a lordotically adjusted configuration, respectively.
Figure 9B:
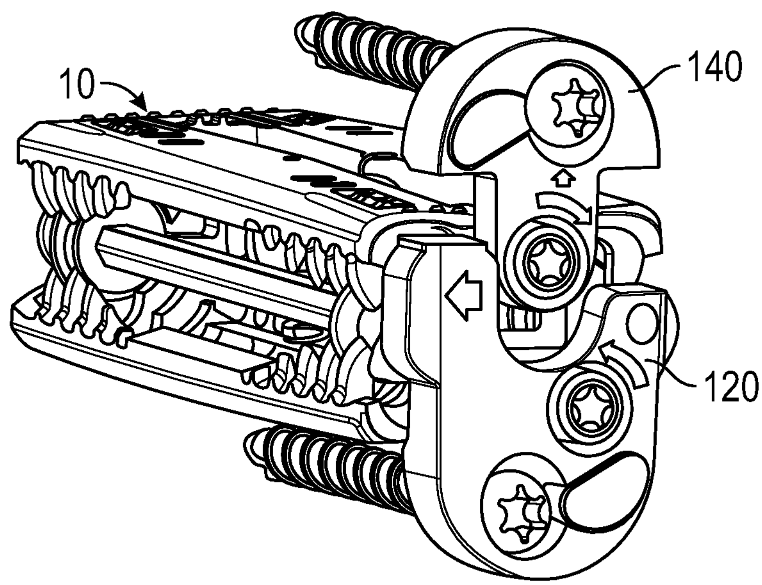
Figure 9C:
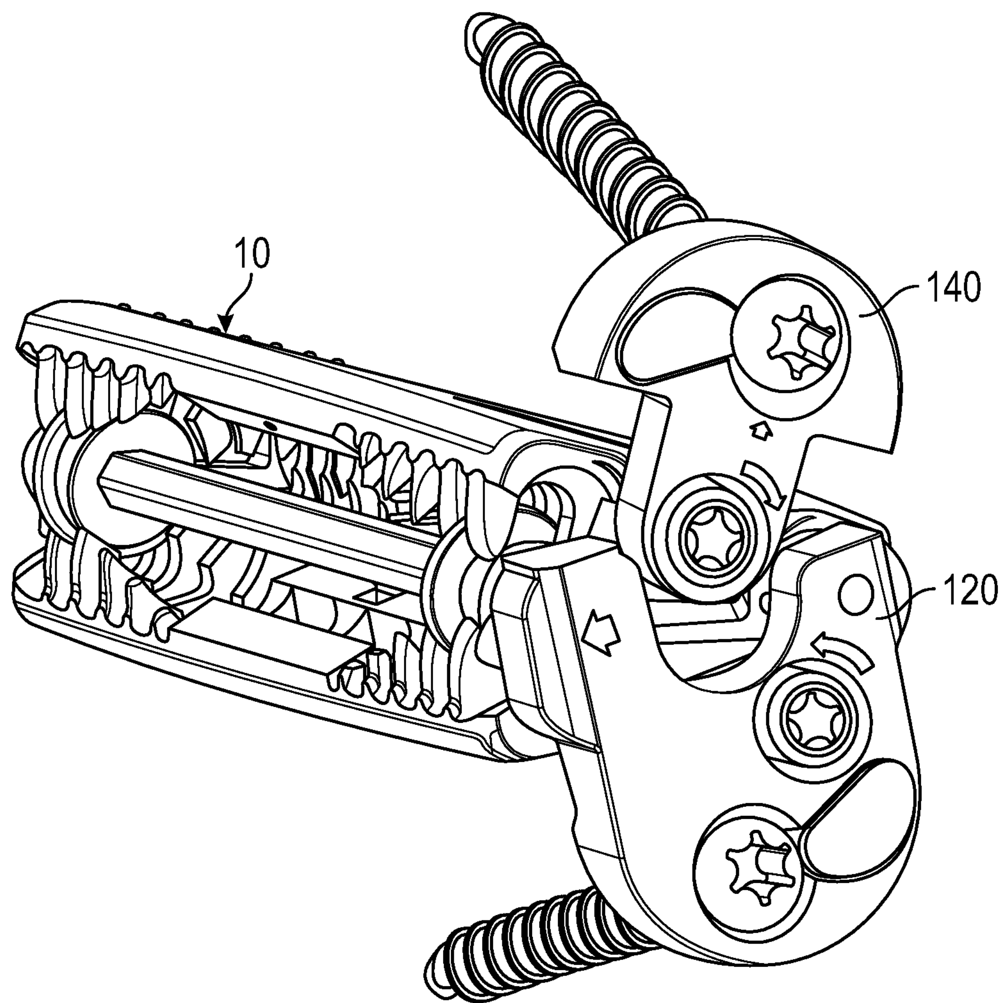

Returning to FIG. 2A-2B, the modular inferior and superior fixation plates 120, 140 may be shaped and/or sized or configured to allow the two fixation plates to at least partially intermesh when being attached to the interbody fusion device 10. By way of example, the inferior fixation plate 120 may comprise an edge portion having a concave profile 121, the superior fixation plate 140 may comprise an edge portion having a convex profile 141. The concave edge portion 121 of the inferior fixation plate 120 and the convex edge portion 141 of the superior fixation plate 140 allows for at least partial intermeshing, thereby allowing attachment of the inferior fixation plate 120 and the superior fixation plate 140 to the interbody fusion device 10 when the interbody fusion device 10 is in a contracted configuration or an expanded configuration of a lesser degree. The rounded or scalloped profile of the concave edge portion 121 of the inferior fixation plate 120 and the convex edge portion 141 of the superior fixation plate 140 also allow attachment of the inferior and superior fixation plates 120, 140 to the interbody fusion device 10 when the interbody fusion device 10 is in a lordotically or hyperlordotically adjusted configuration (e.g. 20 to 30 degrees of lordosis). FIGS. 9A-9C show attachment of the inferior and superior fixation plates 120, 140 and fasteners 122, 142 to an interbody fusion device 10 in a contracted, a fully expanded, and a lordotically adjusted configuration respectively. For ease of description and illustration, the dimensions set forth below refer to embodiments where the dual-axis adjustable interbody fusion device 10 is placed between adjacent vertebrae via a lateral lumbar interbody fusion (LLIF) procedure, expanded and/or lordotically adjusted by operating the two driving mechanisms along the anterior and/or posterior side of the patient respectively to achieve a configuration suitable for a sagittal balance for the patient. It will be appreciated by one of ordinary skill in the art that the interbody fusion device can be placed via an anterior lumbar interbody fusion (ALIF) or posterior lumbar interbody fusion (PLIF) procedure, and is expanded or lordotically adjusted by operating the driving mechanisms along the lateral and/or contra-lateral side respectively to achieve a desired coronal balance or correct coronal imbalance for the patient.

FIG. 9A shows an embodiment where the interbody fusion device 10 is contracted to a configuration having a height at the anterior side ("anterior height") of 8.4 mm, a height at the posterior height ("posterior height") of 8.4 mm, and an angle between the superior and inferior shell members ("lordosis") of 0 degree. The concave and convex profile of the edge portions allow the modular inferior and superior fixation plates 120, 140 to be inserted and attached to the interbody fusion device 10 respectively. FIG. 9B shows an embodiment where the interbody fusion device 10 is in a fully expanded configuration having an anterior height of 16.1 mm, a posterior height of 16.1 mm, and a lordosis of 0 degree. The modular inferior and superior fixation plates 120, 140 attached to the interbody fusion device can stabilize and prevents the interbody fusion device 10 in a fully expanded configuration from migration. FIG. 9C shows an embodiment where the interbody fusion device 10 is in a hyperlordotically adjusted configuration having an anterior height of 17.1 mm, a posterior height of 7.2 mm, and a lordosis of 30 degree. The modular inferior and superior fixation plates 120, 140 attached to the interbody fusion device 10 can stabilize and prevent the interbody fusion device in a hyperlordotically adjusted configuration from migration. In comparison of FIG. 9C with FIG. 9B, the channel geometry in the inferior fixation plate 120 allows the inferior fixation plate 120 to be "pivoted" around the posterior drive shaft 24 before final attachment (notice the different position of the anterior drive shaft 26 in the channel geometry in the inferior fixation plate 120), thereby allowing angulation of the inferior fixation plate 120 relative to the interbody fusion device 10, providing an optimal position of the aperture in the inferior fixation plate 120 and thus an optimal fastener trajectory. Further, the apertures in the inferior and superior fixation plates 120, 140 can be configured or machined such that the axis of the apertures can angle from the inferior and superior fixation plates respectively, as will be described in more detail in conjunction with FIGS. 16A-16B. The angled apertures in the inferior and superior fixation plates 120, 140 and selections of fasteners (e.g. rounded head portion of the fasteners) allow the fasteners 122, 142 to have variable trajectories e.g. from 0 to 15 degrees in the caudal and cephalad directions, as shown in FIGS. 9A-9C respectively. It should be noted that the specific dimensions and degrees provided above are for thorough understanding of various embodiments of the disclosure but not intended to limit the scope of the claims.

The dual-axis adjustable interbody fusion device with modular fixation or apparatus 100 can be used in treatment of various spinal diseases, including but not limited to degenerative disc disease (DDD), spondylolisthesis, retrolisthesis (Grade 1), and so on. As shown in FIGS. 10A-10B, in use the modular inferior and superior fixation plates 120, 140 can be inserted and attached to an interbody fusion device 10 in situ. For instance, an interbody fusion device 10 in a contracted configuration can be first inserted and placed between adjacent vertebrae 72, 74 using an operation instrument 70 via a suitable surgical procedure. Suitable surgical procedure for placing the interbody fusion device 10 include a lateral lumbar interbody fusion (LLIF) procedure, an anterior lumbar interbody fusion (ALIF), posterior lumbar interbody fusion (PLIF) procedure, and any other suitable surgical procedures performed in the lumbar or other regions of the spinal column. Various suitable operation instruments are described in U.S. application Ser. No. 15/661,435 filed Jul. 17, 2017 entitled "Surgical Operating Instrument for Expandable and Adjustable Lordosis Interbody Fusion Systems" and U.S. application Ser. No. 16/035,637 filed Jul. 15, 2018 entitled "Surgical Operating Instrument for Expandable and Adjustable Lordosis Interbody Fusion Systems," the disclosures of all of which are incorporated herein in their entirety. The interbody fusion device 10 can be expanded and/or lordotically adjusted using the operation instrument 70, forming a suitable configuration between the adjacent vertebrae 72, 74. By way of example, the operation instrument 70 can connect the interbody fusion device 10 via the external threads 25 on the end portions of the posterior and anterior drive shafts 24, 26, and expand or lordotically adjust the interbody fusion device 10 by engaging the female features 27 in the end portions of the posterior and anterior drive shafts 24, 26 (FIG. 1A).

Then, a modular superior fixation plate 140 can be introduced to the target area and attached to the interbody fusion device 10 through the same surgical approach for placing the interbody fusion device 10. According to embodiments of the disclosure, operation instrument 70 used for placing and operating the interbody fusion device 10 can be used for inserting and attaching the modular superior fixation plate 140. For instance, the surgeon can connect the superior fixation plate 140 with the operation instrument 70 via the thread provided at the lock housing 150*a* of attachment-lock mechanism 150 (FIGS. 4A-4D), introduce the superior fixation plate 140 to the target area through the same surgical approach, insert the protruding portion of the superior fixation plate 140 into the interbody fusion device 10. The interbody fusion device 10 can be locked to superior fixation plate 140 using the operation instrument 70 by actuating the attachment-lock mechanism 150.

After or before inserting and attaching the modular superior fixation plate 140, a modular inferior fixation plate 120 can be introduced to the target area and attached to the interbody fusion device 10 using the same operation instrument 70 through the same surgical approach for placing the interbody fusion device 10. For instance, the surgeon can connect the inferior fixation plate 120 with the operation instrument 70 via the thread provided at the lock housing 130*a* of lock-attachment mechanism 130 (FIGS. 3A-3D), introduce the inferior fixation plate 120 to the target area through the same surgical approach, insert the male geometry 126 in the inferior fixation plate 120 into the female geometry 27 in the end portion of the posterior drive shaft 24. Optionally, before final engagement of the male geometry 126 of inferior fixation plate 120 with the female geometry 27 of the posterior drive shaft 24, the inferior fixation plate 120 can be pivoted about the posterior drive shaft 24 to adjust or provide an optimal position of the aperture 124 in the inferior fixation plate 120 for an optima fastener trajectory. The the interbody fusion device 10 can be then further locked to the inferior fixation plate 120 using the operation instrument 70 by actuating the attachment-lock mechanism 130.

Figure 11B:
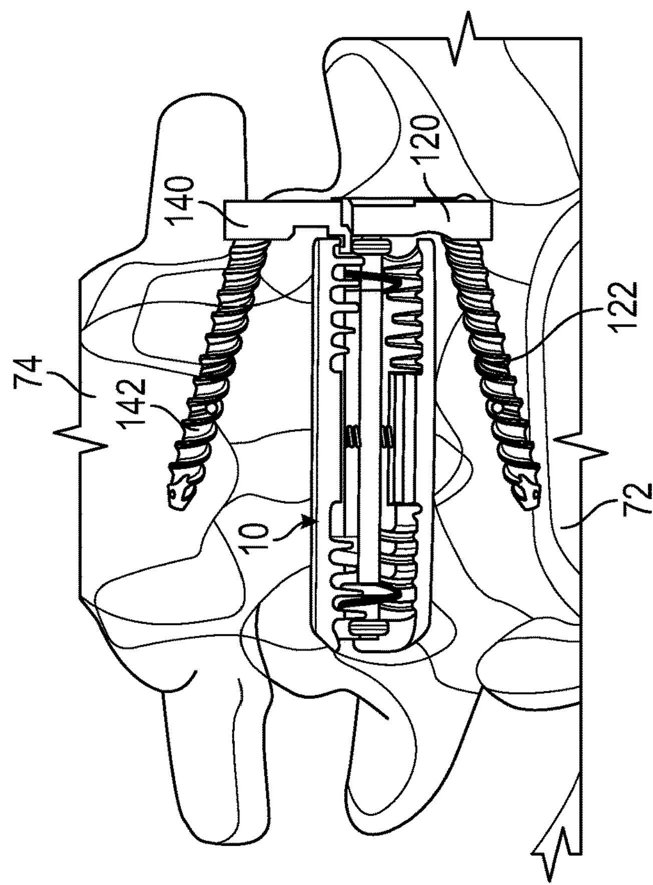
FIGS. 11A-11B depict a dual-axis adjustable interbody fusion device secured by an inferior fixation plate and a superior fixation plate to adjacent vertebral bodies.
Figure 11A:
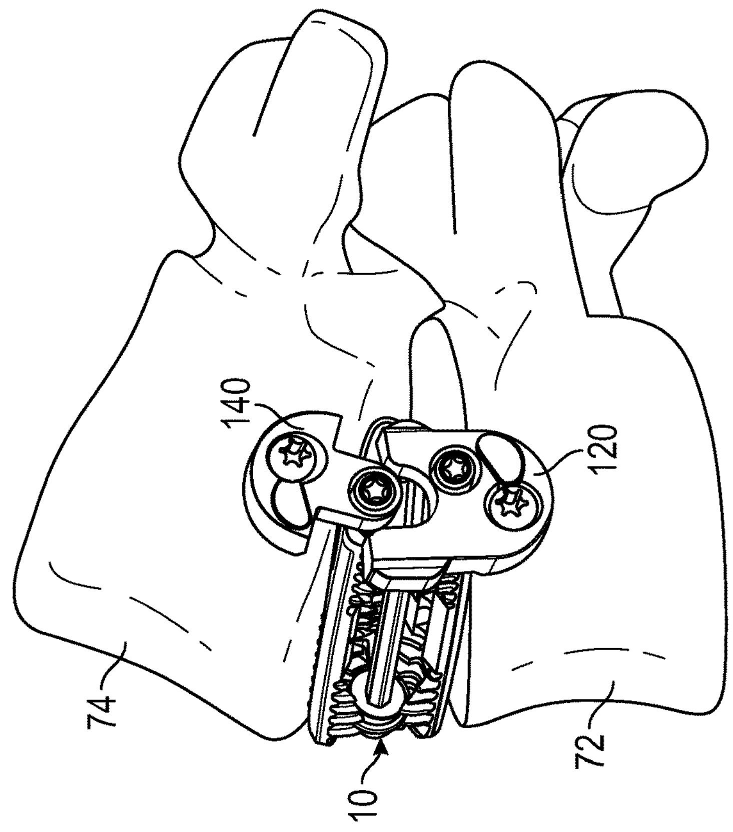

Fasteners 122, 142 such as spinal bone screws can be then inserted through the apertures in the superior and inferior fixation plates 120, 140 and screwed into the first vertebral body 72 and the second vertebral body 74 respectively. Once the fasteners 122, 142 are driven all the way and the heads of the fasteners are received in the countersinks of the apertures in the fixation plates, the fastener-lock mechanisms in the superior and inferior fixation plates 120, 140 automatically actuate, prohibiting the fasteners 122, 142 from backing out. The interbody fusion device 10 can be stabilized and prevented from migrating in the vertebral bodies 72, 74, as shown in FIGS. 11A-11B.

Embodiments of a dual-axis adjustable interbody fusion device with modular fixation or apparatus 100 are described in conjunction with FIGS. 2A-11B. Beneficially, the interbody fusion device with modular fixation 100 can provide stabilization and prevent migration of the interbody fusion device in highly expanded and/or hyperlordotically adjusted configurations to safely promote fusion between adjacent vertebral bodies. The modular superior and inferior fixation plates allow for in-situ attachment of either or both plates to an interbody fusion device of any suitable size and configuration following adjustments of the interbody fusion device, as well as the option for attachment to the interbody fusion device prior to implantation. The modular fixation plates are insertable and attachable to an interbody fusion device via a single surgical approach and patient position, thereby minimizing disruption to the patient anatomy. The modular design also gives the surgeon an option of using the fixation assembly during surgery or leave off if desired following an added interbody configuration. The modular inferior fixation plate 120 and superior fixation plate 140 follow the anterior and posterior angulation of the inferior shell member 32 and the superior shell member 34 of the interbody fusion device 10 from 0-15 degrees respectively, or 0-30 degrees measured from the center of the modular inferior fixation plate to the center of the modular superior fixation plate, thereby allowing for desired screw trajectory and placement into cortical bones.

The interbody fusion device with fixation 100 allows the surgeon to set the interbody fusion device in fine configurations, especially with any height in highly expanded configurations and at any angle in hyperlordotically adjusted configurations between 20°-30° for any patient, without further disruption to the patient anatomy caused by additional surgery needed for an independent screw and plate system. While kyphotic (negative lordosis) adjustments may not be desirable for the lumbosacral segment of the spine, the interbody fusion device with fixation 100 has the ability to adjust to kyphotic and hyperkyphotic angle configurations. Therefore, the interbody fusion device with fixation 100 can provide complete personalization for the patient, allowing the surgeon to adjust the interbody fusion device to any unique height and/or angle (e.g.) 23.4° needed for the patient's spinal balance profile. Conventional techniques may allow for an interbody fusion device to be set at only a few different lordotic configurations such as 20°, 25°, 30°, and separate screw and plate systems have to be used through an additional surgery to stabilize the fusion device in a lordotic configuration.

The interbody fusion device with fixation 100 can also increase surgical efficiency. Conventionally, surgeons have to perform impactful trialing, or sizing of the implant to determine the size of an implant needed for a specific patient. According to embodiments of the disclosure, the interbody fusion device can start at a smaller contracted height and then increase in height in situ. This allows for streamlining or drastically reducing the trialing process, which can in turn decrease the barbaric and rough impact associated with the trialing process. Modular fixation plates may be used for hyperlordotic configurations, reducing the need for placing an extra fixation plate and set of bone screws independent of the interbody fusion device. The use of modular fixation plates causes less disruption to the patient anatomy. Once the surgeon adjusts the interbody fusion device to the patient's unique spinal profile e.g. sagittal balance profile, the intervertebral disc height and lordosis, modular fixation plates can be inserted through the same surgical approach and attached to the fusion device to secure the fusion device to the vertebral bodies without the need for additional surgical approach to place a separate plate and screw fixation system to the spine anteriorly.

The modular design of the fixation assembly also provides benefits pertaining to manufacturing and hospital administration. It can reduce inventory. A single set of inferior and superior fixation plates can work with a dual-axis interbody fusion device of any size and configuration of a making, thereby drastically reducing manufacturing and operational costs. The use of a single set of inferior and superior fixation plates with dual-axis interbody fusion devices of any size and configuration simplifies the need of tracking, by tracking only one set of fixation plates in the hospital or the operating room.

Dual-Axis Adjustable Conjoined Spinal System

With reference to FIGS. 12A-19B, an example dual-axis adjustable spinal system 200 according to embodiments of the disclosure will now be described. The use of a single fixation plate in the spinal system allows for attachment of a fixation assembly to the interbody fusion device in situ following adjustment of the interbody fusion device to a desired configuration in the adjacent vertebrae. The single fixation plate can be constructed from a material having sufficient strength such as titanium, stainless steel or other metal or metal alloy to provide orthotic support or supplemental fixation in addition to providing stabilization and preventing migration of the interbody fusion device. As used herein, the term "supplemental fixation" refers to an embodiment of the single fixation plate serving as an orthotic capable of holding adjacent vertebrae in place or immobilizing movement of adjacent vertebrae until arthrodesis (bony fusion) takes place.

As shown in FIGS. 12A-12E, the spinal system 200 comprises an interbody fusion device 10 and a fixation assembly 210. The interbody fusion device 10 may be the same as or similar to the device 10 described above in conjunction with FIGS. 1A-1C. Alternatively, the interbody fusion device 10 can be any suitable dual-axis adjustable interbody fusion devices available from various manufacturers, which can be further adapted or modified for use with the fixation assembly 210.

Figures 12A, 12B:
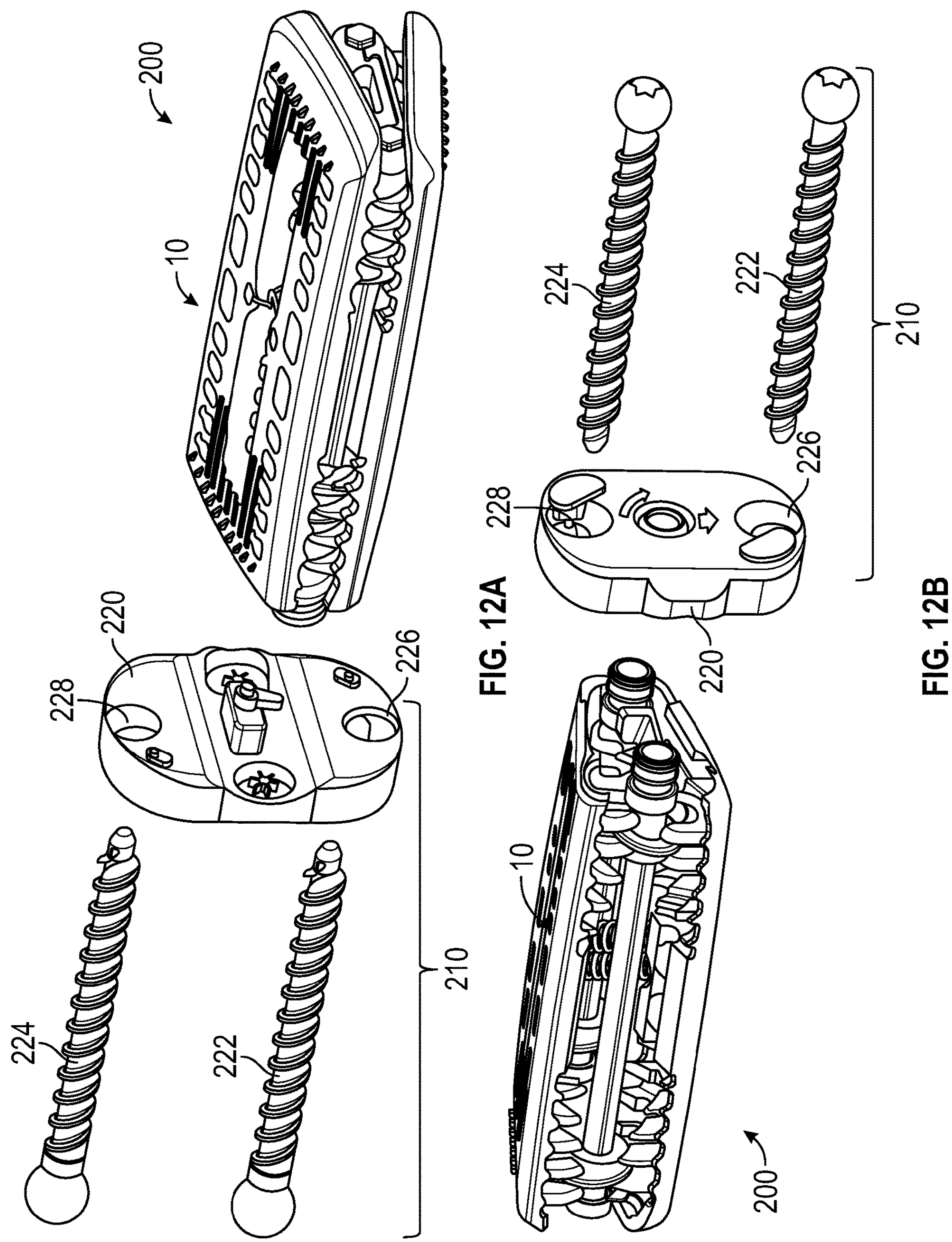
FIGS. 12A-12E depict an example dual-axis adjustable conjoined spinal system according to embodiments of the disclosure.
Figure 12D:
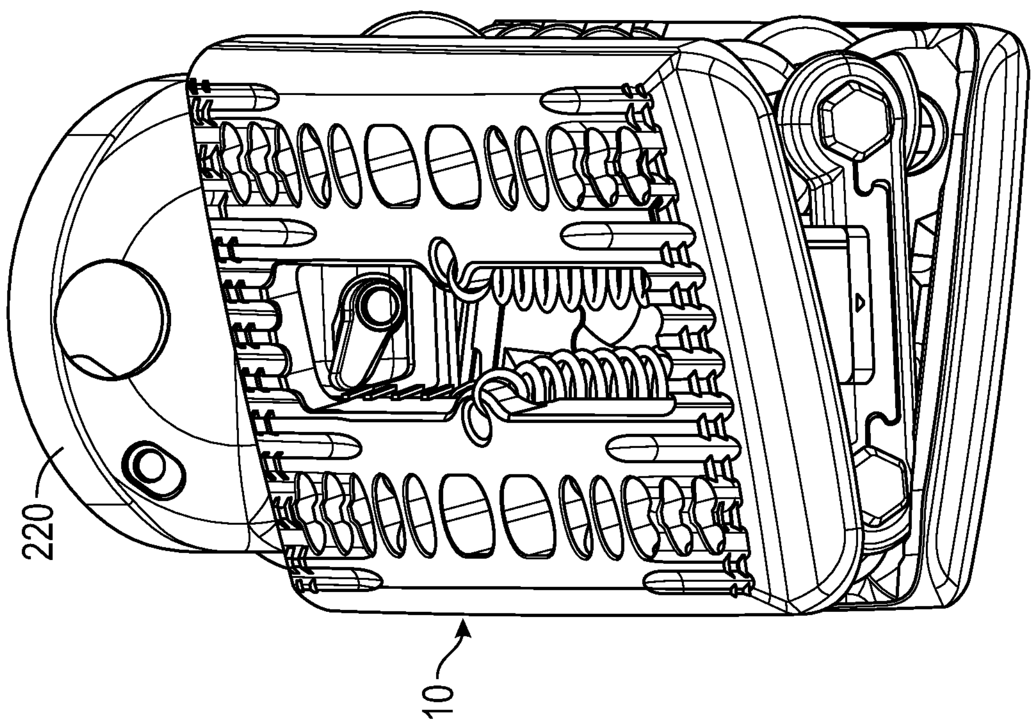
Figure 12C:
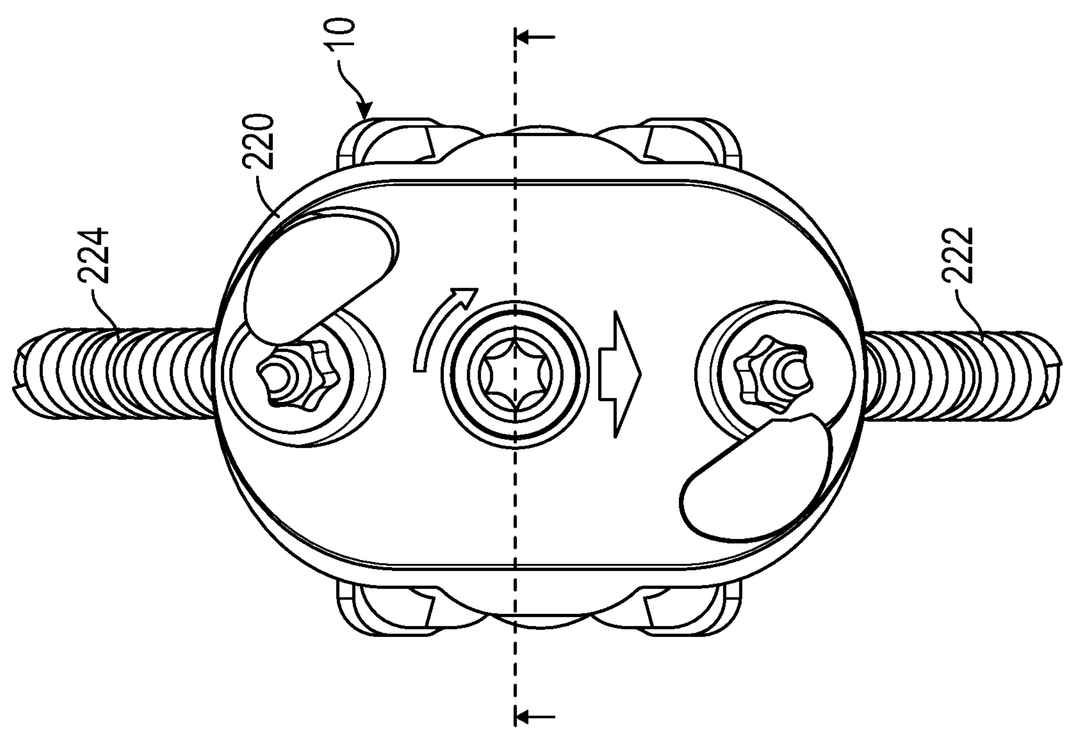

The fixation assembly 210 comprises a single fixation plate 220, at least a first fastener 222 and a second fastener 224. The single fixation plate 220 is configured to be attachable to the interbody fusion device 10. The single fixation plate 220 is provided with at least a first aperture 226 configured for insertion of the first fastener 226 therethrough to secure to a first vertebral body, and a second aperture 228 configured for insertion of the second fastener therethrough to secure to a second vertebral body. As used herein, the term "single" refers to one fixation plate provided with at least two apertures for insertion of at least two fasteners capable of stabilizing an interbody fusion device between two adjacent vertebral bodies. However, the use of the term "single" does not exclude other parts assembled to the fixation plate for performing other functions such as locking etc. As used herein, the term "fixation plate" includes reference to a plate member or a plate assembly comprising a plate member and other parts or mechanisms assembled to the plate member. While two fasteners and two apertures in the single fixation plate are shown for illustration purpose, other embodiments may include more than two fasteners and more than two apertures in the fixation plate. Further, FIG. 12C-12D show assembled views of the spinal system 200 where the single fixation plate 220 is attached to the interbody fusion device 10, with the first and second fasteners 222, 224 being inserted through the apertures in the fixation plate. It should be noted that in use, the single fixation plate 220 can be attached to the interbody fusion device 10 in situ, or when the interbody fusion device 10 has been inserted in the patient and placed between adjacent vertebral bodies. The single fixation plate 220 may also be attached to the interbody fusion device 10 prior to implantation if desired, assuming the interbody fusion device is adjusted prior to implantation. FIG. 18A, which will be described in greater detail below, shows that a single fixation plate 220 is inserted in the patient and attached to an interbody fusion device with an operation instrument after the interbody fusion device has been placed, expanded, and/or lordotically adjusted to a proper configuration between adjacent vertebrae.

Figure 12E:
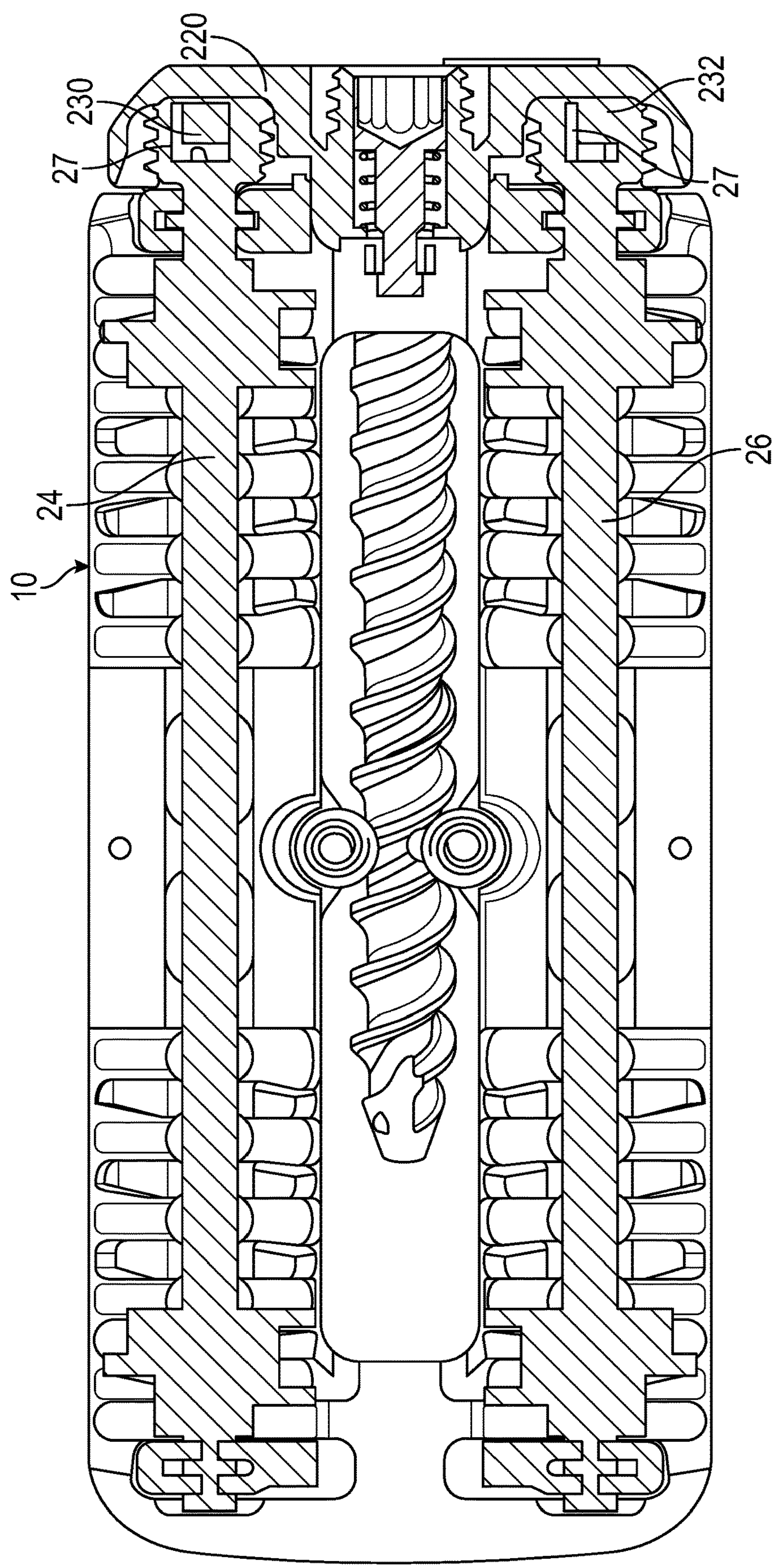
Figure 13A:
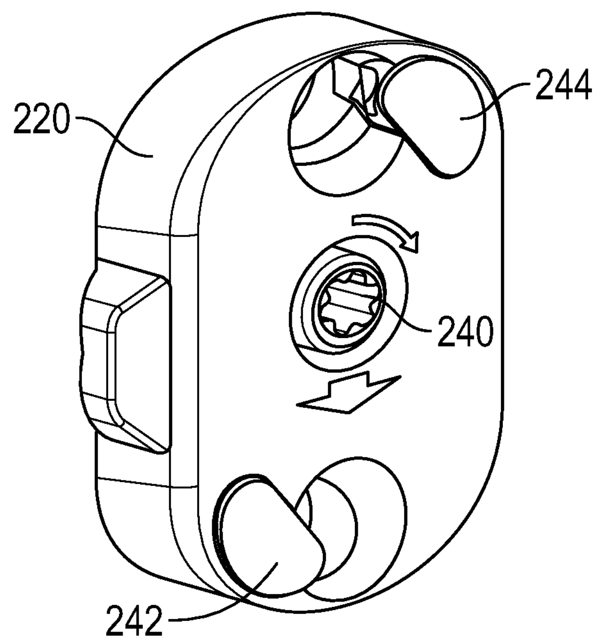
FIGS. 13A-13F depict an example single fixation plate according to embodiments of the disclosure.
Figure 13B:
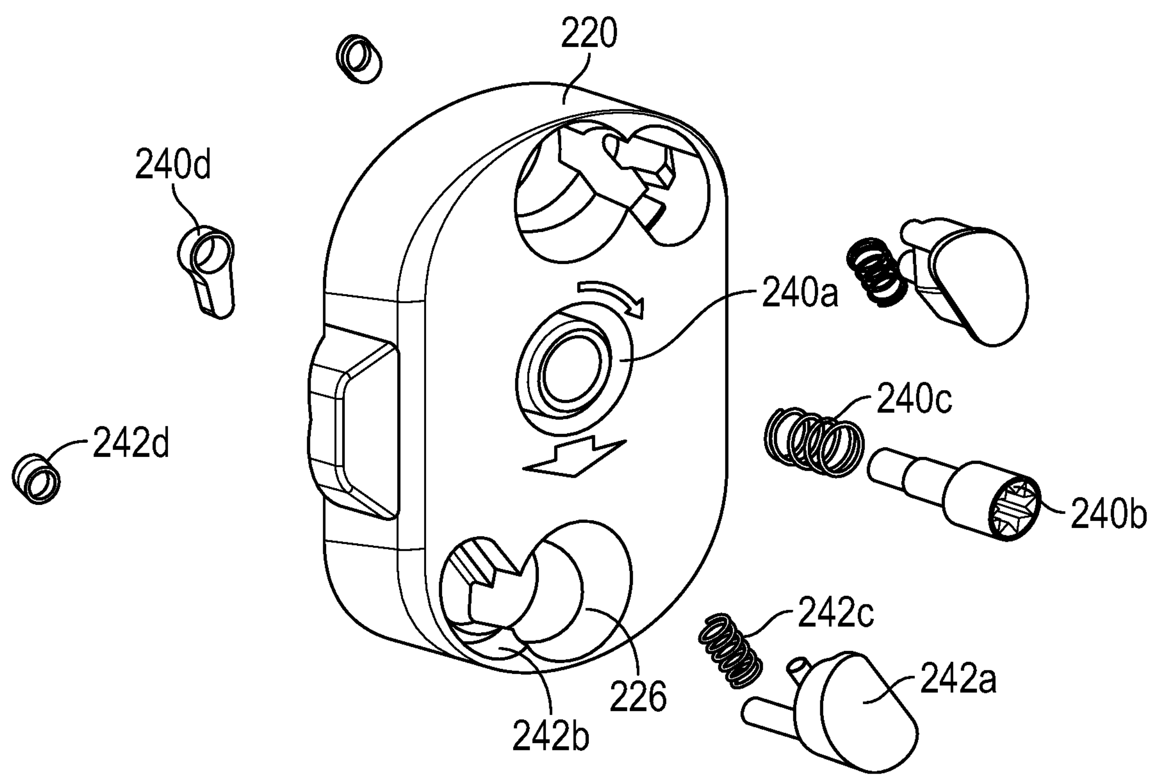
Figure 13F:
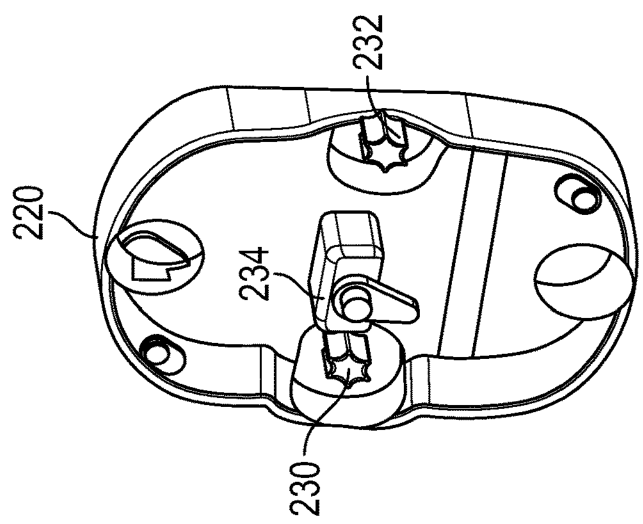
Figure 13E:
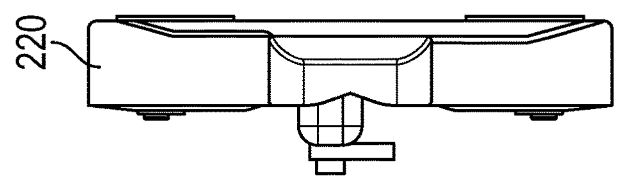
Figure 13D:
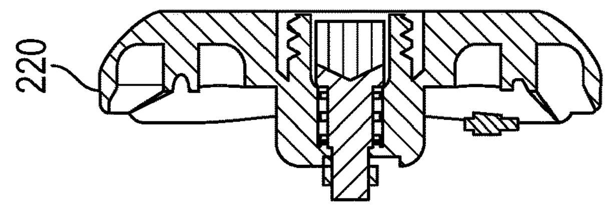
Figure 13C:
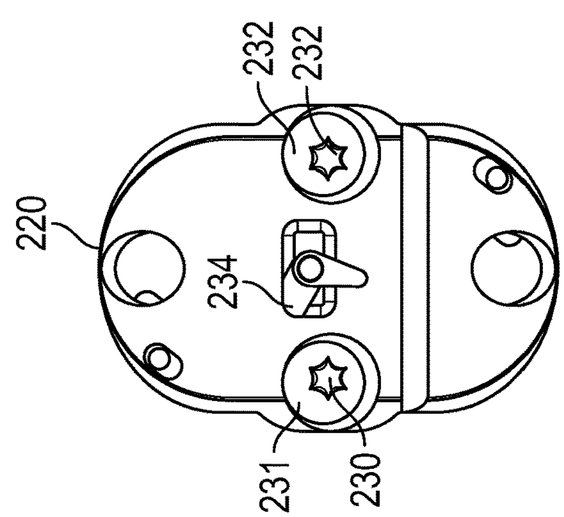

With reference to FIGS. 13A-13F, the single fixation plate 220 can be configured to be attachable to the interbody fusion device 10. For instance, the single fixation plate 220 may be provided with geometry features configured for attachment to the interbody fusion device 10 and preventing unwanted rotation of the drive shafts 24 and 26 of the interbody fusion device 10. According to certain embodiments of the disclosure, the single fixation plate 220 in the back side may include a first male geometry 230 and a second male geometry 232 spaced apart to each other (FIGS. 13C and 13F). The first and second male geometries 230 and 232 may be configured to be inserted into the female geometries 27 in the end portions of the first (e.g. posterior) and second (e.g. anterior) drive shafts 24 and 26 of the interbody fusion device 10 respectively. By way of example, the first and second male geometries 230, 232 may have male hexalobe features which can be tightly mated into the female hexalobe features 27 in the end portions of the first and second drive shafts 24, 26 to prevent unwanted rotation of the first and second drive shafts 24, 26. The first and second male geometries may have other mating features and the above hexalobe example is provided for illustration purpose. Surrounding each of the first and second male geometries 230, 232, circular grooves 231, 233 can be provided to receive or accommodate the end portions of the first and second drive shafts 24 and 26 of the interbody fusion device 10 when the single fixation plate 220 is attached to the interbody fusion device 10. FIG. 12E shows attachment of the single fixation plate 220 to the interbody fusion device 10, where the first and second male geometries 230 and 232 in the single fixation plate 220 are received in the female geometries 27 in the end portions of the first and second drive shafts 24, 26 respectively, and the end portions of the first and second drive shafts 24 and 26 fit in the circular grooves in the single fixation plate 230.

Figure 14B:
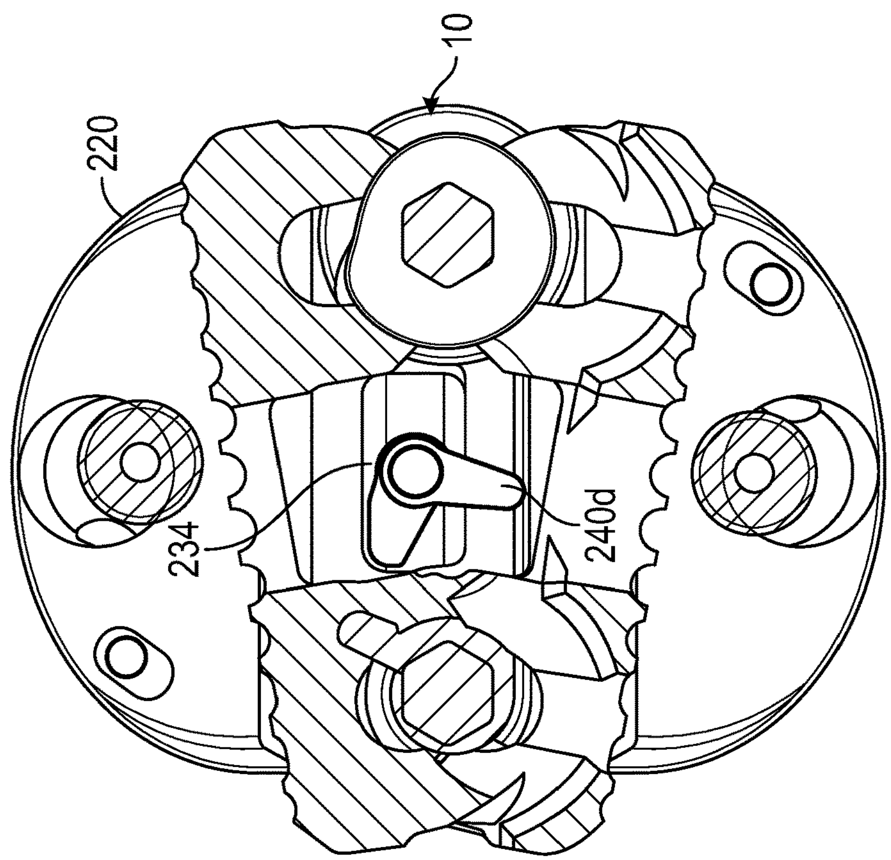
FIGS. 14A-14B show attachment of a single fixation plate and screw assembly to a dual-axis adjustable interbody fusion device.
Figure 14A:
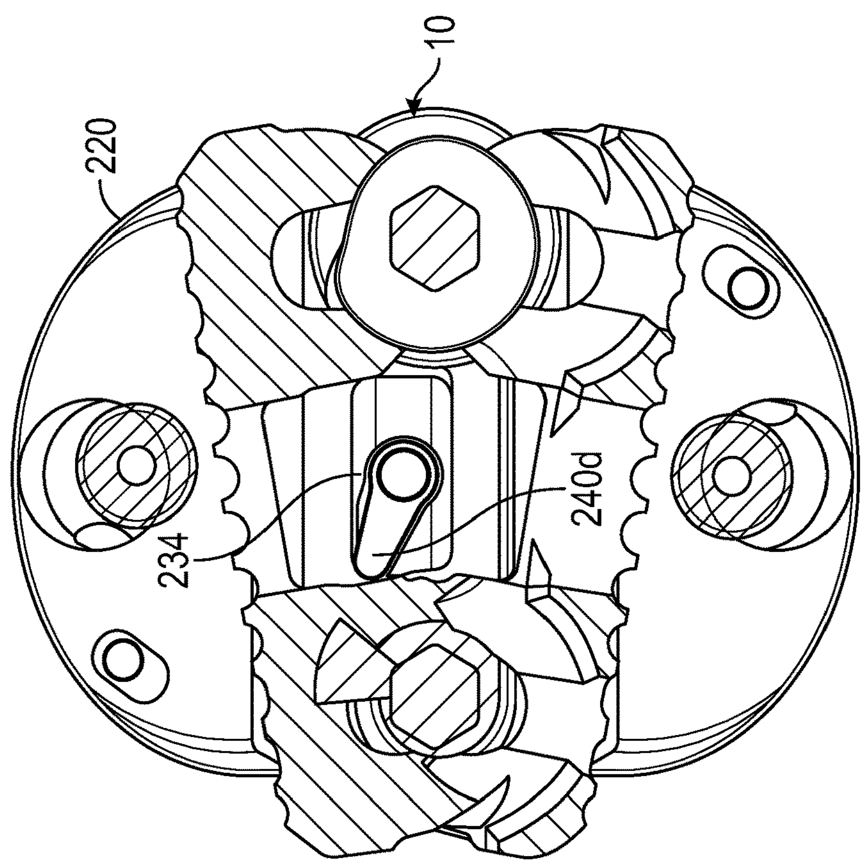

With reference to FIGS. 130-13F, the single fixation plate 220 may alternatively or additionally include a protruding portion 234 configured to be insertable into the interbody fusion device 10 to stabilize and prevent migration of the interbody fusion device 10 placed between adjacent vertebrae. According to certain embodiments of the disclosure, the protruding portion 234 in the single fixation plate 220 may have a geometry configured to tightly mate with an internal component(s) of the interbody fusion device 10 to restrict unwanted movement of the interbody fusion device 10. By way of example, the protruding portion 234 may have a geometry generally in the shape of a rectangular prism, which can be tightly inserted in a ramp-like geometry of the thrust bearing 60 (FIG. 1A) of the interbody fusion device 10. As such, unwanted translational movement of the interbody fusion device 10 in any of lateral, posterior, and anterior directions can be prohibited or minimized. The protruding portion 234 may also in any other suitable shapes or forms such as a cube, semi-cylinder, or polygonal prism shape, etc. FIGS. 14A-14B show the protruding portion 234 of the single fixation plate 220 inserted in the interbody fusion device 10, and an attachment-lock mechanism 240 in an unlocked state (FIG. 14A) and a locked state (FIG. 14B), to be described further below.

With reference to FIGS. 13A-13F, the single fixation plate 220 may include an attachment-lock mechanism 240 engageable to lock the interbody fusion device 10 or secure the attachment of the single fixation plate 220 to the interbody fusion device 10. According to certain embodiment of the disclosure, the attachment-lock mechanism 240 may be the same as or similar to the attachment-lock mechanism 130 shown in FIGS. 3A-3D or the attachment-lock mechanism 150 shown in FIGS. 4A-4D. For completeness of description, the attachment-lock mechanism 240 in the single fixation plate 220 may include a lock housing 240*a*, a rod 240*b*, a compression spring 240*c* loaded on the rod 240*b* and retained in the lock housing 240*a*, and a latch 240*d* coupled to a distal end portion of the rod. The proximal end portion of the lock rod 240*b* may have features for receiving a driving tool to actuate the attachment-lock mechanism 240. For example, the proximal end portion of the rod 240*b* may be provided with a female hexalobe feature for receiving a driver having a male hexalobe feature. In use, the user may press the rod 240*b* with a driver to displace the latch 240*d* coupled to the distal end portion of the rod 240*b* to allow the latch to rotate and hook to a component in the interbody fusion device 10. The compression spring 240*c* loaded on the rod 240*b* apply a force to the latch 240*d*, and upon release of the driver, the latch 240*d* tightens the attachment of the inferior fixation plate 220 to the interbody fusion device 10, or locks the interbody fusion device 10 to the single fixation plate 220. The housing 240*a* of the attachment-lock mechanism 240 may be provided with features such as a thread configured for connecting with an operation instrument for actuating the attachment-lock mechanism 240 and/or placing the single fixation plate in the patient anatomy. FIG. 14A shows the attachment-lock mechanism 240 in an unlocked state where the latch 240*d* is in an unlocked position. FIG. 14B shows the attachment-lock mechanism 240 in a locked state where the latch 240*d* is a locked position hooking to a component (e.g. the thrust bearing) of the interbody fusion device 10.

With reference to FIGS. 13A-13B, the single fixation plate 220 may further include a first fastener-lock mechanism 242 and a second fastener-lock mechanism 244. The first and second fastener-lock mechanisms in the single fixation plate 220 may be the same as or similar to the fastener-lock mechanism 132 shown in FIGS. 3A-3D or the fastener-lock mechanism 152 shown in 4A-4D. For completeness of description, the first fastener-lock mechanism 242 in the single fixation plate 220 may comprise a lock component 242*a* received in a recess 242*b* adjacent to the first aperture 226, a compression spring 242*c* loaded on a part of the lock component 242*a*, and a retainer 242*d* connected to a part of the lock component 242*a*. The retainer 242*d* retains the lock component 242*a* in the recess 242*b* via a compression spring loaded on the lock component 242*a* and is slidable with the lock component 242*a* relative to the single fixation plate 220, allowing the lock component 242*a* to extend over and/or retract from the aperture 226 when in use. The second fastener-lock mechanism 244 may be the same as or similar to the first fastener-lock mechanism 242. Alternatively, the first and second fastener-lock mechanisms 242, 244 are the same as or similar to the fastener-lock mechanisms 426 and 446 in the fixation plates 420 and 440 to be described in conjunction with FIGS. 27A-27B.

FIGS. 15A-15B depict some aspects of the first fastener-lock mechanism 242 in the single fixation plate 220 with greater clarity. The compressed state and the extended (free) state of the compression spring allows the spring-loaded lock component 242*a* to have an unlock/open position and a locked position respectively. In the extended or free state of the compression spring, the lock component 242*a* extends partially over the aperture 226 in the fixation plate 220. When a fastener 222 is inserted into the aperture 226 by a driver, the spring-loaded lock component 242*a* is forced away from the aperture 226, allowing the fastener 222 to be fastened e.g. screwed into a vertebral body. Once the fastener 222 is screwed all the way and the head of the fastener 222 is flushed with or below the surface of the fixation plate 220, the spring-loaded lock component 242*a* springs back at least partially over the fastener head, preventing the fastener 222 from backing out. The fastener-lock mechanism 242 of the disclosure allows for "zero step" locking since the surgeon does not need any surgical instrument or step to engage the fastener-lock mechanism 242 in order to cover the fastener head to keep them from backing out e.g. unthreading from the vertebral body.

Figure 16B:
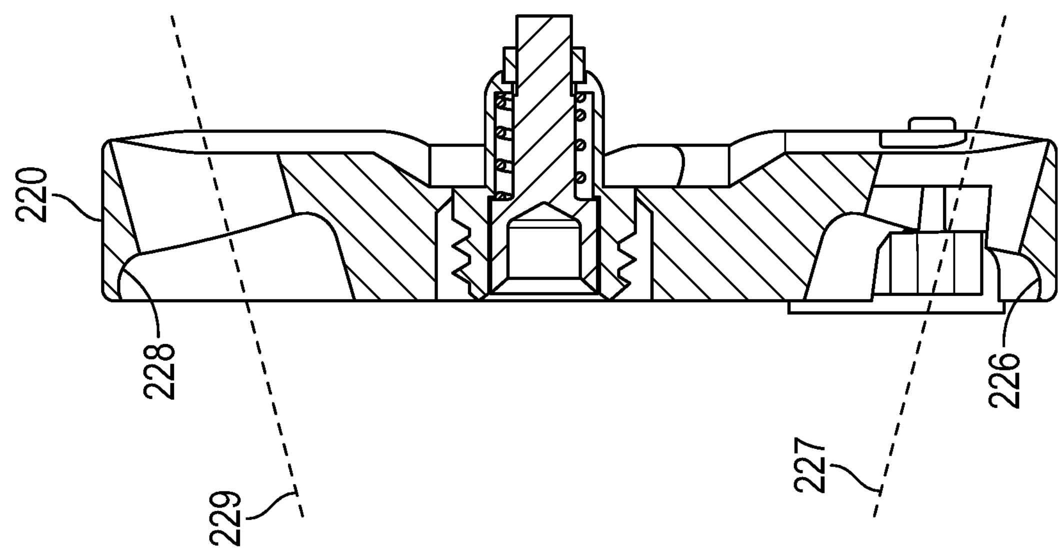
FIGS. 16A-16B show an angulation feature of the apertures in the single fixation plate.
Figure 16A:
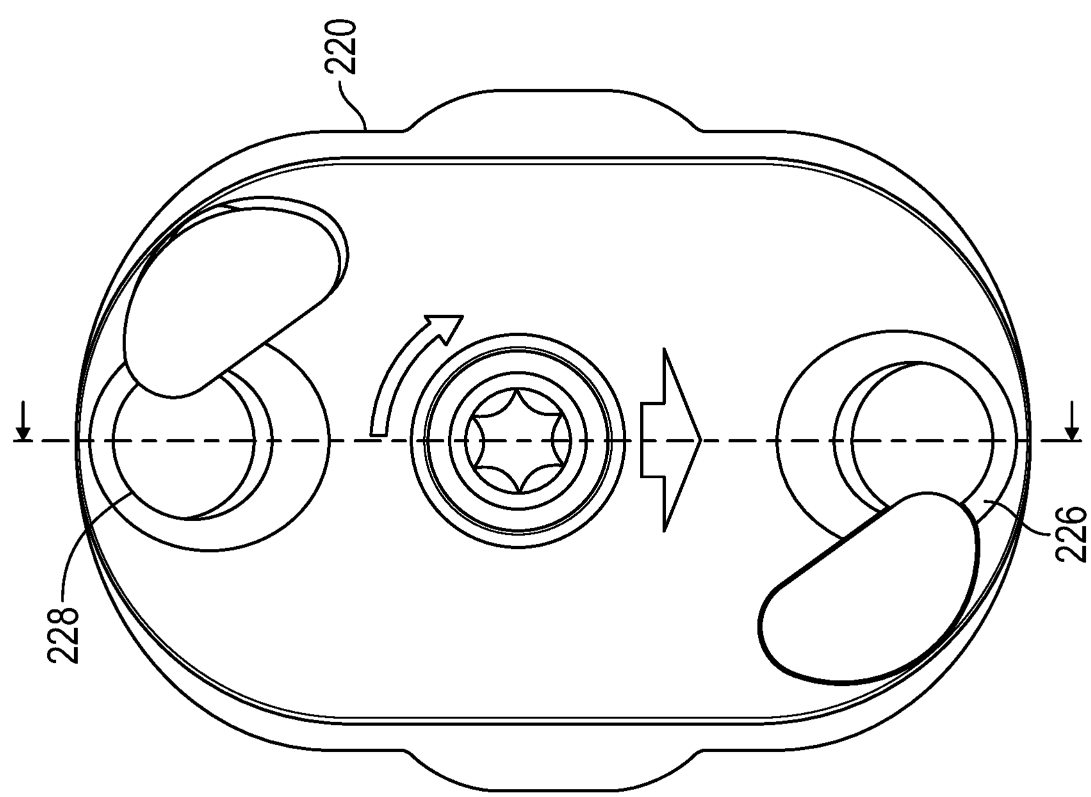

FIGS. 16A and 16B shows that the first and second apertures 226 and 268 in the single fixation plate 220 may be angled. For example, the centerline 227 of the first aperture 226 may be angled from 0-15 degrees with respect to a reference plane such as a reference plane parallel with the surface of the fixation plate. Similarly, the centerline 229 of the second aperture 228 may be angled from 0-15 degrees with respect to a reference plane such as a reference plane parallel with the surface of the single fixation plate. An angled aperture allows for the fastener inserted therethrough to have an angled trajectory, providing optimal purchase for the fastener to the vertebral body. The first and second apertures 226, 228 can be configured to allow the first and second fastener 222 and 224 to angle from 0-15 degrees e.g. in a caudal or cephalad direction respectively or in any other directions. The first and second apertures 226, 228 may include a counterbore or countersink portion configured for receiving the head of the first and second fasteners. The head of the fasteners may have a spherical shape as shown FIGS. 15A-15B or any other suitable shapes such as tapered or cylindrical shape. Examples of fasteners include but are not limited to spinal expansion head screws, spinal locking screws, spinal self-locking screws, spinal shaft screws, spinal nails, spinal barbs, spinal hooks, and any other threaded or unthreaded fasteners.

Figure 17A:
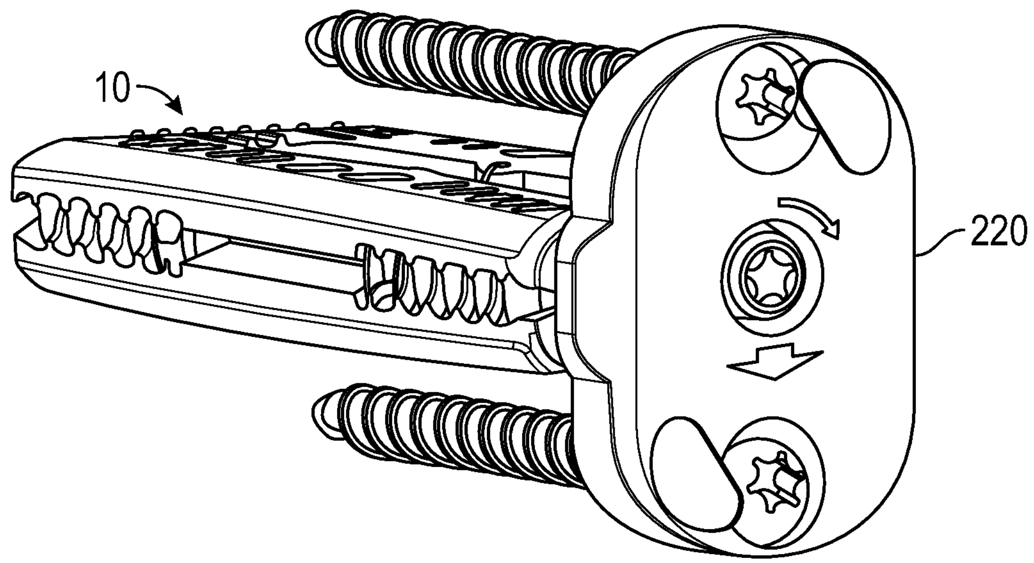
FIGS. 17A-17C show attachment of a single fixation plate to a dual-axis adjustable interbody fusion device in a contacted, an expanded, and a lordotically adjusted configuration respectively.
Figure 17B:
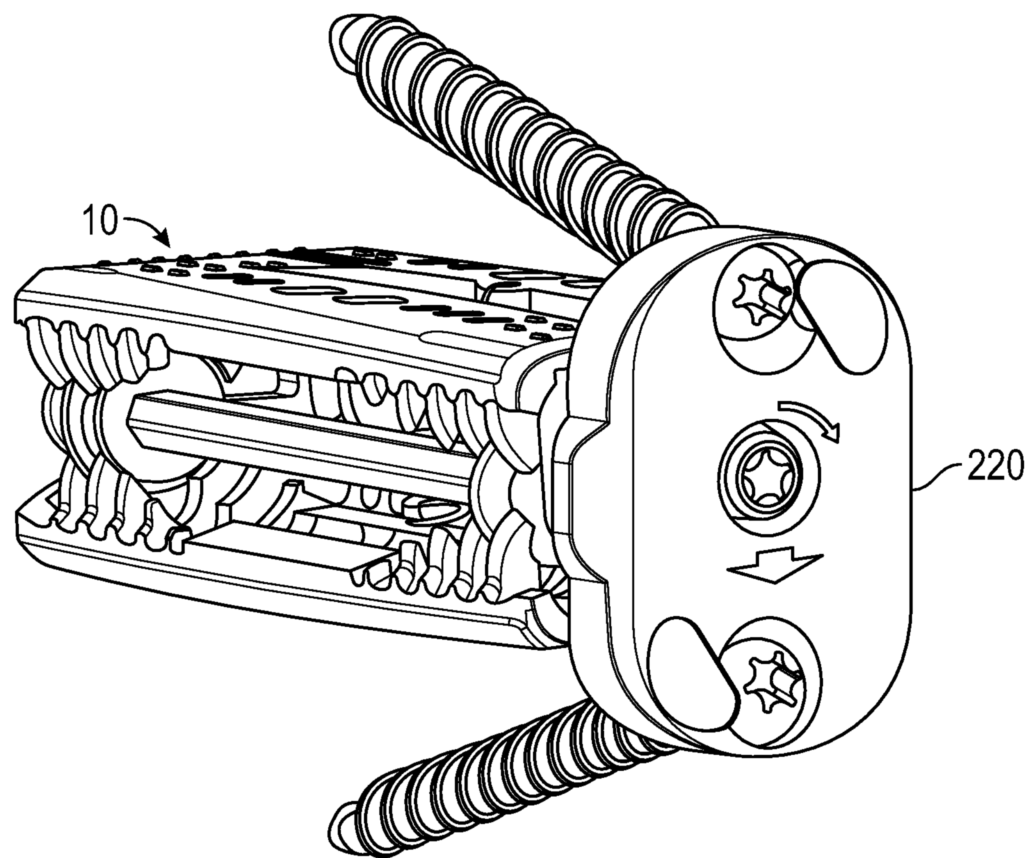
Figure 17C:
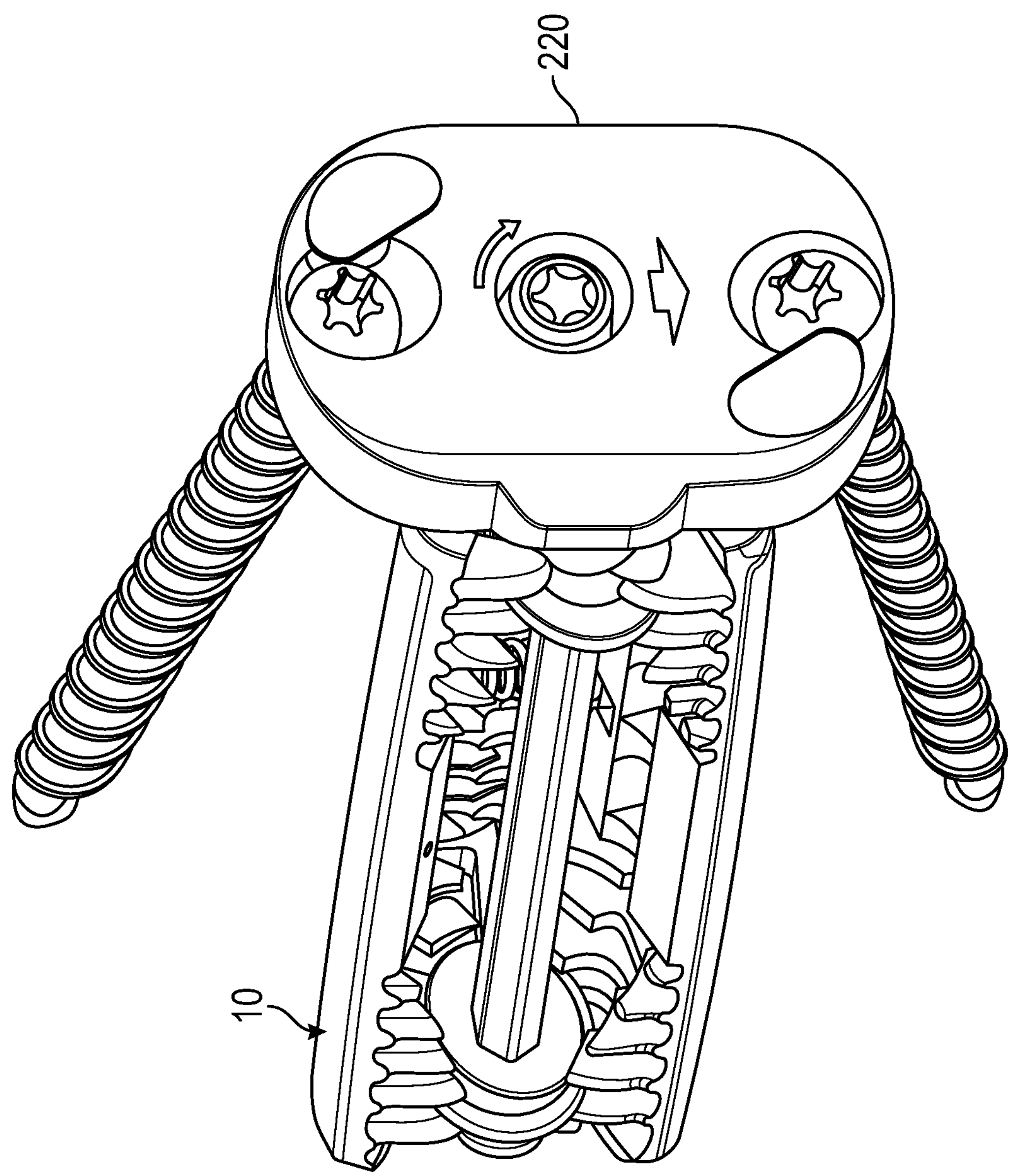

FIG. 17A-17C illustrate that the single fixation plate 220 can be attached to the interbody fusion device 10 in various configurations, including in a contracted configuration, a fully expanded configuration, and a lordotically or hyperlordotically adjusted configuration. While kyphotic (negative lordosis) adjustments may not be desirable for the lumbosacral segment of the spine, the interbody fusion device 10 can be connected with the single fixation plate assembly in kyphotic and hyperkyphotic angle configurations. By way of example where the interbody fusion device 10 is placed between adjacent vertebrae via a lateral surgical procedure, FIG. 17A shows that the single fixation plate 220 can be attached to the interbody fusion device 10 in a contracted configuration having an anterior height of 8.4 mm, a posterior height of 8.4 mm, and a lordosis of 0 degree. FIG. 17B shows an example where the single fixation plate 220 is attached to the interbody fusion device 10 in a fully expanded configuration having an anterior height of 16.1 mm, a posterior height of 16.1 mm, and a lordosis of 0 degree. FIG. 17C shows an example where the single fixation plate 220 is attached to the interbody fusion device 10 in a hyperlordotically adjusted configuration having an anterior height of 17.1 mm, a posterior height of 7.2, and a lordosis of 30 degree. The angled first and second apertures in the single fixation plate 220 allow screw angulation up to 15 degrees in the caudal and cephalad directions respectively, as shown in FIGS. 17B-17C.

Figure 18:
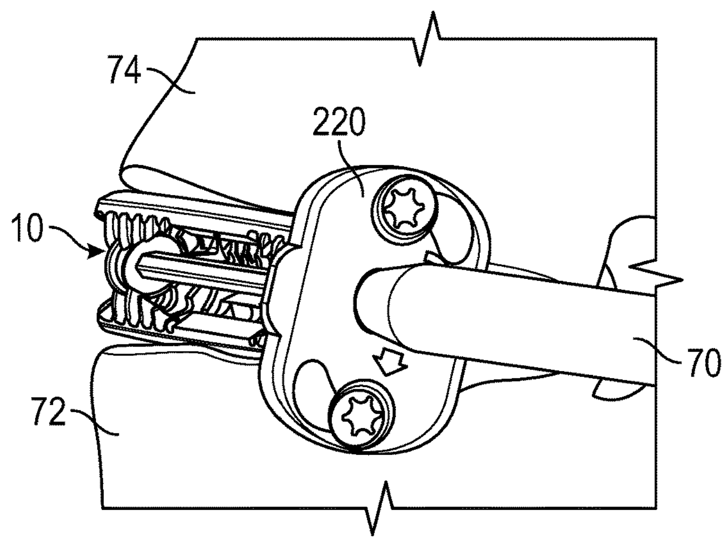
FIG. 18 shows attaching of a single fixation plate to a dual-axis adjustable interbody fusion device placed between adjacent vertebrae using an operation instrument.

The dual-axis adjustable spinal system 200 can be used in treatment of various spinal diseases including but not limited to degenerative disc disease (DDD), spondylolisthesis, retrolisthesis, trauma, tumors, deformities, pseudoarthrosis, previous failed fusions, and so on. In use, as shown in FIG. 18, the single fixation plate 220 can be inserted and attached to an interbody fusion device 10 in situ. For instance, an interbody fusion device 10 in a contracted configuration can be first inserted and placed between adjacent vertebrae 72, 74 using an operation instrument 70 via a suitable surgical procedure. Suitable surgical procedure for introducing the interbody fusion device 10 in the patent anatomy include a lateral lumbar interbody fusion (LLIF) procedure, an anterior lumbar interbody fusion (ALIF), posterior lumbar interbody fusion (PLIF) procedure, and any other suitable surgical procedures performed in the lumbar or other regions of the spinal column. Various suitable operation instruments are described in U.S. Ser. No. 15/661,435 filed Jul. 17, 2017 entitled "Surgical Operating Instrument for Expandable and Adjustable Lordosis Interbody Fusion Systems" and U.S. Ser. No. 16/035,637 filed Jul. 15, 2018 entitled "Surgical Operating Instrument for Expandable and Adjustable Lordosis Interbody Fusion Systems," the disclosures of all of which are incorporated herein in their entirety. The interbody fusion device 10 can be expanded and/or lordotically adjusted using an operation instrument 70, forming a suitable configuration between the adjacent vertebrae 72, 74. By way of example, the operation instrument 70 can connect the interbody fusion device 10 via the external threads 25 on the end portions of the posterior and anterior drive shafts 24, 26, and expand or lordotically adjust the interbody fusion device 10 by engaging the female features 27 in the end portions of the posterior and anterior drive shafts 24, 26 (FIG. 1A). The interbody fusion device 10 can be expanded and/or lordotically adjusted to a configuration suitable for treating the patient.

Then, the single fixation plate 220 can be introduced to the target area, via the same surgical approach for inserting and placing the interbody fusion device 10, and attached to the interbody fusion device 10. According to embodiments of the disclosure, the operation instrument 70 used for placing and operating the interbody fusion device 10 can be used for inserting and attaching the single fixation plate 220. By way of example, the surgeon can connect the single fixation plate 220 to the operation instrument 70 via the thread provided at the lock housing 240*a* of lock-attachment mechanism 240, introduce the single fixation plate 220 to the target area via the same surgical approach, align the first and second male geometries 230, 232 with the female geometries 27 in the end portions of the posterior and anterior drive shafts 24, 26 of the interbody fusion device 10, and insert the single fixation plate 220 to the interbody fusion device 10. The interbody fusion device 10 can further be locked to the single fixation plate 220 using the operation instrument 70 by actuating the attachment-lock mechanism 240.

Figure 19A:
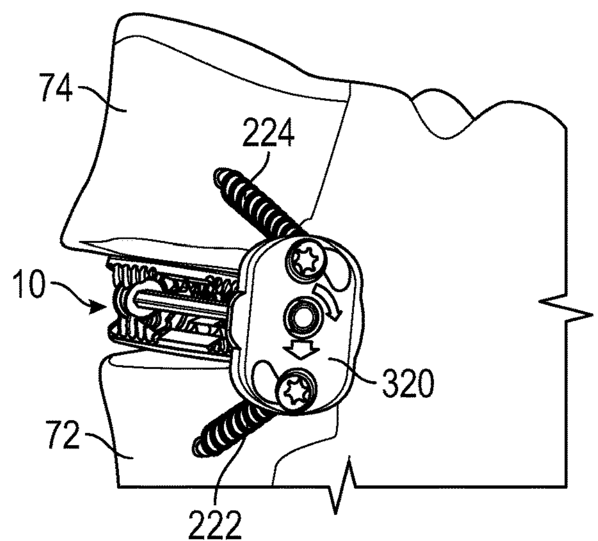
FIGS. 19A-19B show a dual-axis adjustable interbody fusion device secured by a single fixation plate to adjacent vertebral bodies.
Figure 19B:
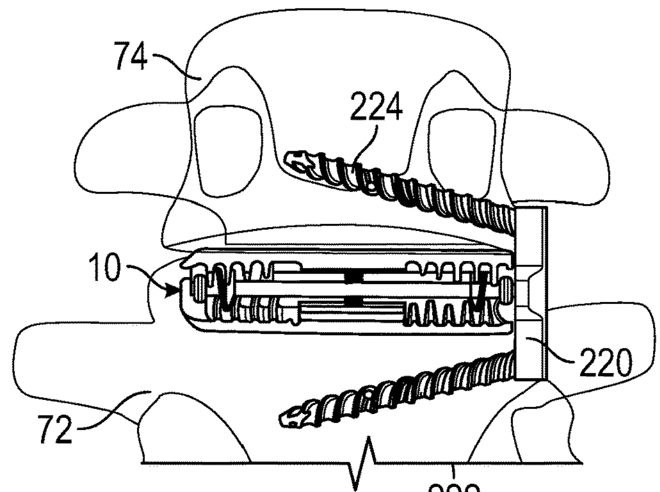

Fasteners 222, 224 such as bone screws can be then inserted through the apertures in the single fixation plate 220 and screwed into the first vertebral body 72 and the second vertebral body 74 respectively. Once the fasteners 222, 224 are driven all the way and the heads of the fasteners 222, 224 are received in the apertures in the single fixation plate 220, the fastener-lock mechanisms 242, 244 in the single fixation plates 220 automatically actuate to lock the fasteners 222 and 224 prohibiting them from backing out. The interbody fusion device 10 can be stabilized and prevented from migrating in the vertebral bodies 72, 74, as shown in FIGS. 19A-19B. In addition, the single fixation plate 220 can be constructed from a material having sufficient strength such as stainless steel or other metal or metal alloy to provide supplemental fixation holding the adjacent vertebrae 72 and 74 in place or immobilizing movement of adjacent vertebrae for promoting safe body fusion.

Embodiments of a dual-axis adjustable spinal system 200 comprising a single fixation plate are described in conjunction with FIGS. 12A-19B. Beneficially, the spinal system 200 can provide stabilization and promote fusion between adjacent vertebral bodies without further need of supplemental posterior fixation when treating degenerative disc disease, spondylolisthesis, retrolisthesis (Grade 1), etc. The single fixation plate can be constructed with sufficient strength to provide orthotic support or supplemental fixation. The single fixation plate 220 is implantable and configurable to attach to an interbody fusion device via a single surgical approach and patient position, thereby minimizing disruption to the patient anatomy. The geometry such as the male geometries in the single fixation plate can act as secondary safety lock for a dual-axis interbody fusion device. The single fixation plate is attachable to all footprints and configurations of interbody fusion devices.

As in other embodiments of apparatus 100, the spinal system 200 allows the surgeon to set the interbody fusion device in fine configurations, especially with any height in highly expanded configurations and at any angle in hyperlordotically adjusted configurations between 20°-30° for any patient, without further disruption to the patient anatomy caused by additional surgery needed for an independent screw and plate system. Therefore, the spinal system 200 can provide complete personalization for the patient, allowing the surgeon to adjust the interbody fusion device to any unique height and/or angle (e.g. 23.4°) needed for the patient's spinal balance profile. Conventional techniques may allow for an interbody fusion device to be set at only a few predetermined lordotic configurations such as 20°, 25°, 30°, and separate screw and plate systems have to be used through an additional surgery to stabilize the fusion device in a lordotic configuration.

The spinal system 200 can also increase surgery efficiency. Conventionally, surgeons have to perform impactful trialing, or sizing of the implant to determine the size of an implant needed for a specific patient. According to embodiments of the disclosure, the interbody fusion device can start at a smaller contracted height and then increase in height. This allows for streamlining or drastically reducing the trialing process, which can in turn decrease the barbaric and rough impact associated with the trialing process. Once the surgeon adjusts the fusion device to the patient's unique spinal profile e.g. sagittal balance profile such as the intervertebral disc height and lordosis, a single fixation plate can be inserted through the same surgical approach and attached to the interbody fusion device to secure the fusion device to the vertebral bodies, causing less disruption to the patient anatomy. The single fixation plate can also provide supplemental fixation, eliminating the need for a separate plate and screw fixation system through a separate surgical approach to the patient's spine.

The spinal system 200 also provides benefits pertaining manufacturing and hospital administration. It can reduce inventory. A single set of a fixation plate can work with a dual-axis adjustable interbody fusion device of any size and configuration of a making, thereby drastically reducing manufacturing and operational costs. The use of a single set of a fixation plate with any dual-axis interbody fusion device size and configuration simplifies the need of tracking, by tracking only one set of fixation plates in the hospital or the operating room.

Dual-Axis Adjustable Variable Spinal System

With reference to FIGS. 20A-25B, an example dual-axis adjustable spinal system 300 according to embodiments of the disclosure will now be described. The spinal system 300 shown in FIGS. 20A-25B is similar in many aspects to the spinal system 200 described above in conjunction with FIG. 12A-19B. For example, the spinal system 300 comprises a single fixation plate for attachment to an interbody fusion device in situ following adjustment of the interbody fusion device to a desired configuration in adjacent vertebrae. The single fixation plate can be constructed from a material having sufficient strength to provide supplemental fixation, in addition to providing stabilization and preventing migration of the interbody fusion device. Some unique aspects of the spinal system 300 are set forth below.

Figures 20A, 20B:
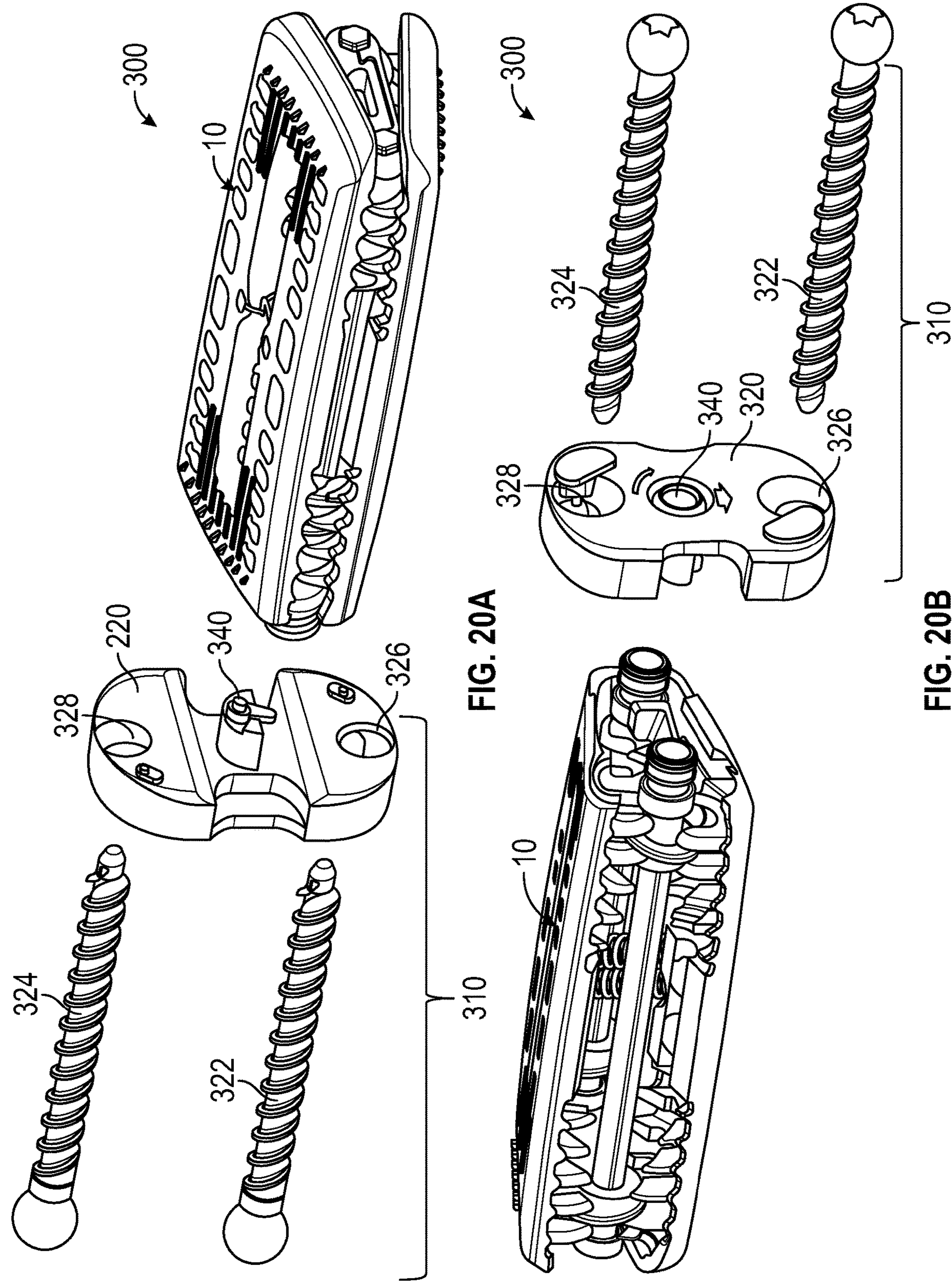
FIGS. 20A-20D depict an example dual-axis adjustable variable spinal system according to embodiments of the disclosure.
Figure 20C:
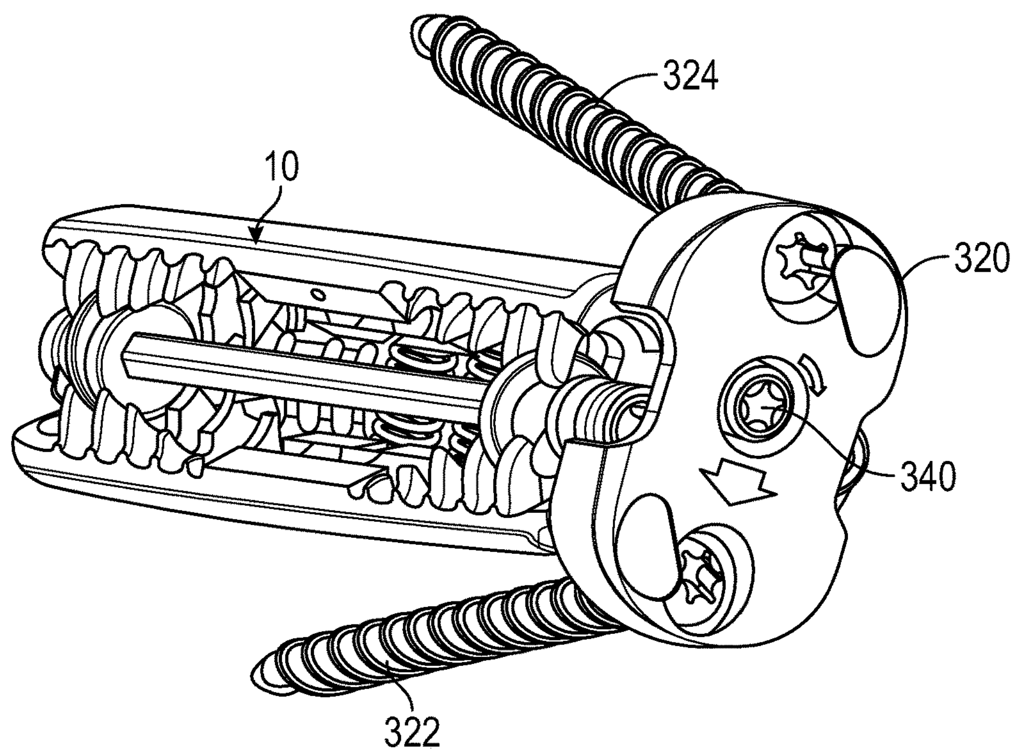
Figure 20D:
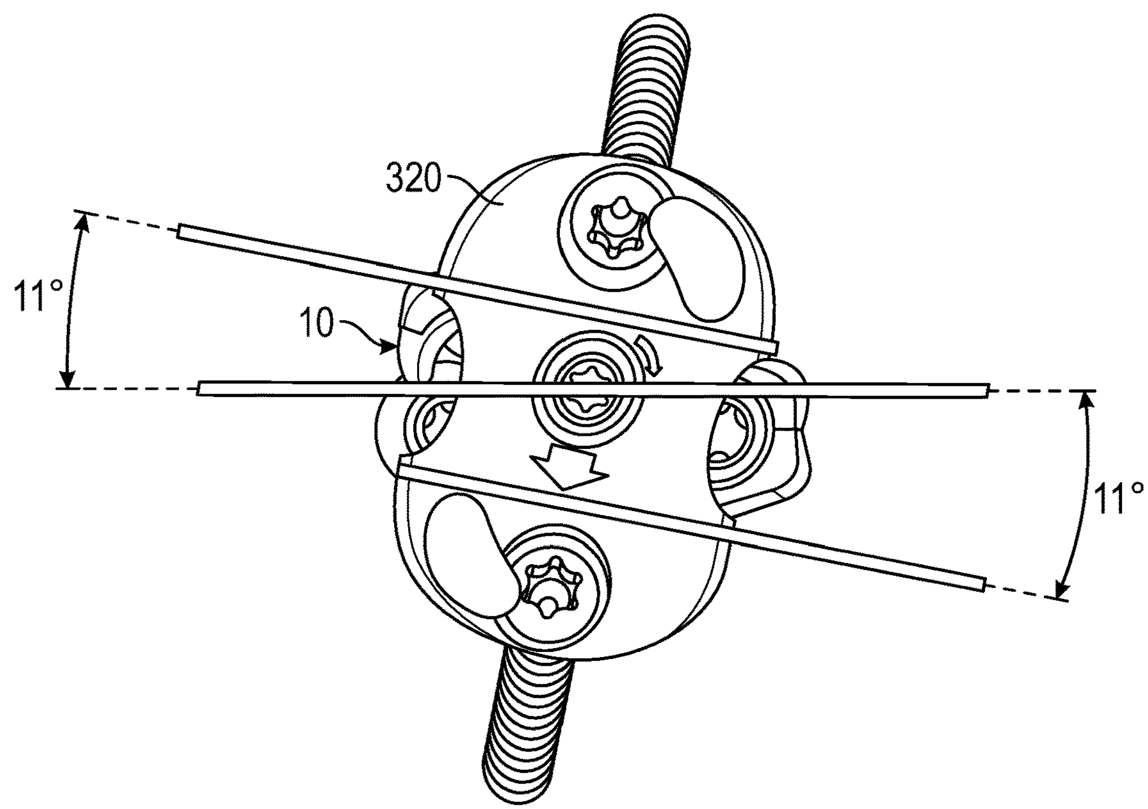

With reference to FIGS. 20A-20D, the spinal system 300 comprises an interbody fusion device 10 and a fixation assembly 310. The interbody fusion device 10 may be the same as or similar to the device 10 described above in conjunction with FIGS. 1A-1C. The fixation assembly 310 comprises a single fixation plate 320, at least a first fastener 322, and at least a second fastener 324. The single fixation plate 310 is provided with at least a first aperture 326 configured for insertion of the first fastener 322 therethrough to secure to a first vertebral body, and at least a second aperture 328 configured for insertion of the second fastener 324 therethrough to secure to a second vertebral body. The single fixation plate 320 is configured to be insertable to the interbody fusion device 10, allowing the single fixation plate 320 to be attached to the interbody fusion device 10 in situ. The single fixation plate assembly 320 may also be attached to the interbody fusion device 10 prior to implantation if desired, assuming the interbody fusion device is adjusted prior to implantation. The single fixation plate 320 may have an attachment-lock mechanism 340 configured to secure the attachment of the single fixation plate 320 to the interbody fusion device 10. According to certain embodiments, the single fixation plate 320 is rotatable relative to the interbody fusion device 10, either clockwise or counterclockwise, as shown in FIG. 20D. The ability of the single fixation plate 320 to rotate relative to the interbody fusion device 10 allows the locations of the first aperture 326 and the second aperture 328 to be adjusted relative to the vertebral bodies, thereby providing optimal fastener trajectories to increase purchase for the fasteners to the vertebral bodies.

With reference to FIGS. 21A-21F, the single fixation plate 320 is similar in many aspects to the single fixation plate 210 described above in connection with FIGS. 13A-13F. For instance, the single fixation plate 320 may include an attachment-lock mechanism 340, a first fastener-lock mechanism 342, and a second fastener-lock mechanism 344. The construction and operation of the attachment-lock mechanism 340 and the fastener-lock mechanisms 342 and 344 are the same as or similar to the attachment-lock mechanism 240 and the fastener-lock mechanisms 242 and 244 in the single fixation plate 210 shown FIGS. 13A-13F, therefore their detailed description is omitted herein for clarity.

Figure 21A:
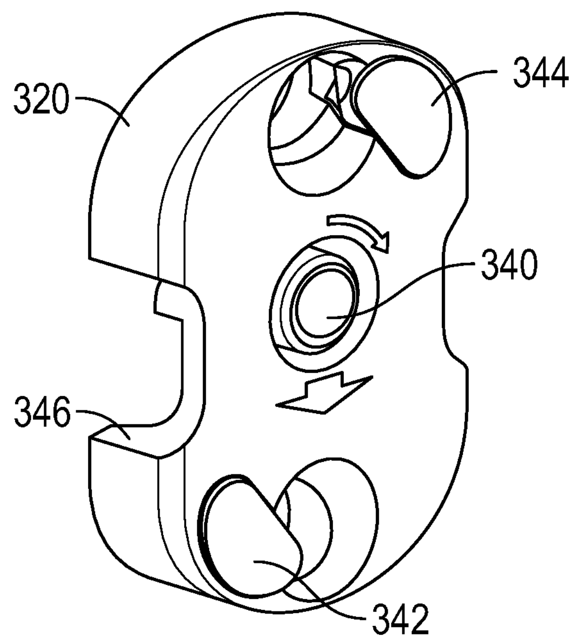
FIGS. 21A-21F depict an example single fixation plate according to embodiments of the disclosure.
Figure 21B:
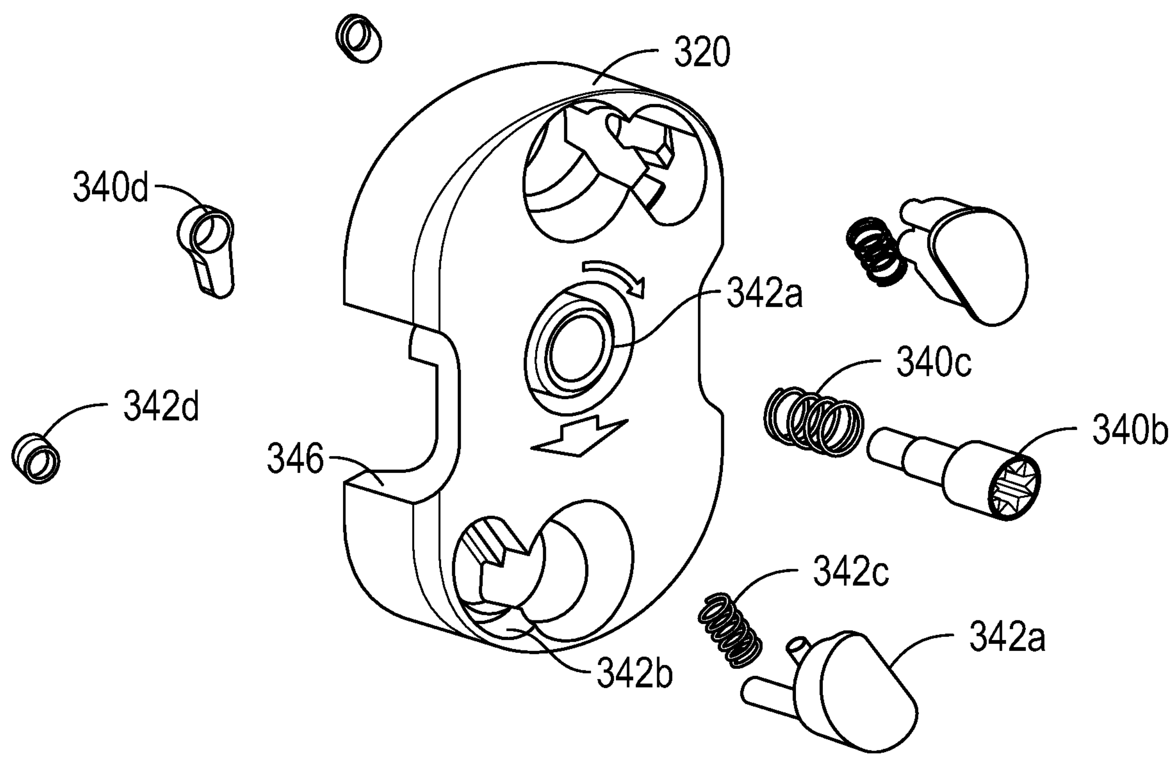
Figure 21F:
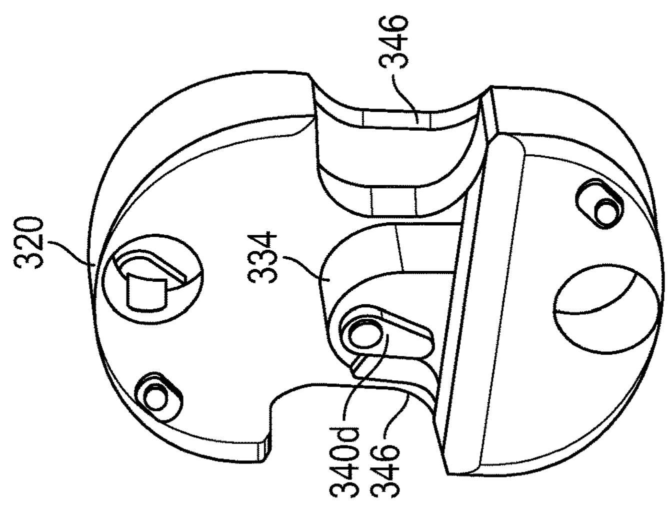
Figure 21E:
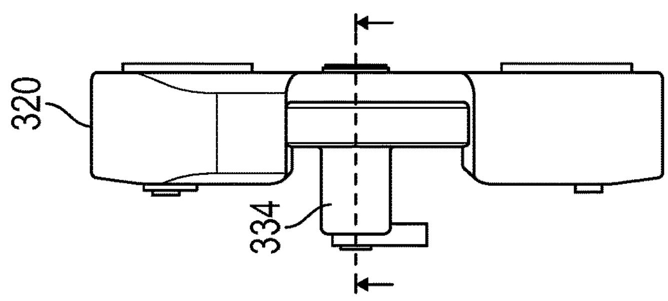
Figure 21D:
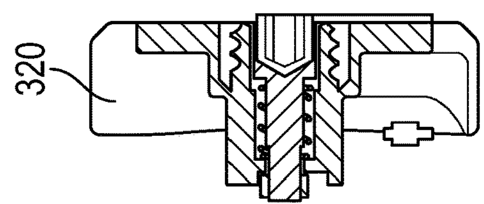
Figure 21C:
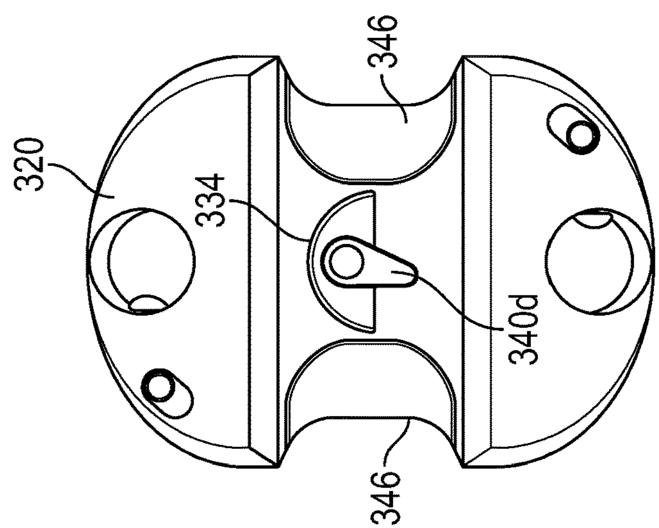
Figure 22B:
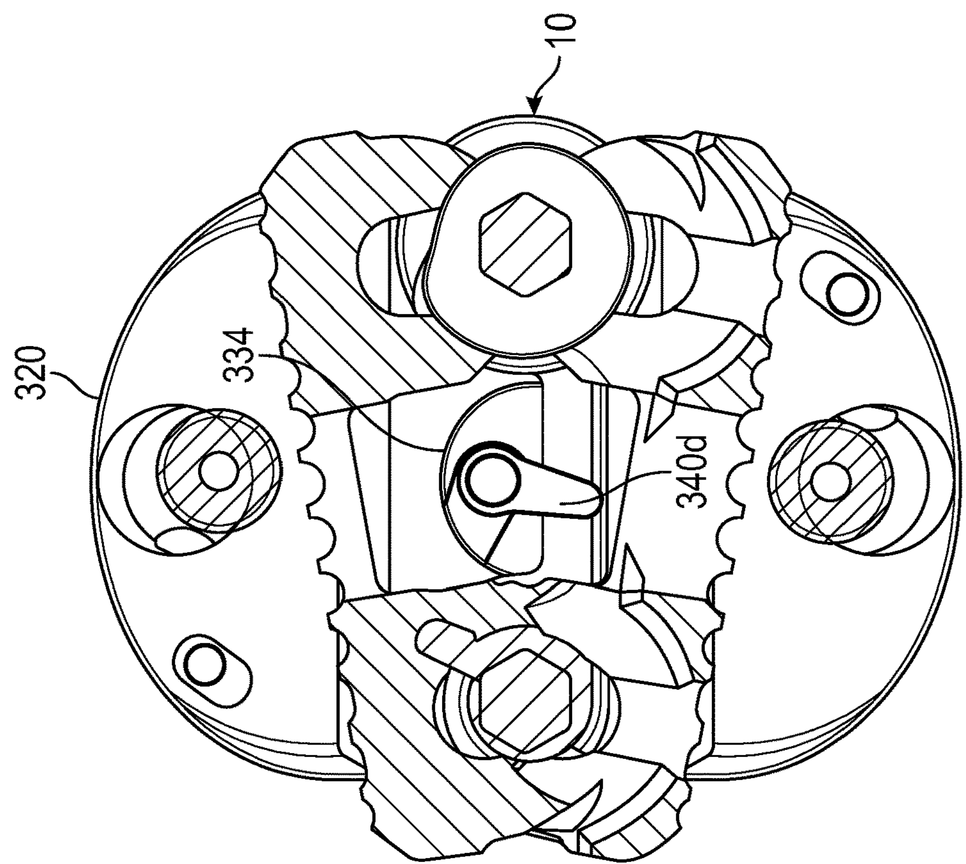
FIGS. 22A-22B show attachment of a single fixation plate to a dual-axis adjustable interbody fusion device.
Figure 22A:
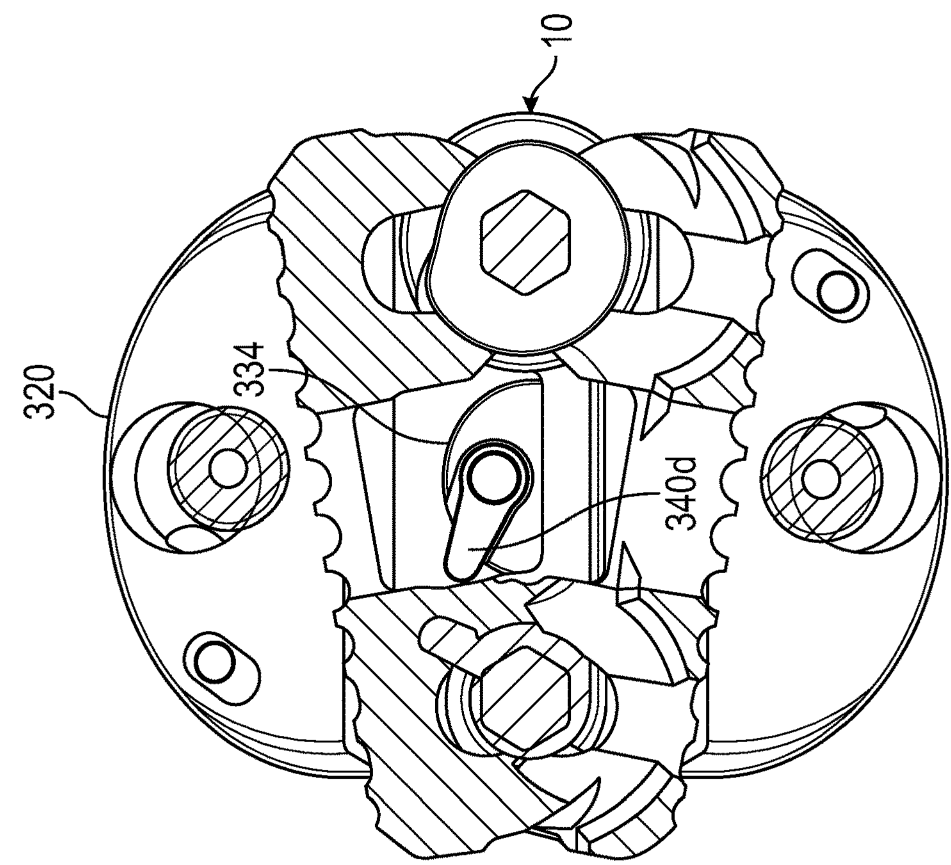

With reference to FIGS. 210-21F, the single fixation plate 320 may also include a protruding portion 334 configured to be insertable into the interbody fusion device 10, or allowing the single fixation plate 320 to be attached with the interbody fusion device 10 to stabilize and/or prevent migration of the interbody fusion device 10 placed between adjacent vertebrae. The attachment of the single fixation plate 320 to the interbody fusion device 10 restricts unwanted translational movement of the interbody fusion device 10 in any of the lateral, anterior, and posterior directions. The attachment of the single fixation plate 320 to the interbody fusion device 10 may be secured or locked by the attachment-lock mechanism 340, as shown in FIGS. 22A-22B. FIG. 22A shows the attachment of the single fixation plate 320 to the interbody fusion body 10 and the attachment-lock mechanism 340 in an unlocked state. FIG. 22B shows the attachment of the single fixation plate 320 to the interbody fusion body 10 and the attachment-lock mechanism 340 in a locked state, where the latch 340*d* of the attachment-lock mechanism 340 hooks to a component (e.g. the thrust bearing) in the interbody fusion device 10.

Figure 23B:
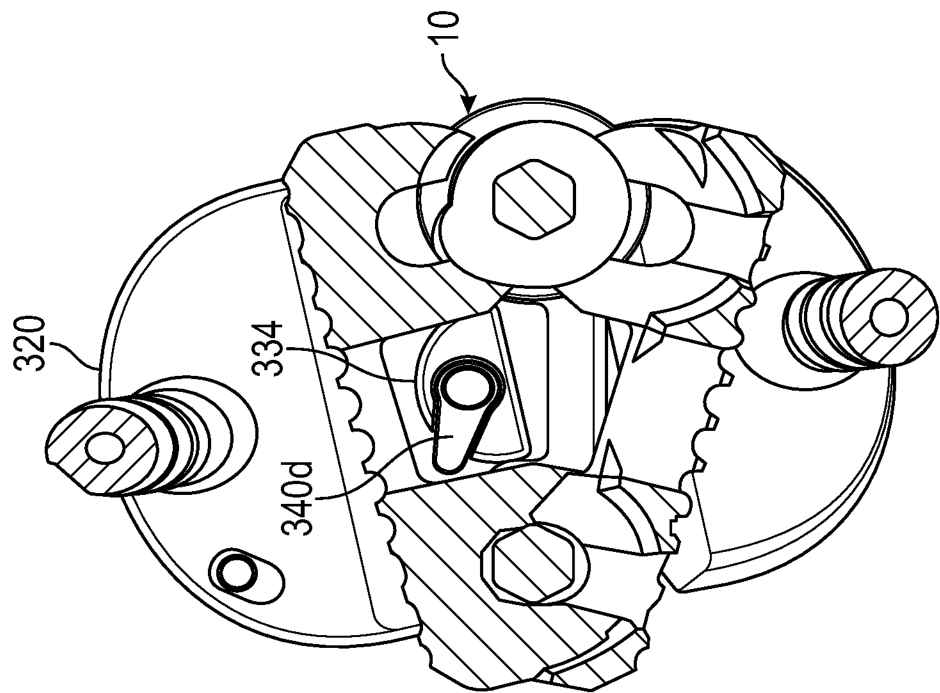
FIGS. 23A-23D show the ability for the single fixation plate depicted in FIGS. 21A-21F to angle relative to a dual-axis adjustable interbody fusion device according to embodiments of the disclosure.
Figure 23A:
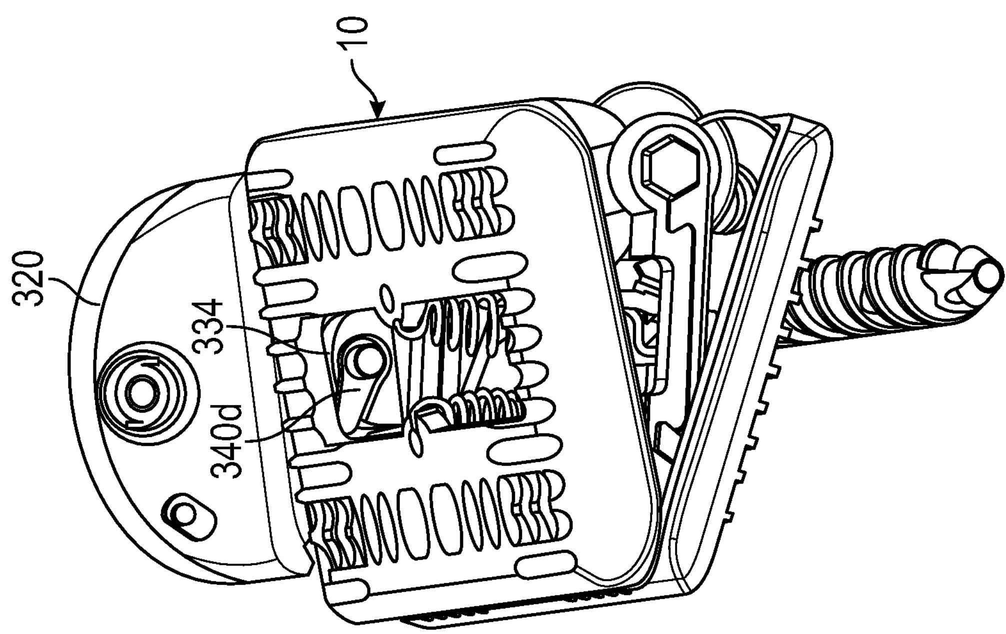
Figure 23C:
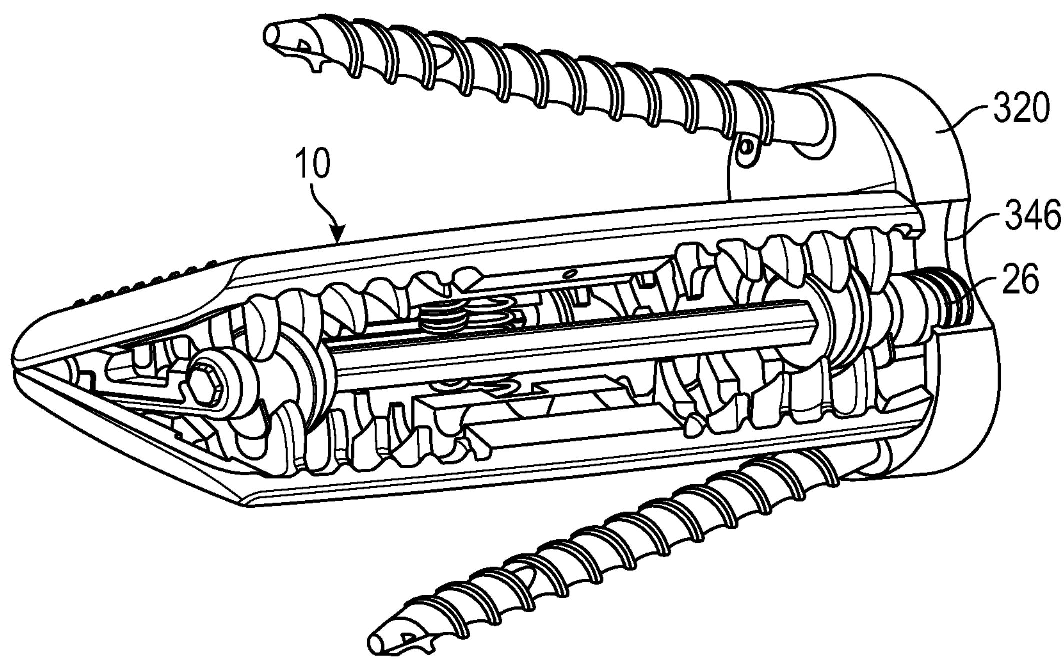
Figure 23D:
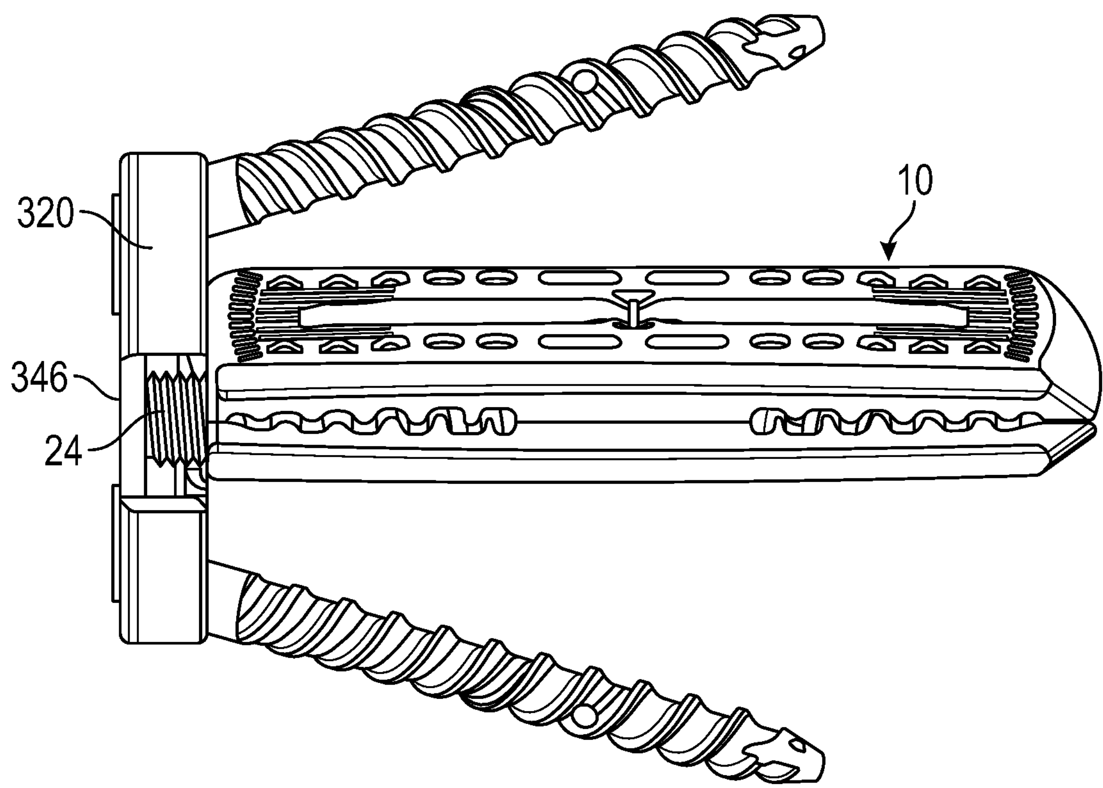

According to certain embodiments of the disclosure, the protruding portion 334 is configured to allow the single fixation plate 320 to be rotatable relative to the interbody fusion device 10. For instance, the protruding portion 334 may have a geometry generally in the shape of a semi-cylinder, which can be received in an internal component(s) such as a channel geometry built in the inner surface of the superior shell member 34 of the interbody fusion device 10. The semi-cylinder geometry of the protruding portion 334 allows the single fixation plate 320 to be rotatable relative to the interbody fusion device 10, thereby allowing the orientation or angle of the single fixation plate 320 to be adjusted before being fastened to the vertebral bodies. According to certain embodiments of the disclosure, the single fixation plate 320 can be rotated relative to an imaginary plane containing the first and second drive shafts 24, 26, clockwise or counterclockwise, at an angle from 0-11 degree. FIG. 23A is an end view showing the angulation of the single fixation plate 320 relative to the interbody fusion device 10. FIG. 23B is a cross-sectional view showing the angulation of the single fixation plate 320 relative to the interbody fusion device 10. The lateral sides of the single fixation plate 320 may be configured to accommodate the first and second drive shafts 24 and 26 of the interbody fusion device 10 when the single fixation plate 320 is rotated relative to the interbody fusion device 10. As shown in FIGS. 21A-21F, recess, cutout or the like 346 may be provided at the lateral sides of the single fixation plate 320 to allow for the angulation of the single fixation plate 320 relative to the interbody fusion device 10. FIGS. 23C-23D are isometric views showing the recess or cutout 346 in the lateral sides of the single fixation plate 320, allowing for the angulation of the single fixation plate 320 without interference with the drive shafts 24 and 26 in the interbody fusion device 10.

Figure 24A:
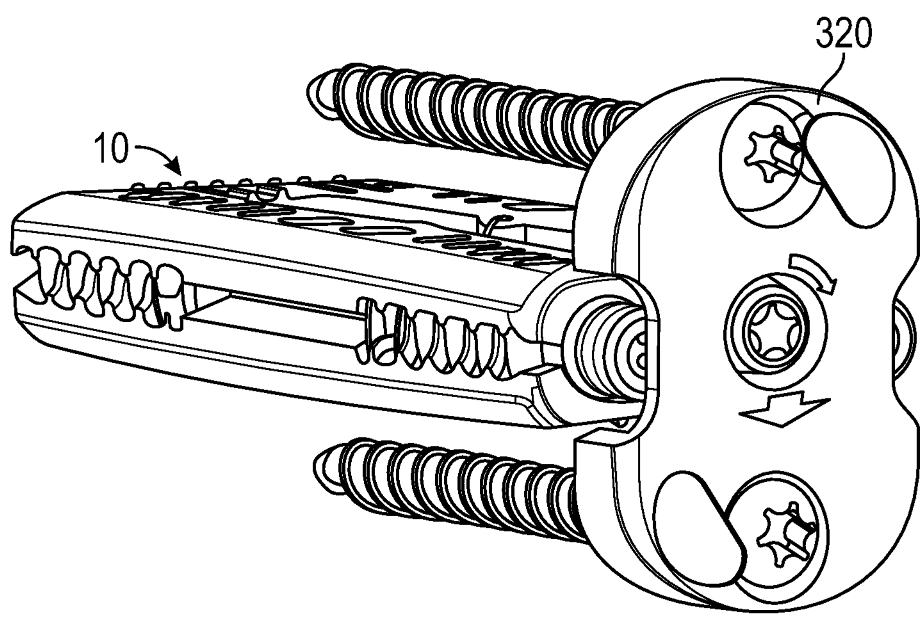
FIGS. 24A-24D show attachment of a single fixation plate to a dual-axis adjustable interbody fusion device in a contacted, an expanded, and a lordotically adjusted in configuration respectively.
Figure 24B:
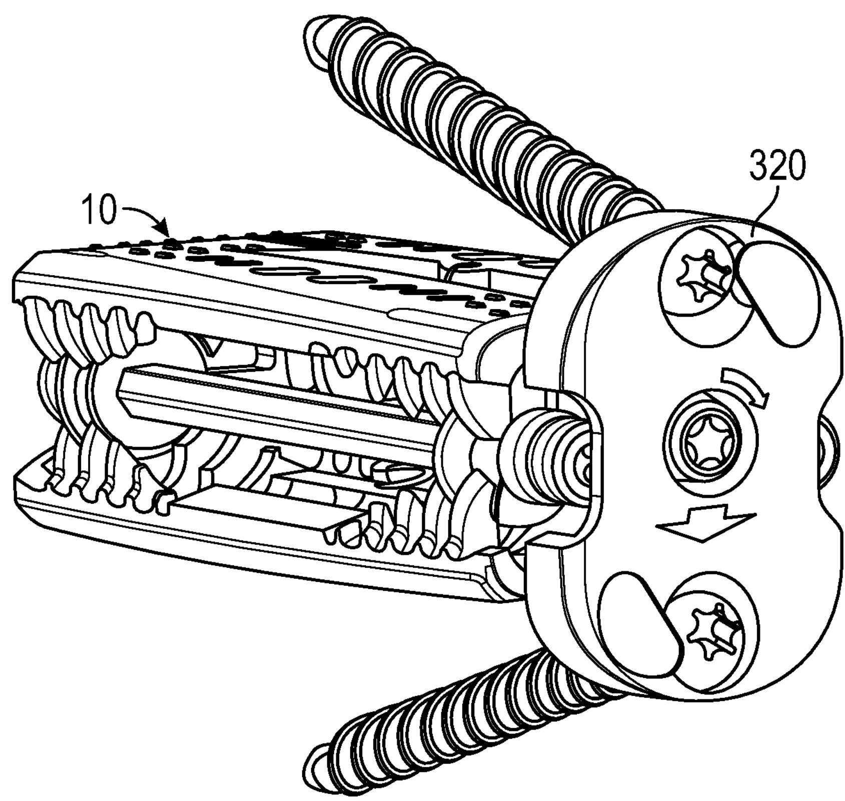
Figure 24C:
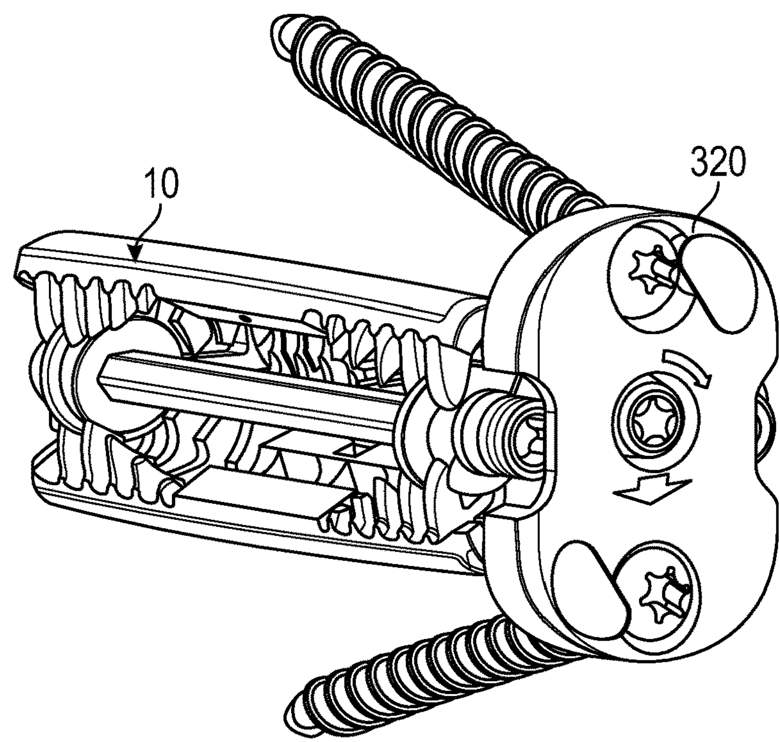
Figure 24D:
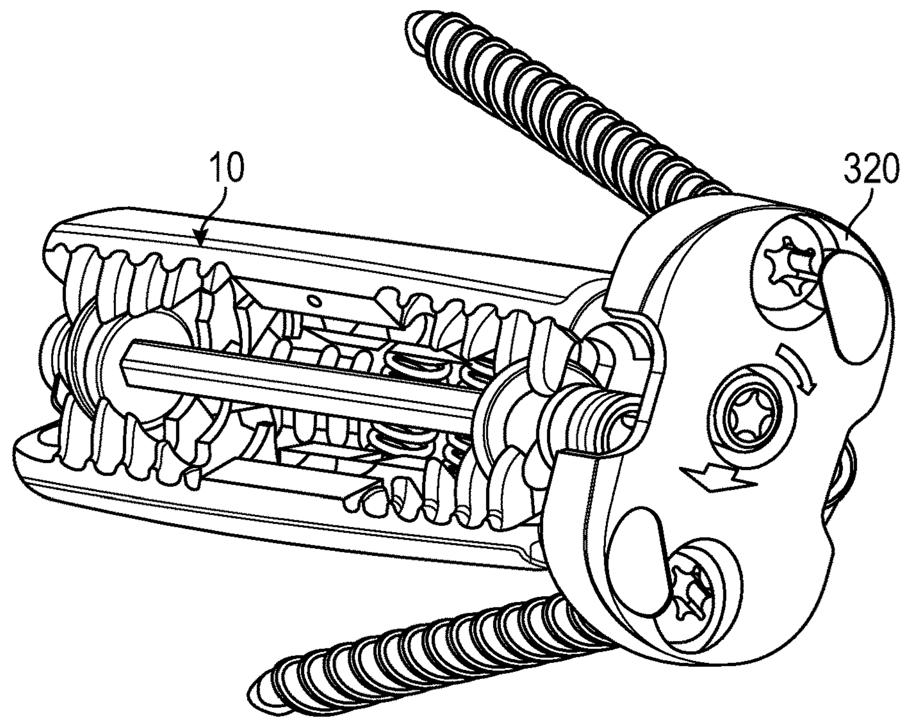

FIG. 24A-24D illustrate that the single fixation plate 320 can be attached to the interbody fusion device 10 in various configurations, including a contracted configuration, a fully expanded configuration, and a lordotically or hyperlordotically adjusted configuration respectively. By way of example where the interbody fusion device 10 is placed between adjacent vertebrae via a lateral surgical procedure, FIG. 24A shows that the single fixation plate 320 can be attached to the interbody fusion device 10 in a contracted configuration having an anterior height of 8.4 mm, a posterior height of 8.4 mm, and a lordosis of 0 degree. FIG. 24B shows an example where the single fixation plate 320 is attached to the interbody fusion device 10 in a fully expanded configuration having an anterior height of 16.1 mm, a posterior height of 16.1 mm, and a lordosis of 0 degree. FIG. 24C shows an example where the single fixation plate 320 is attached to the interbody fusion device 10 in a hyperlordotically adjusted configuration having an anterior height of 17.1 mm, a posterior height of 7.2 mm, and a lordosis of 30 degree. FIG. 24D shows an example where the interbody fusion device 10 in a hyperlordotically adjusted configuration having an anterior height of 17.1 mm, a posterior height of 7.2 mm, and a lordosis of 30 degree. In comparison of FIG. 24D with FIG. 24C, the single fixation plate 320 in FIG. 24D is rotated at an angle of 11 degree with respect to an imaginary plane containing the first and second drive shafts. The angulation of the single fixation plate 320 allows the position of the apertures 326, 328 in the single fixation plate 320 to be adjusted e.g. according to the expanded and/or lordotically adjusted configuration of the interbody fusion device 10, to provide for optimal fastener trajectories to the vertebral bodies.

Figure 25B:
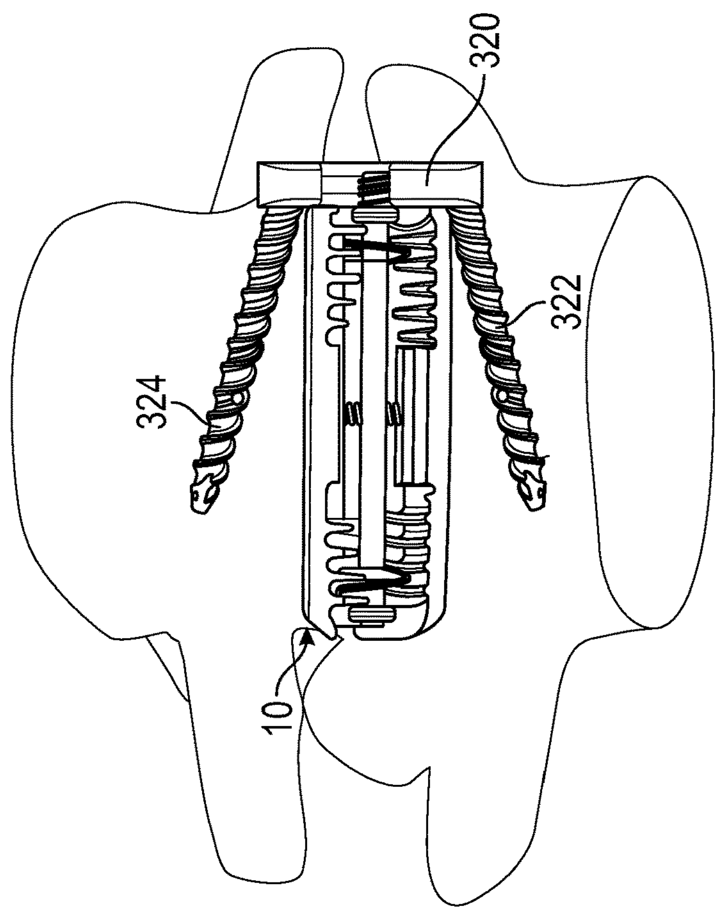
FIGS. 25A-25B show an example dual-axis adjustable interbody fusion device secured by a single fixation plate to adjacent vertebral bodies.
Figure 25A:
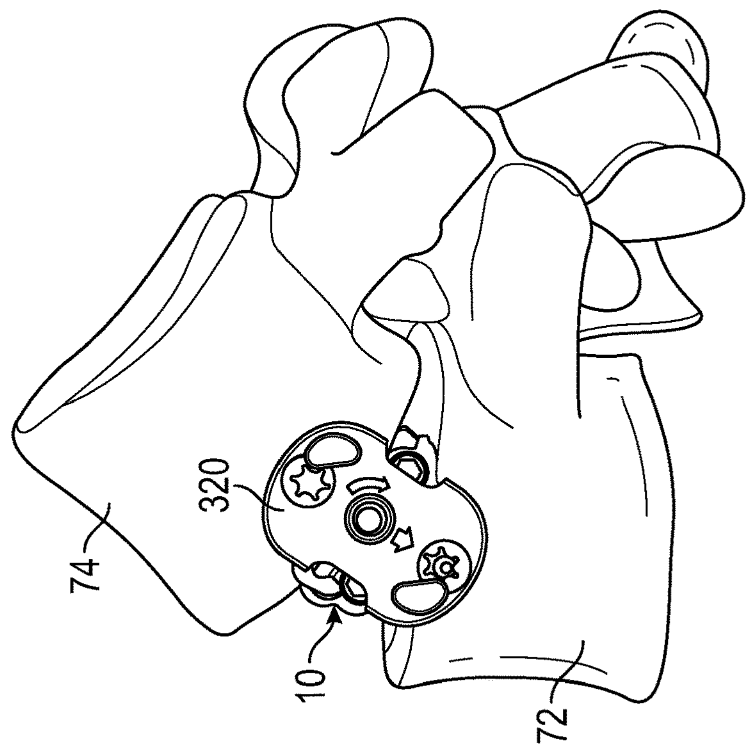

The dual-axis adjustable spinal system with 300 can be used for treatment of various spinal diseases including but not limited to degenerative disc disease (DDD), spondylolisthesis, retrolisthesis (Grade 1). Further, the fixation assembly 310 can also be used to provide supplemental fixation in treatment of degenerative disc disease (DDD), spondylolisthesis, trauma (fractures and dislocations), deformities of curvatures (scoliosis, kyphosis, and/or lordosis), tumor, pseudoarthrosis, and failed previous fusion, trauma, tumors, deformities, pseudoarthrosis, previous failed fusions, and so on. The use, benefits, and advantages of the single system 300 are similar to those provided by the spinal system 200 described above in conjunction with FIGS. 12A-19B, therefore the detailed description is omitted herein for clarity. One uniqueness is the variable aspect of the single fixation plate 320 in the spinal system 300. Because of the lack of male geometries mated with female geometries in the drive shafts, the single fixation plate 320 is capable of rotating relative to the interbody fusion device 10 in situ, allowing the locations of apertures in the single fixation plate 320 to be adjusted. FIGS. 25A-25B show an embodiment where the interbody fusion device 10 is secured in the vertebral bodies 72 and 74 by the single fixation plate 320.

Dual-Axis Adjustable Interbody Fusion Device with Integrated Fixation

With reference to FIGS. 26A-31B, embodiments of a dual-axis adjustable interbody fusion device with integrated fixation or apparatus 400 according to the disclosure will now be described. The integrated design allows the fixation plates to be implanted along with the interbody fusion device and angle-adjusted with the expansion and/or adjustment of the interbody fusion device in situ, providing stabilization and preventing migration of the interbody fusion device in the vertebral bodies.

As shown in FIGS. 26A-26D, the apparatus 400 in general comprises an interbody fusion device 10 and a fixation assembly 410. The interbody fusion device 10 may be the same as, or similar to, the example dual-axis adjustable interbody fusion device 10 described above in conjunction with FIGS. 1A-1C. Alternatively, the fusion device 10 can be any other dual-axis adjustable interbody fusion devices available from various manufacturers, which can be further adapted or modified for use with the fixation assembly 410.

The fixation assembly 410 comprises a first or inferior fixation plate 420 and a second or superior fixation plate 440. The fixation assembly 410 also comprises a first fastener 424 and a second fastener 442. According to certain embodiments of the disclosure, the inferior fixation plate 420 is coupled to the inferior shell member 32 and configured for placement with the interbody fusion device 10. Likewise, the superior fixation plate 440 is coupled to the superior shell member 34 and configured for placement with the interbody fusion device 10. In certain embodiments, the inferior fixation plate 420 can be integrally formed with the inferior shell member 32. For instance, the inferior fixation plate 420 and the inferior shell member 32 can be formed as a single part, or the inferior fixation plate 420 can be made as a separate piece and then welded to or integrated with the inferior shell member 32. Alternatively, the inferior fixation plate 420 may be formed as a separate part and coupled to the inferior shell member 32 by interference fit, screw coupling, or any other suitable means. Likewise, the superior fixation plate 440 can be integrally formed with the superior shell member 34 by e.g. being made as a single piece, or separate pieces and then welded together. Alternatively, the superior fixation plate 440 may be formed as a separate part and coupled to the superior shell member 34 by interference fit, screw coupling, or any other suitable means. The integrated design allows the inferior fixation plate 420 and the superior fixation plate 440 to be implanted along with the interbody fusion device 10. The coupling of the inferior fixation plate 420 with the inferior shell member 32 and of the superior fixation plate 440 with the superior shell member 34 allows the inferior fixation plate 420 and superior fixation plate 440 to be angle-adjusted with the expansion and/or adjustment of the interbody fusion device 10 in situ.

The inferior fixation plate 420 is provided with an aperture 424 configured for insertion of the first fastener 422 therethrough to secure to a first vertebral body. The superior fixation plate 440 is provided with an aperture 444 configured for insertion of the second fastener 444 therethrough to secure to a second vertebral body. According to certain embodiments of the disclosure, either or both of the inferior fixation plate 420 and the superior fixation plate 440 may be sized and/or shaped to minimize or reduce the profile of the fixation plates. A reduced profile of the inferior fixation plate 420 and/or the superior fixation plates 440 allows for improved visualization of the apparatus 400 inside the patient especially e.g. in a lateral view when implanted via a lateral approach. A reduced profile of the inferior fixation plate 420 and/or the superior fixation plates 440 also facilitates insertion and placement of the apparatus 400 in the patient anatomy. By way of example, either or both of the inferior fixation plate 420 and the superior fixation plates 440 may be in the form of a screw loop or bracket, wherein the fastener apertures 424 and/or 444 are formed or situated adjacent to the peripheral of the inferior fixation plate 420 and/or the superior fixation plate 440 so that the overall profile of the inferior fixation plate 420 and superior fixation plate 440 can be minimized.

Figure 26A:
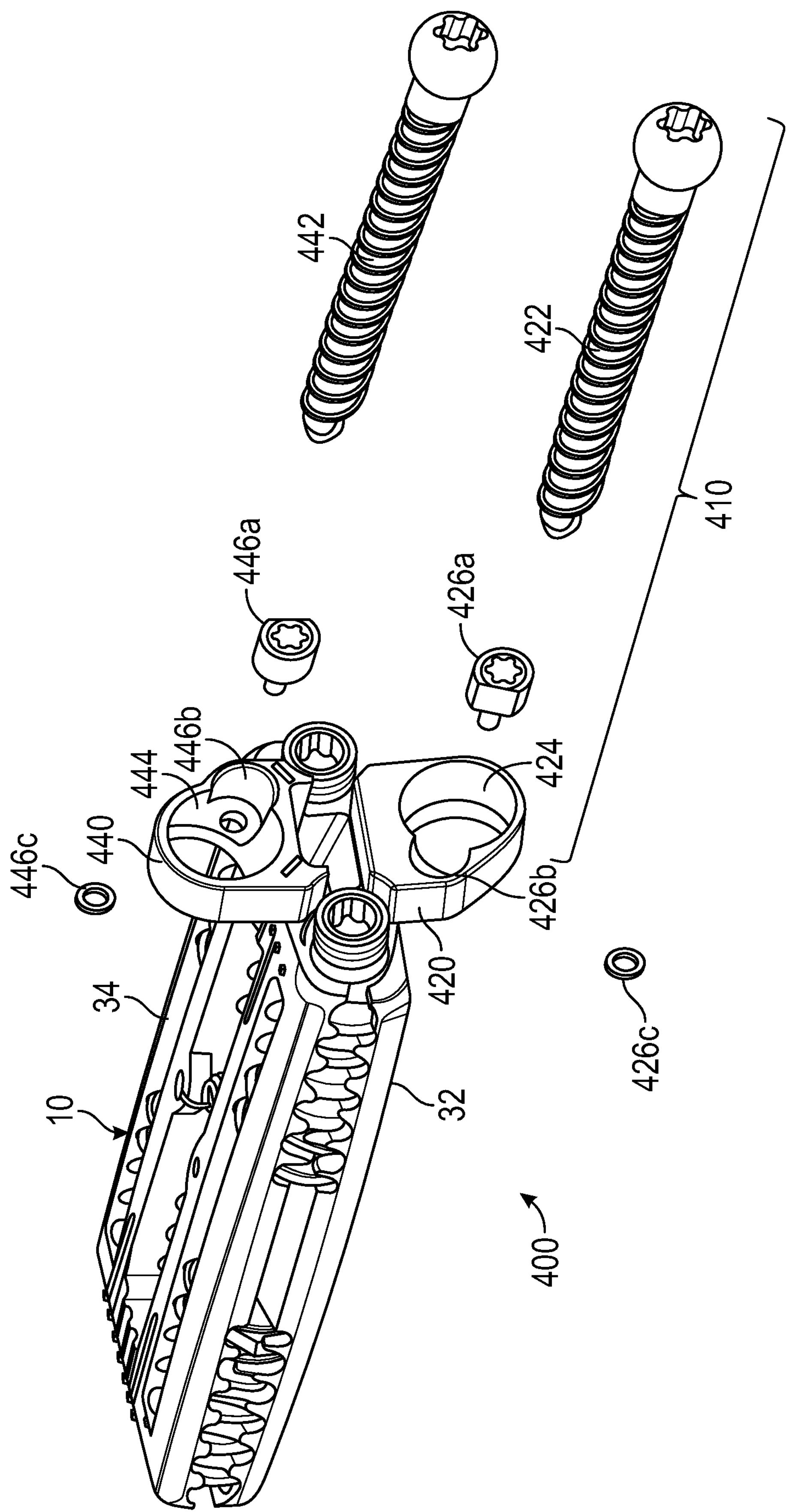
FIGS. 26A-26D depict an example dual-axis adjustable interbody fusion device with integrated fixation according to embodiments of the disclosure.
Figure 26B:
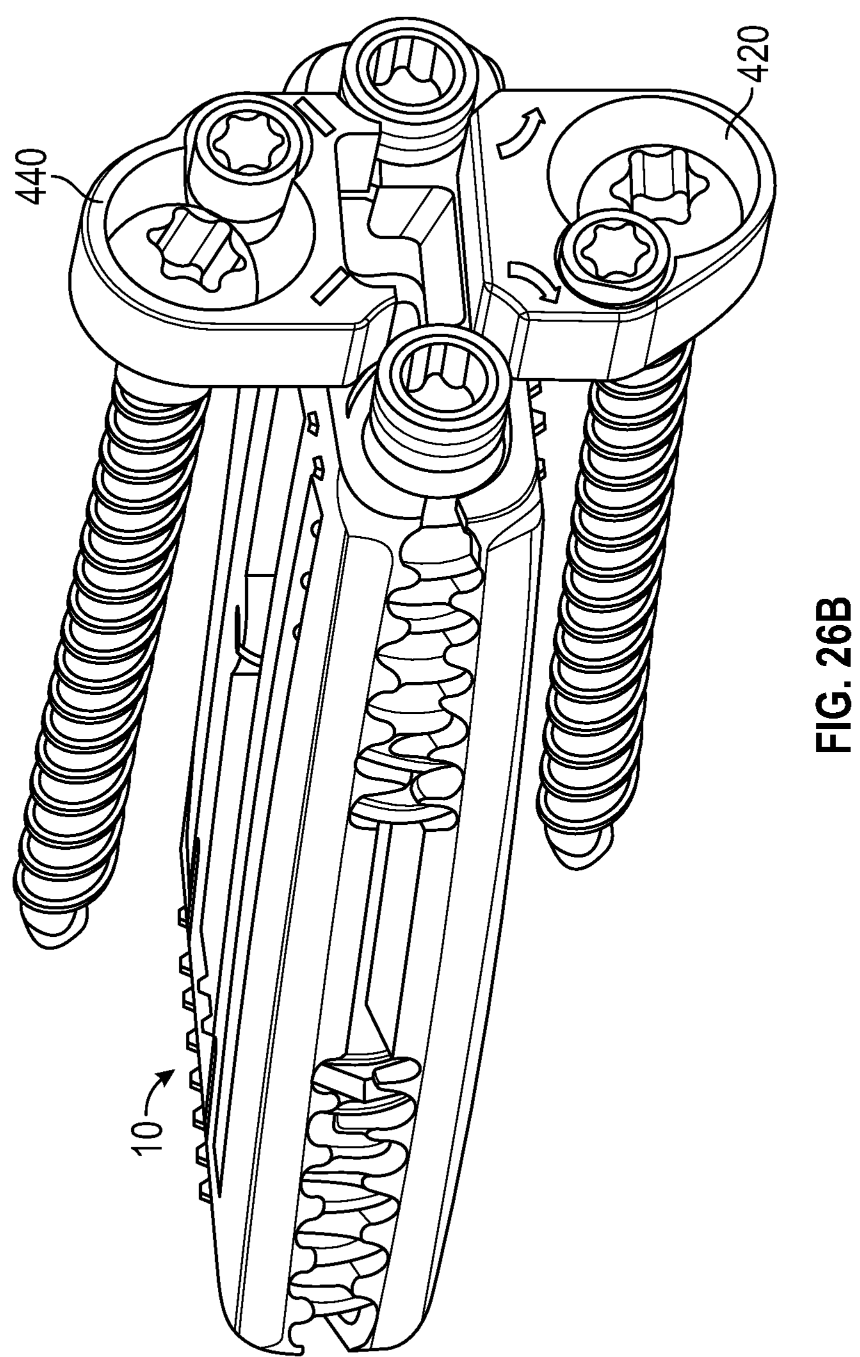
Figure 26D:
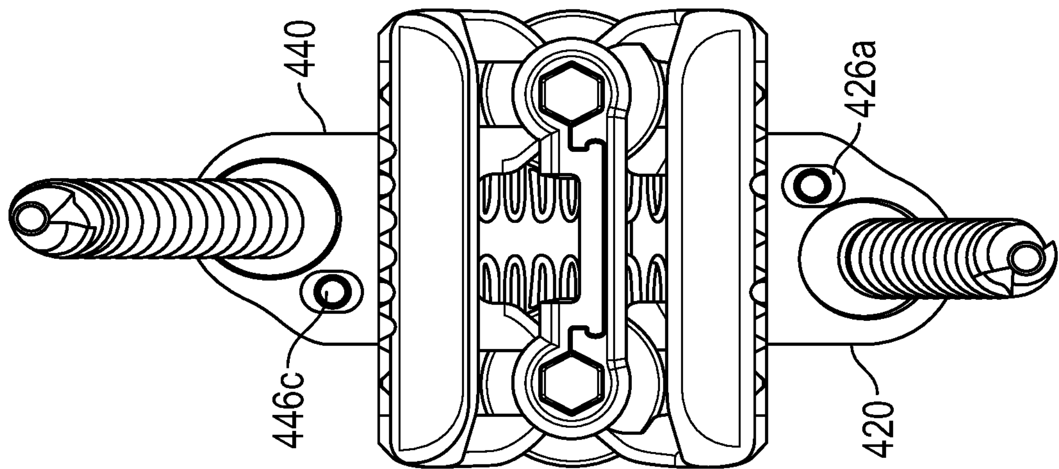
Figure 26C:
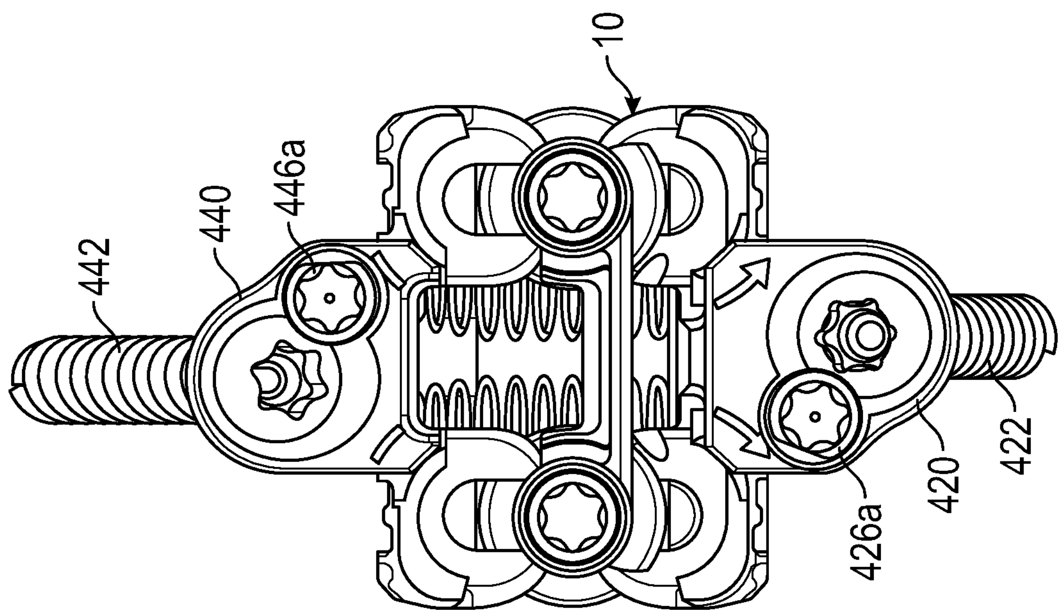
Figure 28:
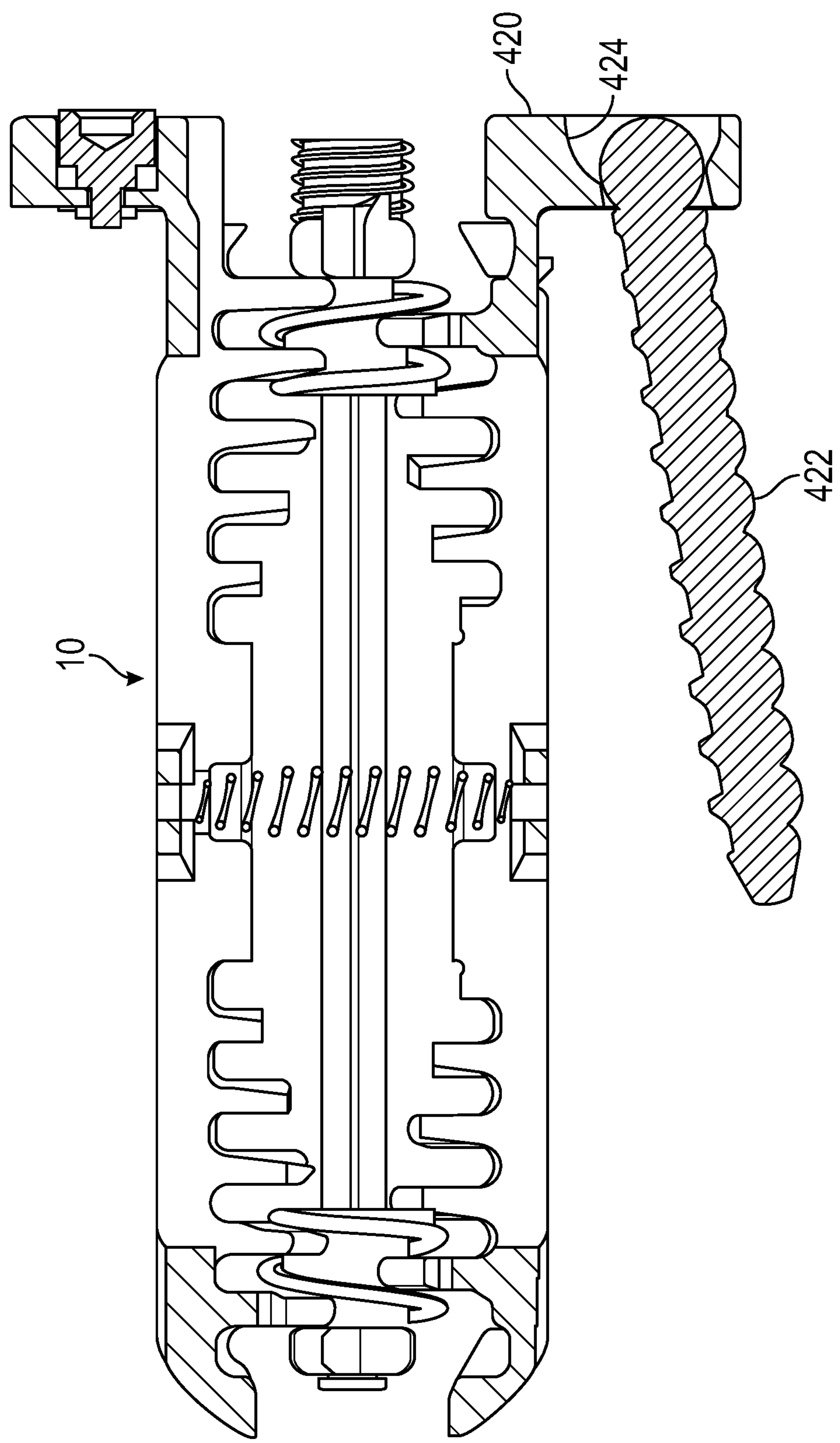
FIG. 28 is a cross-sectional view of an example dual-axis adjustable interbody fusion device with integrated fixation according to embodiments of the disclosure, emphasizing a fastener head received in a countersink of an aperture in the integrated fixation plate.

According to certain embodiments of the disclosure, the aperture 424 in the inferior fixation plate 420 and the aperture 442 in the superior fixation plate 440 may be configured to allow the trajectory of the first fastener 422 and the second fastener 442 to be adjustable in a caudal or cephalad direction as shown in FIGS. 26C-26D. By way of example, the aperture 424 in the inferior fixation plate 420 and the aperture 444 in the superior fixation plate 440 can be cut such that the centerlines of the apertures 424 and 444 form an angle of e.g. 0-15 degrees relative to a reference plane such as the inferior shell member or the superior shell member, as described above in conjunction with FIGS. 16A-16B. Alternatively, or additionally, the first fastener 422 and the second fastener 442 may be sized or shaped to allow the fastener trajectory to be adjustable. For example, the first and second fasteners 422, 442 may have a head portion in a spherical or tapered shape as shown in FIG. 28, allowing for an adjustable fastener trajectory. In general, the trajectory of the first fastener 422 and the second fastener 442 is capable of being angled from 0-15 degrees relative to the inferior shell member 32 or superior shell member 34 respectively, e.g. in a caudal or cephalad direction, providing an optimal fastener trajectory to maximize or increase the purchase for the fastener to the vertebral bodies.

Figure 27A:
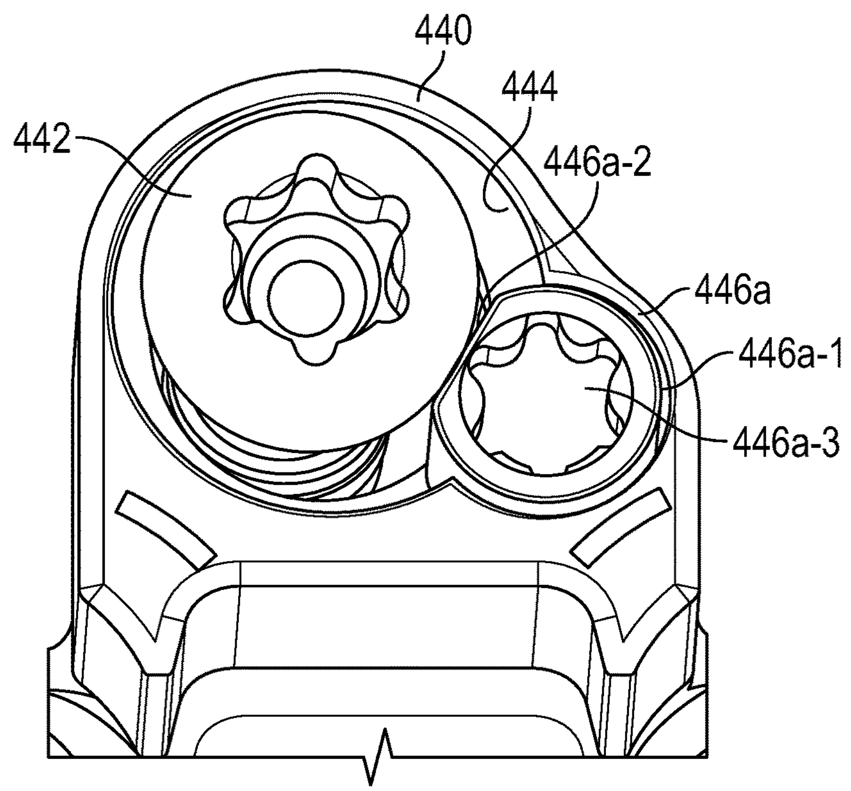
FIGS. 27A-27B depict an example fastener-lock mechanism according to embodiments of the disclosure.
Figure 27B:
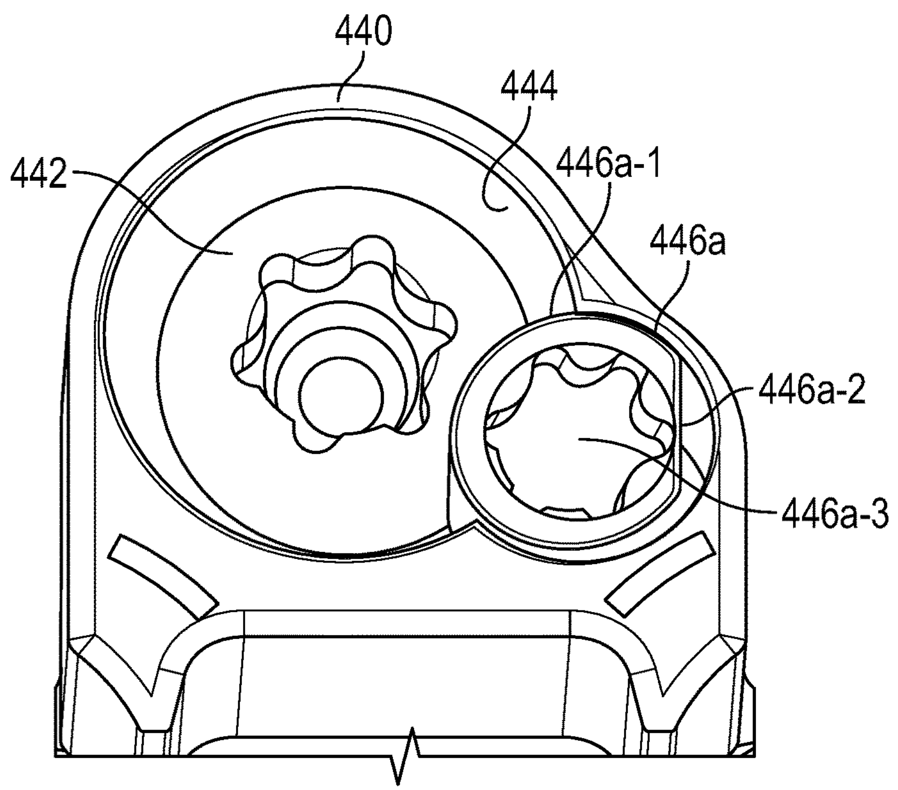

With reference to FIGS. 26A-26D, the inferior fixation plate 420 may include a lock mechanism 426 for preventing the fastener 422 from backing out. Likewise, the superior fixation plate 440 may include a lock mechanism 446 for preventing the fastener 442 from backing out. The lock mechanism 426 in the inferior fixation plate 420 may be the same as or similar to the lock mechanism 446 in the superior fixation plate 440. For example, the lock mechanism 446 in the superior fixation plate 440 may include a lock rod **446*a* received in a recess 446*b* adjacent to the aperture 444 in the superior fixation plate 440, and an adapter 446*c* welded or attached to an end of the lock rod 446*a* to retain the lock rod in the recess and allow the lock rod to turn. As better viewed in FIGS. 27A-27B, the head of the lock rod 446*a* may have a rounded side portion 446*a*-1, a flat side portion 446*a*-2, and an end 446*a*-3 having a feature such as a female hexalobe feature configured to receive a driver for actuating the lock mechanism 446. When the lock rod 446*a* is turned to set the lock mechanism 446 to an unlocked or open state, the head flat side portion 446*a*-2 faces the aperture 444 in the fixation plate 440 as shown in FIG. 27A, leaving the aperture 444 open to allow the fastener 442 to insert through. After the fastener 442 is driven all the way through into a vertebral body and the fastener head received in the countersink of the aperture as shown in FIG. 27B, the lock rod 446*a* can be turned to set the lock mechanism 446 in a locked state, where the head rounded side portion 446*a*-1 extends over at least a portion of the aperture 444 or over the fastener 442, prohibiting the fastener 442 from backing out. The lock mechanism 446 of the disclosure allows quick "one-step" locking, requiring only one turn of the lock rod 446*a*** with a driving tool to lock or unlock the fastener. The use of a "one-step" locking mechanism can also simplify or reduce the profile of the fixation plate, which is beneficial for inserting and placing the apparatus in the patient anatomy.

Figure 29A:
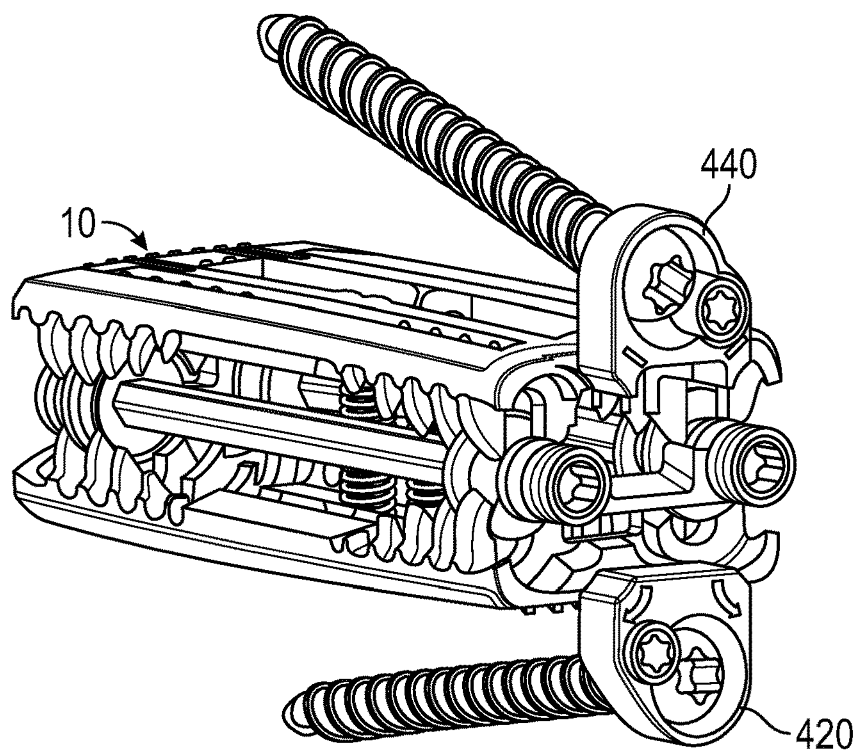
FIGS. 29A-29B show angulation of integrated fixation plates in an example dual-axis adjustable interbody fusion device in an expanded and a lordotically adjusted configuration respectively.
Figure 29B:
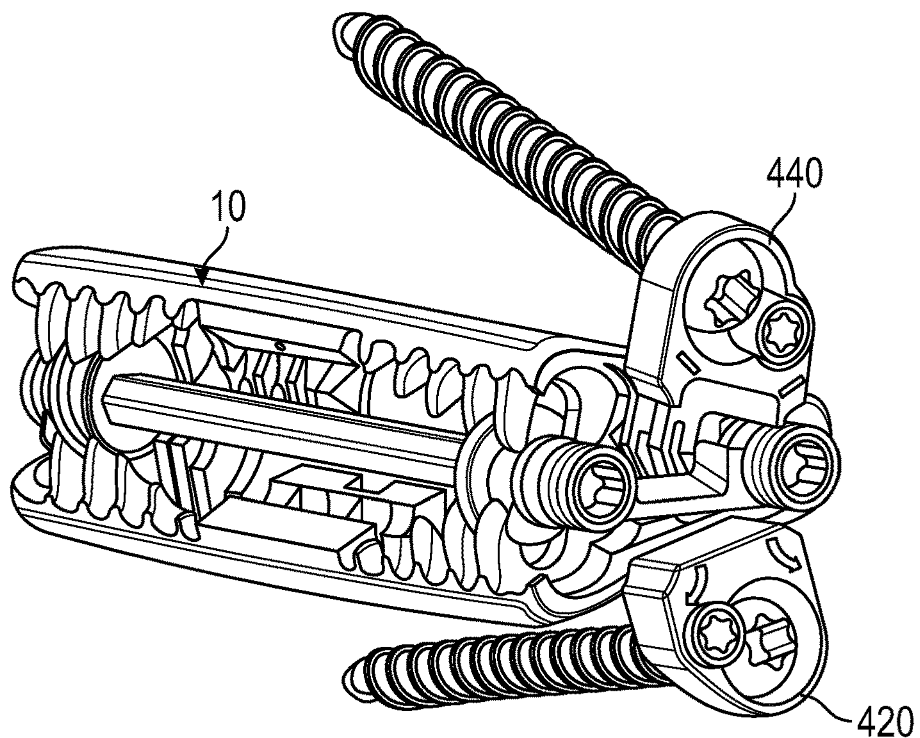

With reference now to FIGS. 29A-29B, the integrated fixation plates 420, 440 of the disclosure can stabilize and prohibit migration of the interbody fusion device 10 in any expanded or adjusted configurations in the adjacent vertebrae. FIG. 29A shows an embodiment where the example interbody fusion device 10 is in a fully expanded configuration having an anterior height of 16.1 mm, a posterior height of 16.1, and a lordosis of 0 degree. FIG. 29B shows an embodiment where the example interbody fusion device 10 is in a hyperlordotically adjusted configuration having an anterior height of 17.1 mm, a posterior height of 7.2, and a lordosis of 30 degree. While kyphotic (negative lordosis) adjustments may not be desirable for the lumbosacral segment of the spine, the interbody fusion device 10 can be hyperkyphotically adjusted. The inferior fixation plate 420 and the superior fixation plate 440 move with the inferior shell member 32 and the superior shell member 34 during the expansion and/or lordotic adjustment of interbody fusion device 10, allowing the position and/or angle of the apertures in the inferior and superior fixation plates 420, 440 to be automatically adjusted. In either of the device configurations shown in FIGS. 29A-29B, the fastener trajectory can be further varied at an angle from 0 to 15 degrees, e.g. in a caudal or cephalad direction, allowing for an optimal fastener trajectory to maximize or increase the purchase for the fastener to the vertebral body. FIG. 26B shows an embodiment where the interbody fusion device 10 is in a contracted configuration having an anterior height of 8.4 mm, a posterior height of 8.4 mm, and a lordosis of 0 degree.

Figure 30:
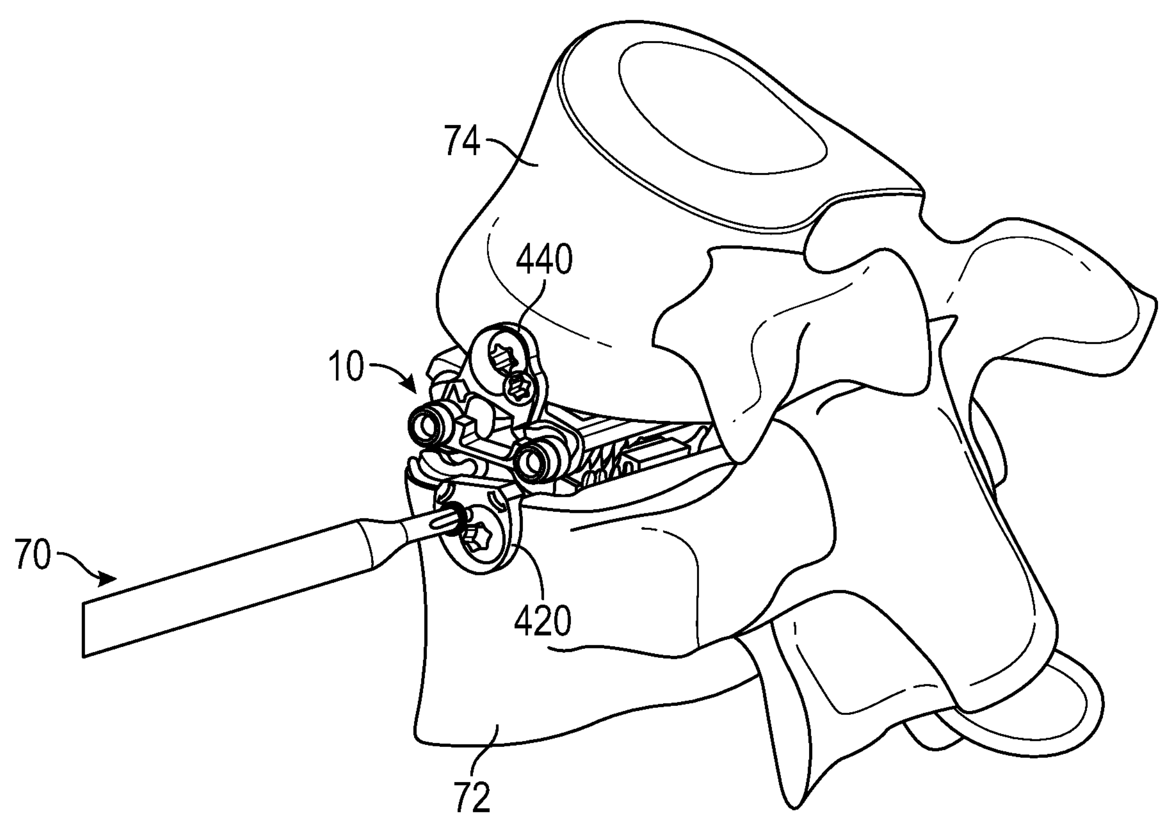
FIG. 30 shows securing an example dual-axis adjustable interbody fusion device with integrated fixation to adjacent vertebral bodies using an operation instrument.

The dual-axis adjustable interbody fusion device with integrated fixation 400 can be used in treatment of various spinal diseases, including but not limited to degenerative disc disease (DDD), spondylolisthesis, retrolisthesis (Grade 1), and so on. With reference to FIG. 30, in use the interbody fusion device with integrated fixation 400 in a contracted configuration can be inserted in the patient anatomy and placed between adjacent vertebrae 72, 74 using a suitable operation instrument 70. Suitable surgical procedure for introducing the interbody fusion device in the patent anatomy include a lateral lumbar interbody fusion (LLIF) procedure, an anterior lumbar interbody fusion (ALIF), posterior lumbar interbody fusion (PLIF) procedure, and any other suitable surgical procedures performed in the lumbar or other regions of the spinal column. Various suitable operation instruments are described in U.S. Ser. No. 15/661,435 filed Jul. 17, 2017 entitled "Surgical Operating Instrument for Expandable and Adjustable Lordosis Interbody Fusion Systems" and U.S. Ser. No. 16/035,637 filed Jul. 15, 2018 entitled "Surgical Operating Instrument for Expandable and Adjustable Lordosis Interbody Fusion Systems," the disclosures of all of which are incorporated herein in their entirety. The interbody fusion device 10 can be expanded and/or lordotically adjusted using the operation instrument 40, forming a suitable configuration between the adjacent vertebrae 72, 74.

Figure 31B:
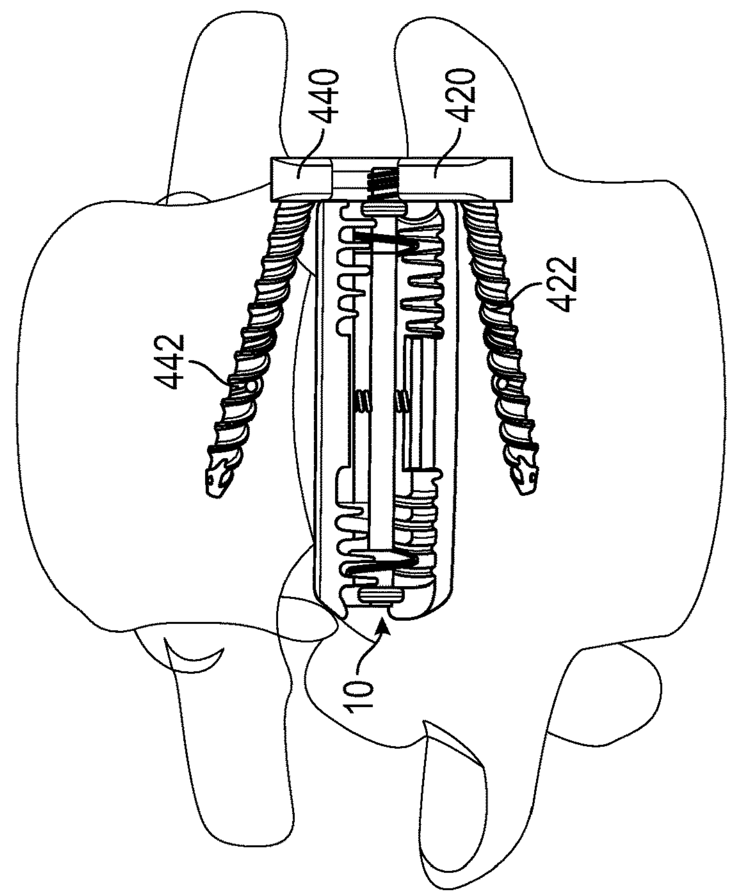
FIGS. 31A-31B show an example dual-axis adjustable interbody fusion device with integral fixation plates fastened to adjacent vertebral bodies.
Figure 31A:
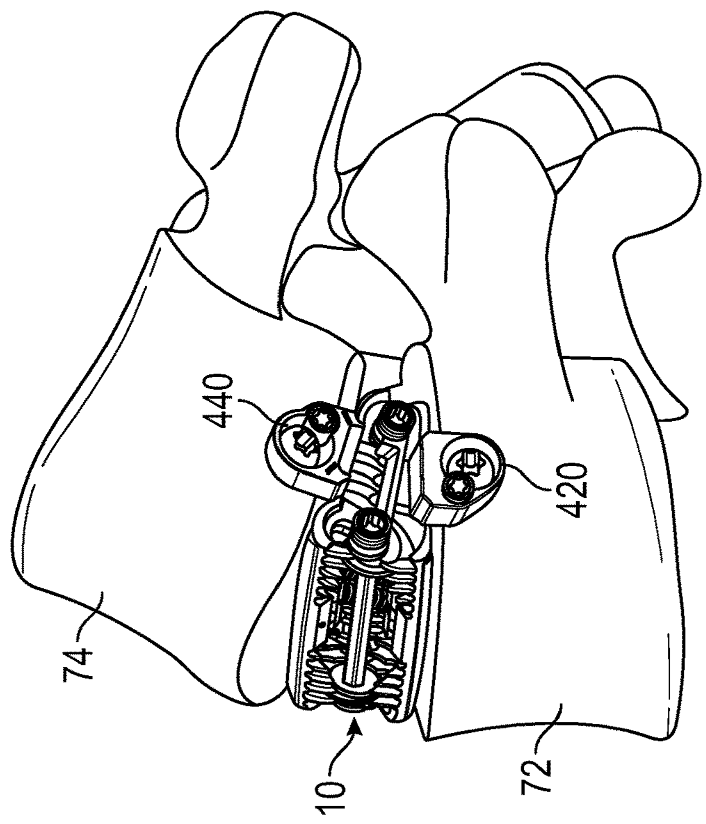

Fasteners such as bone screws 422, 442 can be then inserted through the apertures in the inferior and superior fixation plates 420, 440 and driven into the first vertebral body 72 and the second vertebral body 74 respectively. Once the fasteners 422, 442 are driven all the way and the heads of the fasteners are received in the apertures in the fixation plates, the "one-step" lock mechanisms in the inferior and superior fixation plates 420, 440 can be actuated using the operation instrument 70 to lock the fasteners 422, 442 to prevent them from backing out. The interbody fusion device 10 can be then stabilized and prevented from migrating in the vertebral bodies 72, 74, as shown in FIGS. 31A-31B.

Embodiments of a dual-axis adjustable interbody fusion device with integrated fixation 400 are described in conjunction with FIGS. 26A-31B. Beneficially, the interbody fusion device with integrated fixation 400 can stabilize and prohibit migration of an interbody fusion device in any configuration, from a less expanded configuration to a fully expanded configuration and/or hyperlordotically adjusted configurations to safely promote fusion between two adjacent vertebral bodies. Interbody fusion devices of any size and configuration can be integrated with the fixation plates of the disclosure and configured to be insertable via a single surgical approach and patient position to minimize disruption to the patient anatomy. The integration of inferior and superior fixation plates with an interbody fusion device allows angulation of the fastener aperture and thus the fastener trajectory to follow the angulation of the inferior and superior shell members of the interbody fusion device respectively, at any angle from 0-15 degrees, providing for ideal fastener trajectory and placement. Other benefits and advantages are same as or similar to those provided by the interbody fusion device with modular fixation 100 described above in connection with description of the FIGS. 2A-11B, and their detailed description is omitted herein.

According to embodiments of the disclosure, the first and second drive shafts 24 and 26 of the interbody fusion device 10 in the apparatuses 100 and 400 or in the systems 200 and 300 can be continuously operable to allow the distance between the inferior and superior shell members 32 and 34 at the first and/or second lateral areas of the housing to be continuously changeable, thereby allowing the height of the expanded configuration of the interbody fusion device 10 to continuously change. By way of example, the height of the interbody fusion device 10 can continuously change by 0 to 10 millimeters. Additionally, or alternatively, the first and second drive shafts 24 and 26 of the interbody fusion device 10 in the apparatuses 100 and 400 or in the systems 200 and 300 can be continuously operable to allow the angle between the inferior and superior shell members 32 and 34 to be continuously changeable, thereby allowing the lordosis of the expanded configuration of the interbody fusion device 10 to continuously change. By way of example, the lordosis of the interbody fusion device 10 can continuously from 0 to 30 degrees.

All technical and scientific terms used herein have the meaning as commonly understood by one of ordinary skill in the art unless specifically defined otherwise. As used in the description and appended claims, the singular forms of “a,” “an,” and “the” include plural references unless the context clearly dictates otherwise. The term “or” refers to a nonexclusive “or” unless the context clearly dictates otherwise. The term “first” or “second” is used to distinguish one element from another in describing various similar elements and should not be construed as in any particular order unless the context clearly dictates otherwise.

Those skilled in the art will appreciate that various other modifications may be made. All these or other variations and modifications are contemplated by the inventors and within the scope of the invention.

The invention claimed is:

1. An apparatus comprising an interbody fusion device and a fixation assembly, wherein the interbody fusion device comprising a housing, a first wedge member, a second wedge member, a first drive shaft, and a second drive shaft, wherein the housing comprises a first shell member and a second shell member, the first and second shell members engaging the first wedge member along a first lateral area of the housing, and engaging the second wedge member along a second lateral area of the housing, the first wedge member is provided with a through-opening configured to allow the first drive shaft to pass, the second wedge member is provided with a through-opening configured to allow the second drive shaft to pass, and the first drive shaft is operable to drive the first wedge member along the first lateral area of the housing, the second drive shaft is operable to drive second wedge member along the second lateral area of the housing, causing the first and second shell members to move relative to each other providing an expanded configuration of the interbody fusion device; and the fixation assembly comprising a first fixation plate having a first aperture for insertion of a first fastener, wherein the first fixation plate is modular and configured to be attachable to the interbody fusion device, thereby allowing the first fixation plate to be attached to the interbody fusion device in the expanded configuration in situ and fastened to a first vertebral body to stabilize and/or prevent migration of the interbody fusion device.

2. The apparatus of claim 1, wherein the fixation assembly further comprises a second fixation plate having a second aperture for insertion of a second fastener, the second fixation plate being modular and configured to be attachable to the interbody fusion device, thereby allowing the second fixation plate to be attached to the interbody fusion device in the expanded configuration in situ and fastened to a second vertebral body to stabilize and/or prevent migration of the interbody fusion device.

3. The apparatus of claim 2, wherein the first fixation plate comprises a male geometry, the first drive shaft of the interbody fusion device comprises an end portion having a female geometry, wherein the male geometry of the first fixation plate and the female geometry of the first drive shaft of the interbody fusion device are configured to have complementary mating features, whereby when the first fixation plate is attached to the interbody fusion device, the male geometry of the first fixation plate engages the female geometry of the first drive shaft of the interbody fusion device, thereby restricting an unwanted rotation of the first drive shaft.

4. The apparatus of claim 3, wherein the first fixation plate is provided with a channel geometry configured to receive an end portion of the second drive shaft of the interbody fusion device, the channel geometry extending from a first end to a second end of the channel geometry allowing the second drive shaft to be received at a position between the first end and the second end while the first fixation plate is pivoting about the first drive shaft of the interbody fusion device, whereby a position of the first aperture in the first fixation plate is capable of being adjusted with respect to the first vertebral body.

5. The apparatus of claim 4, wherein the channel geometry is configured to allow the first fixation plate to pivot about the first drive shaft of the interbody fusion device up to 15 degrees.

6. The apparatus of claim 4, wherein the first fixation plate comprises an attachment-lock mechanism engageable to lock the interbody fusion device.

7. The apparatus of claim 6, wherein the attachment-lock mechanism of the first fixation plate comprises a lock housing, a rod having a first end portion and a second end portion, a compression spring loaded on the rod and retained in the lock housing, and a latch coupled to the second end portion of the rod, wherein the latch engages the first drive shaft of the interbody fusion device when the attachment-lock mechanism of the first fixation plate is actuated in a locked state.

8. The apparatus of claim 2, wherein the second fixation plate comprises a protruding portion configured to be insertable into the interbody fusion device, the protruding portion having a geometry configured to be received in a feature in the second shell member of the interbody fusion device, thereby restricting an unwanted movement of the interbody fusion device.

9. The apparatus of claim 8, wherein the second fixation plate comprises an attachment-lock mechanism engageable to lock the interbody fusion device.

10. The apparatus of claim 9, wherein the attachment lock mechanism of the second fixation plate comprises a lock housing, a rod having a first end portion and a second end portion, a compression spring loaded on the rod and retained in the lock housing, and a latch coupled to the second end portion of the rod, wherein the latch hooks to a feature in the second shell member of the interbody fusion device when the attachment-lock mechanism of the second fixation plate is actuated in a locked state.

11. The apparatus of claim 2, wherein the first fixation plate comprises a fastener-lock mechanism configured to prohibit the first fastener from backing out of the first aperture in the first fixation plate, and the second fixation plate comprises a fastener-lock mechanism configured to prohibit the second fastener from backing out of the aperture in the second fixation plate.

12. The apparatus of claim 11, wherein at least one of the fastener-lock mechanism of the first fixation plate and the fastener-lock mechanism of the second fastener plate comprises a lock component and a compression spring loaded on the lock component, the compression spring has a free state and a compressed state allowing the lock component to extend over or retracted from the first aperture in the first fixation plate or the second aperture of the second fixation plate.

13. The apparatus of claim 2, wherein the first fixation plate comprises an edge portion having a concave profile, the second fixation plate comprises an edge portion having a convex profile, thereby allowing the first fixation plate and the second fixation plate to at least partially intermesh when being attached to the interbody fusion device in a contracted configuration.

14. The apparatus of claim 2, wherein the first drive shaft and the second drive shaft are independently operable in driving the first wedge member and the second wedge member to different positions, thereby a degree of expansion of the interbody fusion device along the first lateral area of the housing is independently adjustable relative to a degree of expansion of the interbody fusion device along the second lateral area of the housing.

15. The apparatus of claim 14, wherein the first wedge member comprises a first pair of screw members, the second wedge member comprises a second pair of screw members;

the first shell member comprises a plurality of individual riser members, and the second shell member comprises a plurality of individual riser members, the plurality of individual riser members of the first shell member and the plurality of individual riser members of the second shell member defining a first tracking run along the first lateral area of the housing and a second tracking run along the second lateral area of the housing; and the first drive shaft is operable to rotate the first pair of screw members allowing the first pair of screw members to travel along the first drive shaft and move on the first tracking run, and the second drive shaft is operable to rotate the second pair of screw members allowing the second pair of screw members to travel along the second drive shaft and move on the second tracking run.

16. The apparatus of claim 15, wherein the first drive shaft and second drive shaft each comprise an end portion provided with an external thread and an internal thread, the external thread being configured for connecting with an operation instrument, and the internal thread being configured for engaging a driver in the operation instrument for applying torque.

17. The apparatus of claim 16, wherein the first and second fixation plates each comprises an attachment lock mechanism engageable to lock the interbody fusion device, the attachment lock mechanism comprising a lock housing, a rod having a first end portion and a second end portion, a compression spring loaded on the rod and retained in the lock housing, and a latch coupled to the second end portion of the rod, wherein the first end portion of the rod is provided with an internal thread substantially the same as the internal thread of the first and second drive shafts, and the lock housing being adjacent to the first end portion of the rod and is provided with a thread substantially the same as the external thread of the first and second drive shafts, thereby allowing the operation instrument for connecting with and driving the first and second drive shafts of the interbody fusion device to connect with the first and second fixation plates and actuate the attachment-lock mechanisms of the first and second fixation plates respectively.

18. The apparatus of claim 17, wherein the first fixation plate further comprises a first fastener-lock mechanism configured to prohibit the first fastener from backing out of the first aperture in the first fixation plate, and the second fixation plate further comprises a second fastener lock mechanism configured to prohibit the second fastener from backing out of the second aperture in the second fixation plate.

19. The apparatus of claim 18, wherein at least one of the fastener-lock mechanism of the first fixation plate and the fastener-lock mechanism of the second fastener plate comprises a lock component and a compression spring loaded on the lock component, the compression spring has a free state and a compressed state allowing the lock component to extend over or retracted from the first aperture in the first fixation plate or the second aperture of the second fixation plate.

20. The apparatus of claim 15, wherein the first drive shaft and the second drive shaft are continuously operable to allow a distance between the first and second shell members at the first and/or second lateral areas of the housing to be continuously changeable, thereby allowing a height of the expanded configuration of the interbody fusion device to continuously change.

21. The apparatus of claim 15, wherein the first drive shaft and the second drive shaft are continuously operable to allow an angle between the first and second shell members to be continuously changeable, thereby allowing a lordosis or kyphosis of the expanded configuration of the interbody fusion device to be continuously variable.

22. A spinal system comprising an interbody fusion device and a fixation assembly, wherein the interbody fusion device comprising a housing, a first wedge member, a second wedge member, a first drive shaft, and a second drive shaft, wherein the housing comprises a first shell member and a second shell member, the first and second shell members engaging the first wedge member along a first lateral area of the housing, and engaging the second wedge member along a second lateral area of the housing;

the first wedge member is provided with a through-opening configured to allow the first drive shaft to pass, the second wedge member is provided with a through-opening configured to allow the second drive shaft to pass; and the first drive shaft is operable to drive the first wedge member along the first lateral area of the housing, the second drive shaft is operable to drive second wedge member along the second lateral area of the housing, causing the first and second shell members to move relative to each other providing an expanded configuration of the interbody fusion device; and the fixation assembly comprising a single fixation plate, a first fastener, and a second fastener, wherein the single fixation plate is configured to be attachable to the interbody fusion device in the expanded configuration, and is provided with a first aperture for insertion of the first fastener therethrough to a first vertebral body and a second aperture for insertion of the second fastener therethrough to a second vertebral body, thereby allowing the single fixation plate to be attached to the interbody fusion device in situ and secured to the first and second vertebral bodies to stabilize and/or prevent migration of the interbody fusion device.

23. The system of claim 22, wherein the single fixation plate is constructed from a material having strength capable of providing supplemental fixation of the first and second vertebral bodies.

24. The system of claim 22, wherein the single fixation plate comprises a first male geometry and a second male geometry, the first drive shaft of the interbody fusion device comprises an end portion having a first female geometry, the second drive shaft of the interbody fusion device comprises an end portion having a second female geometry, wherein the first male geometry of the single fixation plate and the first female geometry of the first drive shaft of the interbody fusion device are configured to have complementary mating features, the second male geometry of the single fixation plate and the second female geometry of the second drive shaft of the interbody fusion device are configured to have complementary mating features, whereby when the single fixation plate is attached to the interbody fusion device, the first and second male geometries of the single fixation plate engage the first and second female geometries in the end portions of the first and second drive shafts in the interbody fusion device respectively, restricting an unwanted rotation of the first and second drive shafts.

25. The system of claim 22, wherein the single fixation plate comprises a protruding portion configured to be insertable into the interbody fusion device, the protruding portion having a geometry configured to mate with a component in the interbody fusion device, thereby restricting an unwanted movement of the interbody fusion device, and wherein the single fixation plate further comprises an attachment-lock mechanism engageable to lock the interbody fusion device.

26. The system of claim 25, wherein the attachment-lock mechanism comprises a lock housing in the protruding portion of the single fixation plate, a rod having a first end portion and a second end portion, a compression spring loaded on the rod and retained in the lock housing, and a latch coupled to the second end portion of the rod, the latch being engageable to rotate to hook a component in the interbody fusion device.

27. The system of claim 22, wherein the single fixation plate further comprises a first fastener-lock mechanism configured to prohibit the first fastener from backing out of the first aperture and a second fastener-lock mechanism configured to prohibit the second fastener from backing out of the second aperture.

28. The system of claim 27, wherein at least one of the first fastener-lock mechanism and the second fastener-lock mechanism comprises a lock component and a compression spring loaded on the lock component, the compression spring having a free state allowing the lock component to extend over the first aperture or the second aperture and a compressed state allowing the lock component to be forced away from the first aperture or the second aperture.

29. The system of claim 22, wherein the first drive shaft and the second drive shaft are independently operable to drive the first wedge member and the second wedge member separately to different positions, thereby a degree of expansion of the interbody fusion device along the first lateral area of the housing is independently adjustable relative to a degree of expansion of the interbody fusion device along the second lateral area of the housing.

30. A spinal system comprising an interbody fusion device and a fixation assembly, wherein the interbody fusion device comprising a housing, a first wedge member, a second wedge member, a first drive shaft, and a second drive shaft, wherein the housing comprises a first shell member and a second shell member, the first and second shell members engaging the first wedge member along a first lateral area of the housing, and engaging the second wedge member along a second lateral area of the housing;

the first wedge member is provided with a through-opening configured to allow the first drive shaft to pass, the second wedge member is provided with a through-opening configured to allow the second drive shaft to pass; and the first drive shaft is operable to drive the first wedge member along the first lateral area of the housing, the second drive shaft is operable to drive second wedge member along the second lateral area of the housing, causing the first and second shell members to move relative to each other providing an expanded configuration of the interbody fusion device; and the fixation assembly comprising a single fixation plate, a first fastener, and a second fastener, the single fixation plate being provided with a first aperture for insertion of the first fastener therethrough to a first vertebral body and a second aperture for insertion of the second fastener therethrough to a second vertebral body, wherein the single fixation plate is insertable into the interbody fusion device in situ and rotatable relative to the interbody fusion device, thereby allowing positioning of the first aperture and the second aperture in the single fixation plate to be adjusted in situ, the single fixation plate being constructed to be capable of providing supplemental fixation of the first and second vertebral bodies.

31. The system of claim 30, wherein the single fixation plate is rotatable relative to an imaginary plane containing the first and second drive shafts of the interbody fusion device at an angle from 0 to 11 degrees clockwise and/or counterclockwise, thereby allowing the positioning of the first and second apertures in the single fixation plate to be adjusted in situ at an angle from 0 to 11 degrees clockwise and/or counterclockwise.

32. The system of claim 31, wherein the single fixation plate comprises a protruding portion configured to be inserted into the interbody fusion device in the expanded configuration, and wherein the single fixation plate is optionally attachable to the interbody fusion device via the protruding portion of the single fixation plate.

33. The system of claim 32, wherein the single fixation plate further comprises an attachment-lock mechanism engageable to lock the interbody fusion device to the single fixation plate.

34. An apparatus comprising an interbody fusion device and a fixation assembly, wherein the interbody fusion device comprising a housing, a first wedge member, a second wedge member, a first drive shaft, and a second drive shaft, wherein the housing comprises a first shell member and a second shell member, the first and second shell members engaging the first wedge member along a first lateral area of the housing, and engaging the second wedge member along a second lateral area of the housing;

the first wedge member is provided with a through-opening configured to allow the first drive shaft to pass, the second wedge member is provided with a through-opening configured to allow the second drive shaft to pass; and the first drive shaft is operable to drive the first wedge member along the first lateral area of the housing, the second drive shaft is operable to drive second wedge member along the second lateral area of the housing, causing the first and second shell members to move relative to each other providing an expanded configuration of the interbody fusion device; and the fixation assembly comprising a first fixation plate having a first aperture for insertion of a first fastener and a second fixation plate having a second aperture for insertion of a second fastener, wherein the first fixation plate is coupled to the first shell member and the second fixation plate is coupled to the second shell member, thereby allowing the first and second fixation plates to be implanted with the interbody fusion device, angle-adjusted in situ with movement of the first shell member and/or second shell member, and fastened to adjacent vertebral bodies to stabilize and/or prevent migration of the interbody fusion device.

35. The apparatus of claim 34, wherein the first fixation plate is integrally formed with the first shell member, and/or, the second fixation plate is integrally formed with the second shell member.

36. The apparatus of claim 34, wherein the first fixation plate is a separate piece and coupled to the first shell member by interference fit or screw coupling, and/or, the second fixation plate is a separate piece and coupled to the second shell member by interference fit or screw coupling.

37. The apparatus of claim 34, wherein the first aperture in the first fixation plate is configured to allow a trajectory of the first fastener to be adjusted at an angle from 0-15 degrees, and/or the second aperture in the second fixation plate is configured to allow a trajectory of the second fastener to be adjusted at an angle from 0-15 degrees.

38. The apparatus of claim 34, wherein the first fixation plate comprises a first fastener-lock mechanism configured to prohibit the first fastener from backing out of the first aperture in the first fixation plate, and/or, the second fixation plate comprises a second fastener-lock mechanism configured to prohibit the second fastener from backing out of the second aperture in the second fixation plate.

39. The apparatus of claim 38, wherein the first fastener-lock mechanism comprises a lock rod including a head having a rounded side portion and a flat side portion, the lock rod being rotatable allowing the rounded side portion to extend over the first aperture to provide a locked state of the first fastener-lock mechanism or allowing the flat side portion to face the first aperture to provide an unlocked state of the first fastener-lock mechanism.

40. The apparatus of claim 39, wherein the second fastener-lock mechanism comprises a lock rod same as or similar to the lock rod of the first fastener-lock mechanism.

41. The apparatus of claim 34, wherein the first drive shaft and the second drive shaft are independently operable to drive the first wedge member and the second wedge member separately to different positions, thereby a degree of expansion of the interbody fusion device along the first lateral area of the housing is independently adjustable relative to a degree of expansion of the interbody fusion device along the second lateral area of the housing.

* * * * *